United States Patent
McLaren et al.

(10) Patent No.: US 12,226,582 B2
(45) Date of Patent: Feb. 18, 2025

(54) HEADGEAR FOR PATIENT INTERFACE

(71) Applicant: Fisher & Paykel Healthcare Limited, Auckland (NZ)

(72) Inventors: Mark Arvind McLaren, Auckland (NZ); Jeroen Hammer, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/476,165

(22) Filed: Sep. 27, 2023

(65) Prior Publication Data

US 2024/0123175 A1 Apr. 18, 2024

Related U.S. Application Data

(63) Continuation of application No. 16/509,958, filed on Jul. 12, 2019, now Pat. No. 11,806,452, which is a continuation of application No. 15/047,436, filed on Feb. 18, 2016, now abandoned, which is a continuation of application No. 14/420,284, filed as
(Continued)

(51) Int. Cl.
  *A61M 16/06* (2006.01)
  *A62B 18/08* (2006.01)

(52) U.S. Cl.
  CPC ........ *A61M 16/0683* (2013.01); *A61M 16/06* (2013.01); *A61M 16/0605* (2014.02); *A61M 2016/0661* (2013.01); *A61M 2205/0216* (2013.01); *A61M 2205/0272* (2013.01); *A62B 18/084* (2013.01)

(58) Field of Classification Search
  CPC .. A61M 16/00; A61M 16/06; A61M 16/0605; A61M 16/0666; A61M 16/0683; A61M 16/0694; A62B 9/00; A62B 9/04; A62B 18/00; A62B 18/02; A62B 18/025; A62B 18/084; A42B 1/22; A42B 3/145
  See application file for complete search history.

(56) References Cited

U.S. PATENT DOCUMENTS

| | | | |
|---|---|---|---|
| 301,111 | A | 7/1884 | Genese |
| 472,238 | A | 4/1892 | Van Orden |
| 577,926 | A | 3/1897 | Miller |

(Continued)

FOREIGN PATENT DOCUMENTS

| | | |
|---|---|---|
| CA | 996301 | 9/1976 |
| CA | 1311662 | 12/1992 |

(Continued)

OTHER PUBLICATIONS cpap.com, InnoMed/Resp Care Bravo Nasal Pillow CPAP Mask with Headgear, (http://web.archive.org/web/*/https://www.cpap.com/productpage/bravo-nasal-interface/), downloaded Feb. 24, 2020, 5 pp.

(Continued)

*Primary Examiner* — Colin W Stuart
(74) *Attorney, Agent, or Firm* — VIA LLP

(57) ABSTRACT

An interface includes a mask. The mask includes a frame and a seal supported by the frame. Headgear is connected to the mask. The interface includes at least one of (i) an adjustment mechanism that can be set to a use length for a loop defined by the mask and the headgear; and (2) a break-fit assembly that can selectively lengthen the loop defined by the mask and the headgear and return to the use length.

8 Claims, 37 Drawing Sheets

Related U.S. Application Data application No. PCT/NZ2013/000139 on Aug. 8, 2013, now Pat. No. 10,080,856.

(60) Provisional application No. 61/681,024, filed on Aug. 8, 2012.

(56) References Cited

U.S. PATENT DOCUMENTS

| | | |
|---|---|---|
| 718,470 A | 1/1903 | Jones |
| 751,091 A | 2/1904 | Moran |
| 770,013 A | 9/1904 | Linn |
| 1,364,104 A | 1/1921 | Geer |
| 1,635,545 A | 7/1927 | Drager |
| 1,942,442 A | 1/1934 | Motsinger |
| 2,199,690 A | 5/1940 | Bullard |
| 2,296,150 A | 9/1942 | Dockson et al. |
| 2,353,643 A | 7/1944 | Bulbulian |
| 2,359,506 A | 10/1944 | Battley et al. |
| 2,388,604 A | 11/1945 | Eisenbud |
| 2,390,233 A | 12/1945 | Akerman et al. |
| 2,508,050 A | 5/1950 | Valente |
| 2,586,851 A | 2/1952 | Monro et al. |
| 2,611,897 A | 9/1952 | Adams |
| 2,661,514 A | 12/1953 | Ada |
| 2,693,800 A | 11/1954 | Caldwell |
| 2,738,788 A | 3/1956 | Matheson et al. |
| 2,843,121 A | 7/1958 | Hudson |
| 2,859,748 A | 11/1958 | Hudson |
| 3,045,672 A | 7/1962 | Croasdaile |
| 3,156,922 A | 11/1964 | Anderson |
| 3,295,529 A | 1/1967 | Corrigall et al. |
| 3,416,521 A | 12/1968 | Humphrey |
| 3,457,564 A | 7/1969 | Holloway |
| 3,490,452 A | 1/1970 | Greenfield |
| 3,500,474 A | 3/1970 | Austin |
| 3,530,031 A | 9/1970 | Loew |
| 3,792,702 A | 2/1974 | Delest |
| 3,834,682 A | 9/1974 | McPhee |
| 3,850,171 A | 11/1974 | Ball et al. |
| 3,887,968 A | 6/1975 | Lynam |
| 3,972,321 A | 8/1976 | Proctor |
| 3,990,757 A | 11/1976 | Gill |
| 3,992,720 A | 11/1976 | Nicolinas |
| 3,994,022 A | 11/1976 | Villari et al. |
| 4,051,556 A | 10/1977 | Davenport et al. |
| 4,062,068 A | 12/1977 | Davenport et al. |
| 4,090,510 A | 5/1978 | Segersten |
| 4,106,165 A | 8/1978 | Clowers et al. |
| D250,047 S | 10/1978 | Lewis et al. |
| D250,131 S | 10/1978 | Lewis et al. |
| 4,127,130 A | 11/1978 | Naysmith |
| D252,322 S | 7/1979 | Johnson |
| 4,167,185 A | 9/1979 | Lewis |
| 4,201,205 A | 5/1980 | Bartholomew |
| 4,266,540 A | 5/1981 | Panzik et al. |
| 4,278,082 A | 7/1981 | Blackmer |
| 4,288,891 A | 9/1981 | Boden |
| 4,313,437 A | 2/1982 | Martin |
| 4,328,605 A | 5/1982 | Hutchinson et al. |
| 4,354,488 A | 10/1982 | Bartos |
| 4,367,735 A | 1/1983 | Dali |
| 4,402,316 A | 9/1983 | Gadberry |
| 4,413,382 A | 11/1983 | Siegmann |
| 4,437,462 A | 3/1984 | Piljay |
| 4,453,292 A | 6/1984 | Bakker |
| 4,458,373 A | 7/1984 | Maslow |
| 4,477,928 A | 10/1984 | Graff |
| 4,606,077 A | 8/1986 | Phillips |
| D293,613 S | 1/1988 | Wingler |
| 4,734,940 A | 4/1988 | Galet et al. |
| 4,753,233 A | 6/1988 | Grimes |
| 4,782,832 A | 11/1988 | Trimble et al. |
| 4,817,596 A | 4/1989 | Gallet |
| 4,848,334 A | 7/1989 | Bellm |
| 4,853,275 A | 8/1989 | Tracy et al. |
| 4,856,508 A | 8/1989 | Tayebi |
| 4,915,105 A | 4/1990 | Lee |
| 4,941,467 A | 7/1990 | Takata |
| 4,944,310 A | 7/1990 | Sullivan |
| 4,947,488 A | 8/1990 | Ashinoff |
| D310,431 S | 9/1990 | Bellm |
| 4,971,051 A | 11/1990 | Toffolon |
| 4,986,269 A | 1/1991 | Hakkinen |
| 5,010,925 A | 4/1991 | Atkinson et al. |
| 5,016,625 A | 5/1991 | Hsu et al. |
| 5,042,478 A | 8/1991 | Kopala et al. |
| D320,677 S | 10/1991 | Kumagai et al. |
| 5,052,084 A | 10/1991 | Braun |
| D321,419 S | 11/1991 | Wallace |
| 5,065,756 A | 11/1991 | Rapoport |
| 5,074,297 A | 12/1991 | Venegas |
| 5,094,236 A | 3/1992 | Tayebi |
| 5,113,857 A | 5/1992 | Dickerman et al. |
| 5,148,578 A | 9/1992 | Clarke et al. |
| 5,148,802 A | 9/1992 | Sanders et al. |
| 5,191,882 A | 3/1993 | Vogliano |
| 5,231,979 A | 8/1993 | Rose |
| 5,245,995 A | 9/1993 | Sullivan et al. |
| D340,317 S | 10/1993 | Cole |
| 5,269,296 A | 12/1993 | Landis et al. |
| D354,128 S | 1/1995 | Rinehart |
| D355,484 S | 2/1995 | Rinehart |
| 5,388,743 A | 2/1995 | Silagy |
| 5,438,979 A | 8/1995 | Johnson et al. |
| 5,477,852 A | 12/1995 | Landis et al. |
| 5,488,948 A | 2/1996 | Dubruille |
| 5,513,634 A | 5/1996 | Jackson |
| 5,529,062 A | 6/1996 | Byrd |
| 5,533,506 A | 7/1996 | Wood |
| 5,546,605 A | 8/1996 | Mallardi |
| 5,551,419 A | 9/1996 | Froehlich et al. |
| 5,566,395 A | 10/1996 | Nebeker |
| 5,595,174 A | 1/1997 | Gwaltney |
| 5,601,078 A | 2/1997 | Schaller et al. |
| D378,610 S | 3/1997 | Reischel et al. |
| 5,657,752 A | 8/1997 | Landis et al. |
| 5,724,965 A | 3/1998 | Handke et al. |
| 5,752,510 A | 5/1998 | Goldstein |
| 5,755,578 A | 5/1998 | Contant et al. |
| 5,774,901 A | 7/1998 | Minami |
| 5,823,020 A | 10/1998 | Benda |
| 5,884,624 A | 3/1999 | Barnett et al. |
| 5,921,239 A | 7/1999 | McCall et al. |
| 5,941,245 A | 8/1999 | Hannah et al. |
| 5,941,856 A | 8/1999 | Kovacs et al. |
| 6,017,315 A | 1/2000 | Starr et al. |
| 6,019,101 A | 2/2000 | Cotner et al. |
| 6,044,844 A | 4/2000 | Kwok et al. |
| 6,050,260 A | 4/2000 | Daniell et al. |
| 6,119,694 A | 9/2000 | Correa et al. |
| 6,192,886 B1 | 2/2001 | Rudolph |
| D440,302 S | 4/2001 | Wolfe |
| 6,256,798 B1 | 7/2001 | Egolf et al. |
| 6,272,690 B1 | 8/2001 | Carey et al. |
| 6,282,725 B1 | 9/2001 | Vanidestine, Jr. |
| 6,298,850 B1 | 10/2001 | Argraves |
| 6,338,342 B1 | 1/2002 | Fecteau et al. |
| 6,347,631 B1 | 2/2002 | Hansen et al. |
| D455,891 S | 4/2002 | Biedrzycki |
| 6,418,928 B1 | 7/2002 | Bordewick et al. |
| 6,422,238 B1 | 7/2002 | Lithgow |
| 6,431,172 B1 | 8/2002 | Bordewick |
| 6,435,181 B1 | 8/2002 | Jones, Jr. et al. |
| 6,439,234 B1 | 8/2002 | Curti et al. |
| 6,470,886 B1 | 10/2002 | Jestrabek-Hart |
| 6,478,026 B1 | 11/2002 | Wood |
| 6,491,034 B1 | 12/2002 | Gunaratnam et al. |
| 6,536,435 B1 | 3/2003 | Fecteau et al. |
| 6,561,188 B1 | 5/2003 | Ellis |
| 6,561,191 B1 | 5/2003 | Kwok |
| 6,571,854 B1 | 6/2003 | Palmer |
| 6,581,594 B1 | 6/2003 | Drew et al. |
| 6,581,601 B2 | 6/2003 | Ziaee |
| 6,588,424 B2 | 7/2003 | Bardel |

(56) References Cited

U.S. PATENT DOCUMENTS

| | | |
|---|---|---|
| 6,631,718 B1 | 10/2003 | Lovell |
| 6,637,434 B2 | 10/2003 | Noble |
| 6,644,315 B2 | 11/2003 | Ziaee |
| 6,651,658 B1 | 11/2003 | Hill et al. |
| 6,659,102 B1 | 12/2003 | Sico |
| 6,662,803 B2 | 12/2003 | Gradon et al. |
| 6,679,257 B1 | 1/2004 | Robertson et al. |
| 6,679,265 B2 | 1/2004 | Strickland et al. |
| 6,772,761 B1 | 8/2004 | Rucker, Jr. |
| 6,851,425 B2 | 2/2005 | Jaffre et al. |
| 6,883,519 B2 | 4/2005 | Schmidtke et al. |
| 6,886,564 B2 | 5/2005 | Sullivan et al. |
| 6,892,729 B2 | 5/2005 | Smith et al. |
| 6,907,882 B2 | 6/2005 | Ging et al. |
| 6,951,218 B2 | 10/2005 | Gradon et al. |
| 7,004,165 B1 | 2/2006 | Salcido |
| D520,140 S | 5/2006 | Chaggares |
| 7,036,508 B2 | 5/2006 | Kwok |
| 7,062,795 B2 | 6/2006 | Skiba et al. |
| 7,066,179 B2 | 6/2006 | Eaton et al. |
| D526,094 S | 8/2006 | Chen |
| 7,096,864 B1 | 8/2006 | Mayer et al. |
| 7,096,867 B2 | 8/2006 | Smith et al. |
| 7,201,169 B2 | 4/2007 | Wilkie et al. |
| 7,207,333 B2 | 4/2007 | Tohara |
| 7,210,481 B1 | 5/2007 | Lovell et al. |
| 7,219,669 B1 | 5/2007 | Lovell et al. |
| 7,225,811 B2 | 6/2007 | Ruiz et al. |
| 7,318,437 B2 | 1/2008 | Gunaratnam et al. |
| 7,353,826 B2 | 4/2008 | Sleeper et al. |
| 7,353,827 B2 | 4/2008 | Geist |
| 7,814,911 B2 | 10/2010 | Bordewick et al. |
| 7,845,352 B2 | 12/2010 | Sleeper et al. |
| 7,861,715 B2 | 1/2011 | Jones et al. |
| 7,870,860 B2 | 1/2011 | McCormick et al. |
| 7,896,003 B2 | 3/2011 | Matula et al. |
| 7,913,692 B2 | 3/2011 | Kwok |
| 7,967,014 B2 | 6/2011 | Heidmann |
| 8,042,539 B2 | 10/2011 | Chandran et al. |
| 8,047,893 B2 | 11/2011 | Fenske |
| 8,074,651 B2 | 12/2011 | Bierman et al. |
| 8,104,473 B2 | 1/2012 | Woodard et al. |
| 8,132,270 B2 | 3/2012 | Lang et al. |
| 8,136,524 B2 | 3/2012 | Ging et al. |
| 8,209,995 B2 | 7/2012 | Kieling et al. |
| 8,297,285 B2 | 10/2012 | Henry et al. |
| 8,371,302 B2 | 2/2013 | Ging et al. |
| 8,443,807 B2 | 5/2013 | McAuley et al. |
| D686,313 S | 7/2013 | Matula et al. |
| 8,479,741 B2 | 7/2013 | McAuley et al. |
| 8,505,538 B2 | 8/2013 | Amarasinghe |
| 8,517,025 B2 | 8/2013 | Ho et al. |
| 8,522,785 B2 | 9/2013 | Berthon-Jones et al. |
| 8,573,201 B2 | 11/2013 | Rummery et al. |
| 8,596,271 B2 | 12/2013 | Matula, Jr. et al. |
| 8,596,274 B2 | 12/2013 | Hieber et al. |
| 8,631,793 B2 | 1/2014 | Omura et al. |
| 8,636,005 B2 | 1/2014 | Gradon et al. |
| 8,636,007 B2 | 1/2014 | Rummery et al. |
| 8,636,008 B2 | 1/2014 | Flory et al. |
| 8,757,157 B2 | 6/2014 | Price et al. |
| 8,783,257 B2 | 7/2014 | McAuley et al. |
| 8,794,239 B2 | 8/2014 | Gunaratnam |
| 8,839,789 B2 | 9/2014 | Guney et al. |
| 8,856,975 B2 | 10/2014 | Lang et al. |
| 8,857,435 B2 | 10/2014 | Matula, Jr. et al. |
| 8,915,251 B2 | 12/2014 | Lubke et al. |
| 8,950,404 B2 | 2/2015 | Formica et al. |
| 8,997,742 B2 | 4/2015 | Moore et al. |
| 9,032,955 B2 | 5/2015 | Lubke et al. |
| 9,044,564 B2 | 6/2015 | Dravitzki et al. |
| 9,103,161 B2 | 8/2015 | Mader |
| 9,138,555 B2 | 9/2015 | McAuley et al. |
| 9,149,596 B2 | 10/2015 | Valcic et al. |
| 9,265,909 B2 | 2/2016 | Ho et al. |
| 9,302,065 B2 | 4/2016 | Smith et al. |
| 9,320,866 B2 | 4/2016 | McAuley et al. |
| 9,333,315 B2 | 5/2016 | McAuley et al. |
| 9,339,622 B2 | 5/2016 | McAuley et al. |
| 9,480,809 B2 | 11/2016 | Guney et al. |
| 9,517,320 B2 | 12/2016 | Barlow et al. |
| 9,550,038 B2 | 1/2017 | McAuley et al. |
| 9,555,943 B2 | 1/2017 | Breen, IV et al. |
| 9,592,336 B2 | 3/2017 | Nielsen et al. |
| 9,629,974 B2 | 4/2017 | Gibson |
| 9,656,038 B2 | 5/2017 | Rummery et al. |
| 9,744,385 B2 | 8/2017 | Henry |
| 9,782,554 B2 | 10/2017 | Mazzone et al. |
| 9,878,118 B2 | 1/2018 | Formica |
| D810,277 S | 2/2018 | Amarasinghe |
| 9,884,160 B2 | 2/2018 | McAuley |
| 9,901,700 B2 | 2/2018 | McAuley et al. |
| 9,925,349 B2 | 3/2018 | Jablonski |
| 9,974,914 B2 | 5/2018 | McAuley |
| 9,993,606 B2 | 6/2018 | Gibson et al. |
| 10,039,665 B2 | 8/2018 | Blaszczykiewicz et al. |
| 10,065,010 B2 | 9/2018 | Smith et al. |
| 10,071,217 B2 | 9/2018 | Grashow |
| 10,080,856 B2 | 9/2018 | McLaren |
| 10,137,319 B2 | 11/2018 | Carr et al. |
| 10,207,072 B2 | 2/2019 | Dunn et al. |
| 10,279,138 B2 | 5/2019 | Ovzinsky |
| 10,456,546 B2 | 10/2019 | McLaren et al. |
| 10,646,680 B2 | 5/2020 | Huddart et al. |
| 10,668,242 B2 | 6/2020 | Bearne |
| 10,675,428 B2 | 6/2020 | Guney et al. |
| 10,792,451 B2 | 10/2020 | Allan et al. |
| 10,828,449 B2 | 11/2020 | Higgins et al. |
| 10,828,452 B2 | 11/2020 | Huddart et al. |
| 10,874,814 B2 | 12/2020 | Huddart et al. |
| 11,000,663 B2 | 5/2021 | Felix et al. |
| 11,253,668 B2 | 2/2022 | Freestone |
| 11,331,449 B2 | 5/2022 | McLaren et al. |
| 11,419,999 B2 | 8/2022 | Patel et al. |
| 11,607,518 B2 | 3/2023 | Hammer et al. |
| 11,648,365 B2 | 5/2023 | Huddart et al. |
| 11,701,486 B2 | 7/2023 | Mashal et al. |
| 11,752,292 B2 | 9/2023 | McLaren et al. |
| 11,806,452 B2 | 11/2023 | Mclaren et al. |
| 11,850,365 B2 | 12/2023 | Freestone et al. |
| 12,102,765 B2 | 10/2024 | Huddart et al. |
| 2001/0020474 A1 | 9/2001 | Hecker et al. |
| 2001/0029952 A1 | 10/2001 | Curran |
| 2002/0005198 A1 | 1/2002 | Kwok et al. |
| 2002/0014241 A1 | 2/2002 | Gradon et al. |
| 2002/0020416 A1 | 2/2002 | Namey |
| 2002/0026934 A1 | 3/2002 | Lithgow et al. |
| 2002/0029780 A1 | 3/2002 | Frater et al. |
| 2002/0039867 A1 | 4/2002 | Curro et al. |
| 2002/0046755 A1 | 4/2002 | Voss |
| 2002/0052568 A1 | 5/2002 | Houser et al. |
| 2002/0053347 A1 | 5/2002 | Ziaee |
| 2002/0059935 A1 | 5/2002 | Wood |
| 2002/0069467 A1 | 6/2002 | Immediato et al. |
| 2002/0096176 A1 | 7/2002 | Gunaratnam et al. |
| 2002/0096178 A1 | 7/2002 | Ziaee |
| 2002/0100474 A1 | 8/2002 | Kellner et al. |
| 2002/0100479 A1 | 8/2002 | Scarberry et al. |
| 2002/0108613 A1 | 8/2002 | Gunaratnam et al. |
| 2002/0157668 A1 | 10/2002 | Bardel |
| 2003/0005509 A1 | 1/2003 | Kelzer |
| 2003/0005931 A1 | 1/2003 | Jaffre et al. |
| 2003/0005933 A1 | 1/2003 | Izuchukwu |
| 2003/0019495 A1 | 1/2003 | Palkon et al. |
| 2003/0019496 A1 | 1/2003 | Kopacko et al. |
| 2003/0029454 A1 | 2/2003 | Gelinas et al. |
| 2003/0047185 A1 | 3/2003 | Olsen et al. |
| 2003/0051732 A1 | 3/2003 | Smith et al. |
| 2003/0075180 A1 | 4/2003 | Raje |
| 2003/0075182 A1 | 4/2003 | Heidmann et al. |
| 2003/0079749 A1 | 5/2003 | Strickland et al. |
| 2003/0084903 A1 | 5/2003 | Fecteau et al. |
| 2003/0084996 A1 | 5/2003 | Alberg et al. |
| 2003/0089373 A1 | 5/2003 | Gradon et al. |

(56) References Cited

U.S. PATENT DOCUMENTS

| | | |
|---|---|---|
| 2003/0094177 A1 | 5/2003 | Smith et al. |
| 2003/0111080 A1 | 6/2003 | Olsen et al. |
| 2003/0121519 A1 | 7/2003 | Estes et al. |
| 2003/0149384 A1 | 8/2003 | Davis et al. |
| 2003/0164170 A1 | 9/2003 | Drew et al. |
| 2003/0172936 A1 | 9/2003 | Wilkie et al. |
| 2003/0196655 A1 | 10/2003 | Ging et al. |
| 2003/0196656 A1 | 10/2003 | Moore |
| 2003/0196658 A1 | 10/2003 | Ging et al. |
| 2003/0196659 A1 | 10/2003 | Gradon et al. |
| 2003/0196664 A1 | 10/2003 | Jacobson |
| 2003/0200970 A1 | 10/2003 | Stenzler et al. |
| 2003/0217746 A1 | 11/2003 | Gradon et al. |
| 2003/0221691 A1 | 12/2003 | Biener |
| 2004/0011087 A1 | 1/2004 | Rebouillat et al. |
| 2004/0025882 A1 | 2/2004 | Madaus et al. |
| 2004/0035427 A1 | 2/2004 | Bordewick et al. |
| 2004/0065328 A1 | 4/2004 | Amarasinghe et al. |
| 2004/0067333 A1 | 4/2004 | Amarasinghe |
| 2004/0094157 A1 | 5/2004 | Dantanarayana et al. |
| 2004/0107968 A1 | 6/2004 | Griffiths |
| 2004/0112377 A1 | 6/2004 | Amarasinghe et al. |
| 2004/0112384 A1 | 6/2004 | Lithgow et al. |
| 2004/0112385 A1 | 6/2004 | Drew |
| 2004/0118406 A1 | 6/2004 | Lithgow |
| 2004/0118412 A1 | 6/2004 | Piletti-Reyes |
| 2004/0139973 A1 | 7/2004 | Wright |
| 2004/0149280 A1 | 8/2004 | Semeniuk |
| 2004/0182398 A1 | 9/2004 | Sprinkle et al. |
| 2004/0211427 A1 | 10/2004 | Jones et al. |
| 2004/0221850 A1 | 11/2004 | Ging et al. |
| 2004/0226566 A1 | 11/2004 | Gunaratnam et al. |
| 2004/0255949 A1 | 12/2004 | Lang et al. |
| 2005/0011521 A1 | 1/2005 | Sprinkle et al. |
| 2005/0011524 A1 | 1/2005 | Thomlinson et al. |
| 2005/0016067 A1 | 1/2005 | Pettit |
| 2005/0016532 A1 | 1/2005 | Farrell |
| 2005/0028822 A1 | 2/2005 | Sleeper et al. |
| 2005/0033247 A1 | 2/2005 | Thompson |
| 2005/0045182 A1 | 3/2005 | Wood et al. |
| 2005/0051177 A1 | 3/2005 | Wood |
| 2005/0066976 A1 | 3/2005 | Wondka |
| 2005/0076913 A1 | 4/2005 | Ho et al. |
| 2005/0092327 A1 | 5/2005 | Fini et al. |
| 2005/0098183 A1 | 5/2005 | Nash et al. |
| 2005/0121037 A1 | 6/2005 | Wood |
| 2005/0133038 A1 | 6/2005 | Rutter |
| 2005/0150497 A1 | 7/2005 | Eifler et al. |
| 2005/0155604 A1 | 7/2005 | Ging et al. |
| 2005/0161049 A1 | 7/2005 | Wright |
| 2005/0172969 A1 | 8/2005 | Ging |
| 2005/0199239 A1 | 9/2005 | Lang et al. |
| 2005/0199242 A1 | 9/2005 | Matula et al. |
| 2005/0205096 A1 | 9/2005 | Matula |
| 2005/0235999 A1 | 10/2005 | Wood et al. |
| 2005/0241644 A1 | 11/2005 | Guney et al. |
| 2005/0262619 A1 | 12/2005 | Musal et al. |
| 2006/0032504 A1 | 2/2006 | Burton et al. |
| 2006/0042629 A1 | 3/2006 | Geist |
| 2006/0042632 A1 | 3/2006 | Bishop et al. |
| 2006/0054169 A1 | 3/2006 | Han et al. |
| 2006/0060200 A1 | 3/2006 | Ho et al. |
| 2006/0076019 A1 | 4/2006 | Ho |
| 2006/0081250 A1 | 4/2006 | Bordewick et al. |
| 2006/0081256 A1 | 4/2006 | Palmer |
| 2006/0096596 A1 | 5/2006 | Occhialini et al. |
| 2006/0096598 A1 | 5/2006 | Ho et al. |
| 2006/0107958 A1 | 5/2006 | Sleeper |
| 2006/0113147 A1 | 6/2006 | Harris |
| 2006/0118117 A1 | 6/2006 | Berthon-Jones et al. |
| 2006/0124131 A1 | 6/2006 | Chandran |
| 2006/0130844 A1 | 6/2006 | Ho et al. |
| 2006/0137690 A1 | 6/2006 | Gunaratnam et al. |
| 2006/0169286 A1 | 8/2006 | Eifler et al. |
| 2006/0174887 A1 | 8/2006 | Chandran et al. |
| 2006/0174892 A1 | 8/2006 | Leksutin et al. |
| 2006/0196510 A1 | 9/2006 | McDonald et al. |
| 2006/0196511 A1 | 9/2006 | Lau et al. |
| 2006/0201514 A1 | 9/2006 | Jones et al. |
| 2006/0207599 A1 | 9/2006 | Busch |
| 2006/0225740 A1 | 10/2006 | Eaton et al. |
| 2006/0231103 A1 | 10/2006 | Matula et al. |
| 2006/0237017 A1 | 10/2006 | Davidson et al. |
| 2006/0237018 A1 | 10/2006 | McAuley et al. |
| 2006/0249159 A1 | 11/2006 | Ho |
| 2006/0254593 A1 | 11/2006 | Chang |
| 2006/0266361 A1 | 11/2006 | Hernandez |
| 2006/0283458 A1 | 12/2006 | Woodard |
| 2006/0283459 A1 | 12/2006 | Geiselhart et al. |
| 2006/0283461 A1 | 12/2006 | Lubke et al. |
| 2007/0000492 A1 | 1/2007 | Hansel et al. |
| 2007/0010786 A1 | 1/2007 | Casey et al. |
| 2007/0044804 A1 | 3/2007 | Matula et al. |
| 2007/0062536 A1 | 3/2007 | McAuley |
| 2007/0089749 A1 | 4/2007 | Ho et al. |
| 2007/0107733 A1 | 5/2007 | Ho |
| 2007/0125384 A1 | 6/2007 | Zollinger et al. |
| 2007/0125385 A1 | 6/2007 | Ho et al. |
| 2007/0125387 A1 | 6/2007 | Zollinger et al. |
| 2007/0130663 A1 | 6/2007 | Lang et al. |
| 2007/0137653 A1 | 6/2007 | Wood |
| 2007/0142785 A1 | 6/2007 | Lundgaard et al. |
| 2007/0157353 A1 | 7/2007 | Guney et al. |
| 2007/0163600 A1 | 7/2007 | Hoffman |
| 2007/0169777 A1 | 7/2007 | Amarasinghe et al. |
| 2007/0174952 A1 | 8/2007 | Jacob |
| 2007/0175480 A1 | 8/2007 | Gradon et al. |
| 2007/0209663 A1 | 9/2007 | Marque et al. |
| 2007/0215161 A1 | 9/2007 | Frater et al. |
| 2007/0221227 A1 | 9/2007 | Ho |
| 2007/0227541 A1 | 10/2007 | Van Den |
| 2007/0235033 A1 | 10/2007 | Reier et al. |
| 2007/0272249 A1 | 11/2007 | Chandran |
| 2007/0295335 A1 | 12/2007 | Nashed |
| 2008/0035152 A1 | 2/2008 | Ho et al. |
| 2008/0041388 A1 | 2/2008 | McAuley et al. |
| 2008/0041393 A1 | 2/2008 | Bracken |
| 2008/0047560 A1 | 2/2008 | Veliss et al. |
| 2008/0052806 A1 | 3/2008 | McDaniel |
| 2008/0053450 A1 | 3/2008 | Van Kerkwyk et al. |
| 2008/0060648 A1 | 3/2008 | Thornton et al. |
| 2008/0060653 A1 | 3/2008 | Hallet et al. |
| 2008/0060657 A1 | 3/2008 | McAuley et al. |
| 2008/0065015 A1 | 3/2008 | Fiser |
| 2008/0083412 A1 | 4/2008 | Henry et al. |
| 2008/0092905 A1 | 4/2008 | Gunaratnam |
| 2008/0092906 A1 | 4/2008 | Gunaratnam et al. |
| 2008/0099024 A1 | 5/2008 | Gunaratnam et al. |
| 2008/0105257 A1 | 5/2008 | Klasek et al. |
| 2008/0110464 A1 | 5/2008 | Davidson et al. |
| 2008/0134480 A1 | 6/2008 | Shiue |
| 2008/0135050 A1 | 6/2008 | Hitchcock |
| 2008/0142019 A1 | 6/2008 | Lewis |
| 2008/0171737 A1 | 7/2008 | Fensome |
| 2008/0178875 A1 | 7/2008 | Henry |
| 2008/0178886 A1 | 7/2008 | Lieberman et al. |
| 2008/0190432 A1 | 8/2008 | Blochlinger et al. |
| 2008/0190436 A1 | 8/2008 | Jaffe et al. |
| 2008/0196728 A1 | 8/2008 | Ho |
| 2008/0210241 A1 | 9/2008 | Schulz et al. |
| 2008/0223370 A1 | 9/2008 | Kim |
| 2008/0230068 A1 | 9/2008 | Rudolph |
| 2008/0230069 A1 | 9/2008 | Valcic et al. |
| 2008/0236586 A1 | 10/2008 | Mcdonald et al. |
| 2008/0257354 A1 | 10/2008 | Davidson |
| 2008/0264422 A1 | 10/2008 | Fishman |
| 2008/0271739 A1 | 11/2008 | Facer et al. |
| 2008/0276937 A1 | 11/2008 | Davidson et al. |
| 2008/0302366 A1 | 12/2008 | McGinnis et al. |
| 2008/0314388 A1 | 12/2008 | Brambilla et al. |
| 2008/0319334 A1 | 12/2008 | Yamamori |
| 2009/0000624 A1 | 1/2009 | Lee et al. |
| 2009/0014007 A1 | 1/2009 | Brambilla et al. |
| 2009/0032024 A1 | 2/2009 | Burz et al. |

(56) References Cited

U.S. PATENT DOCUMENTS

| | | |
|---|---|---|
| 2009/0032026 A1 | 2/2009 | Price et al. |
| 2009/0044808 A1 | 2/2009 | Guney et al. |
| 2009/0044809 A1 | 2/2009 | Welchel et al. |
| 2009/0078267 A1 | 3/2009 | Burz et al. |
| 2009/0107504 A1 | 4/2009 | McAuley et al. |
| 2009/0114227 A1 | 5/2009 | Gunaratnam et al. |
| 2009/0120442 A1 | 5/2009 | Ho |
| 2009/0126739 A1 | 5/2009 | Ng et al. |
| 2009/0133697 A1 | 5/2009 | Kwok et al. |
| 2009/0139527 A1 | 6/2009 | Ng et al. |
| 2009/0145429 A1 | 6/2009 | Ging et al. |
| 2009/0151729 A1 | 6/2009 | Judson et al. |
| 2009/0173349 A1 | 7/2009 | Hernandez et al. |
| 2009/0178680 A1 | 7/2009 | Chang |
| 2009/0183734 A1 | 7/2009 | Kwok et al. |
| 2009/0183739 A1 | 7/2009 | Wondka |
| 2009/0211583 A1 | 8/2009 | Carroll |
| 2009/0223519 A1 | 9/2009 | Eifler et al. |
| 2009/0250060 A1 | 10/2009 | Hacke et al. |
| 2009/0320187 A1 | 12/2009 | Petzl et al. |
| 2010/0000538 A1 | 1/2010 | Edwards et al. |
| 2010/0000539 A1 | 1/2010 | Woodard |
| 2010/0000543 A1 | 1/2010 | Berthon-Jones et al. |
| 2010/0000544 A1 | 1/2010 | Blaszczykiewicz et al. |
| 2010/0018534 A1 | 1/2010 | Veliss et al. |
| 2010/0037897 A1 | 2/2010 | Wood |
| 2010/0051031 A1 | 3/2010 | Lustenberger et al. |
| 2010/0051034 A1 | 3/2010 | Howard |
| 2010/0083969 A1 | 4/2010 | Crumblin |
| 2010/0108072 A1 | 5/2010 | D'Souza |
| 2010/0132717 A1 | 6/2010 | Davidson et al. |
| 2010/0154798 A1 | 6/2010 | Henry et al. |
| 2010/0170516 A1 | 7/2010 | Grane |
| 2010/0199992 A1 | 8/2010 | Ho |
| 2010/0224199 A1 | 9/2010 | Smith et al. |
| 2010/0229868 A1 | 9/2010 | Rummery et al. |
| 2010/0229872 A1 | 9/2010 | Ho |
| 2010/0258132 A1 | 10/2010 | Moore |
| 2010/0258136 A1 | 10/2010 | Doherty et al. |
| 2010/0282265 A1 | 11/2010 | Melidis et al. |
| 2010/0294281 A1 | 11/2010 | Ho |
| 2010/0307502 A1 | 12/2010 | Rummery et al. |
| 2010/0313532 A1 | 12/2010 | Stjernfelt et al. |
| 2010/0313891 A1 | 12/2010 | Veliss et al. |
| 2010/0319700 A1 | 12/2010 | Ng et al. |
| 2010/0326445 A1 | 12/2010 | Veliss et al. |
| 2011/0048425 A1 | 3/2011 | Chang |
| 2011/0067704 A1 | 3/2011 | Kooij |
| 2011/0072553 A1 | 3/2011 | Ho |
| 2011/0088699 A1 | 4/2011 | Skipper |
| 2011/0126838 A1 | 6/2011 | Alberici |
| 2011/0146685 A1 | 6/2011 | Allan et al. |
| 2011/0197341 A1 | 8/2011 | Formica |
| 2011/0220113 A1 | 9/2011 | Newman |
| 2011/0232649 A1 | 9/2011 | Collazo et al. |
| 2011/0247628 A1 | 10/2011 | Ho |
| 2011/0259335 A1 | 10/2011 | Sullivan |
| 2011/0259337 A1 | 10/2011 | Hitchcock |
| 2011/0265791 A1 | 11/2011 | Ging et al. |
| 2011/0265796 A1 | 11/2011 | Amarasinghe et al. |
| 2011/0290253 A1 | 12/2011 | McAuley |
| 2012/0067349 A1 | 3/2012 | Barlow et al. |
| 2012/0125339 A1 | 5/2012 | Ho et al. |
| 2012/0132208 A1 | 5/2012 | Judson et al. |
| 2012/0132209 A1 | 5/2012 | Rummery |
| 2012/0138061 A1 | 6/2012 | Dravitzki et al. |
| 2012/0138063 A1 | 6/2012 | Eves et al. |
| 2012/0174355 A1 | 7/2012 | Fraze |
| 2012/0204879 A1 | 8/2012 | Cariola et al. |
| 2012/0222680 A1 | 9/2012 | Eves et al. |
| 2012/0247490 A1 | 10/2012 | Matthews |
| 2012/0285457 A1 | 11/2012 | Mansour et al. |
| 2012/0285464 A1 | 11/2012 | Birch et al. |
| 2012/0304999 A1 | 12/2012 | Swift et al. |
| 2012/0318265 A1 | 12/2012 | Amirav et al. |
| 2013/0000648 A1 | 1/2013 | Madaus et al. |
| 2013/0008449 A1 | 1/2013 | Busch et al. |
| 2013/0133659 A1 | 5/2013 | Ng et al. |
| 2013/0133664 A1 | 5/2013 | Startare |
| 2013/0139822 A1 | 6/2013 | Gibson |
| 2013/0152918 A1 | 6/2013 | Rummery et al. |
| 2013/0152937 A1 | 6/2013 | Jablonski |
| 2013/0160769 A1 | 6/2013 | Ng et al. |
| 2013/0220327 A1 | 8/2013 | Barlow et al. |
| 2013/0228173 A1 | 9/2013 | Busch |
| 2013/0247916 A1 | 9/2013 | Symons |
| 2013/0319421 A1 | 12/2013 | Hitchcock et al. |
| 2014/0026888 A1 | 1/2014 | Matula |
| 2014/0026890 A1 | 1/2014 | Haskard et al. |
| 2014/0083428 A1 | 3/2014 | Rothermel et al. |
| 2014/0083430 A1 | 3/2014 | Matula, Jr. et al. |
| 2014/0102456 A1 | 4/2014 | Ovizinsky |
| 2014/0137870 A1 | 5/2014 | Barlow |
| 2014/0158726 A1 | 6/2014 | Malara |
| 2014/0166019 A1 | 6/2014 | Ho et al. |
| 2014/0190486 A1 | 7/2014 | Dunn et al. |
| 2014/0209098 A1 | 7/2014 | Dunn |
| 2014/0216452 A1 | 8/2014 | Miller et al. |
| 2014/0261432 A1 | 9/2014 | Eves et al. |
| 2014/0305439 A1 | 10/2014 | Chodkowski |
| 2014/0311492 A1 | 10/2014 | Stuebiger et al. |
| 2014/0338672 A1 | 11/2014 | D'Souza et al. |
| 2014/0358054 A1 | 12/2014 | Capra |
| 2015/0000615 A1 | 1/2015 | Imran et al. |
| 2015/0005685 A1 | 1/2015 | Chetlapalli et al. |
| 2015/0028519 A1 | 1/2015 | Lang et al. |
| 2015/0033457 A1 | 2/2015 | Tryner et al. |
| 2015/0051000 A1 | 2/2015 | Henn |
| 2015/0090266 A1 | 4/2015 | Melidis et al. |
| 2015/0090268 A1 | 4/2015 | Madaus et al. |
| 2015/0128953 A1 | 5/2015 | Formica et al. |
| 2015/0151070 A1 | 6/2015 | Capra et al. |
| 2015/0190262 A1 | 7/2015 | Capra et al. |
| 2015/0202397 A1 | 7/2015 | Pastoor |
| 2015/0217150 A1 | 8/2015 | Harris |
| 2015/0246198 A1 | 9/2015 | Bearne et al. |
| 2015/0285337 A1 | 10/2015 | Dingley et al. |
| 2015/0290415 A1 | 10/2015 | Dunn |
| 2015/0335846 A1 | 11/2015 | Romagnoli et al. |
| 2015/0352308 A1 | 12/2015 | Cullen et al. |
| 2015/0374944 A1 | 12/2015 | Edwards et al. |
| 2016/0001028 A1 | 1/2016 | McAuley et al. |
| 2016/0008558 A1 | 1/2016 | Huddart et al. |
| 2016/0015922 A1 | 1/2016 | Chodkowski et al. |
| 2016/0022944 A1 | 1/2016 | Chodkowski et al. |
| 2016/0038707 A1 | 2/2016 | Allan et al. |
| 2016/0045700 A1 | 2/2016 | Amarasinghe |
| 2016/0051000 A1 | 2/2016 | Henn |
| 2016/0051786 A1 | 2/2016 | McAuley et al. |
| 2016/0082214 A1 | 3/2016 | Barlow et al. |
| 2016/0082217 A1 | 3/2016 | McClaren et al. |
| 2016/0144146 A1 | 5/2016 | Huddart et al. |
| 2016/0166793 A1 | 6/2016 | McLaren et al. |
| 2016/0178027 A1 | 6/2016 | Wetzel |
| 2016/0213873 A1 | 7/2016 | McAuley et al. |
| 2016/0213874 A1 | 7/2016 | Davidson et al. |
| 2016/0278463 A1 | 9/2016 | Stevenson |
| 2016/0296720 A1 | 10/2016 | Henry et al. |
| 2016/0375214 A1 | 12/2016 | Chodkowski et al. |
| 2017/0028148 A1 | 2/2017 | McAuley et al. |
| 2017/0136269 A1 | 5/2017 | Jacotey et al. |
| 2017/0143925 A1 | 5/2017 | McAuley et al. |
| 2017/0182276 A1 | 6/2017 | Hammer |
| 2017/0189636 A1 | 7/2017 | Gibson et al. |
| 2017/0216548 A1 | 8/2017 | Gerhardt |
| 2017/0239438 A1 | 8/2017 | McAuley et al. |
| 2017/0246411 A1 | 8/2017 | Mashal et al. |
| 2017/0304574 A1 | 10/2017 | McAuley et al. |
| 2017/0368288 A1 | 12/2017 | Stephens et al. |
| 2018/0214655 A1 | 8/2018 | Kooij et al. |
| 2018/0250483 A1 | 9/2018 | Olsen et al. |
| 2018/0256844 A1 | 9/2018 | Galgali et al. |
| 2018/0264218 A1 | 9/2018 | Chodkowski |
| 2018/0339123 A1 | 11/2018 | Smith et al. |

(56) References Cited

U.S. PATENT DOCUMENTS

| | | |
|---|---|---|
| 2019/0001095 A1 | 1/2019 | Rose et al. |
| 2019/0030273 A1 | 1/2019 | McAuley et al. |
| 2019/0083734 A1 | 3/2019 | Hammer et al. |
| 2019/0111227 A1 | 4/2019 | Veliss et al. |
| 2019/0117026 A1 | 4/2019 | Felix et al. |
| 2019/0151592 A1 | 5/2019 | Bornholdt |
| 2019/0232010 A1 | 8/2019 | McAuley et al. |
| 2020/0016357 A1 | 1/2020 | McAuley et al. |
| 2020/0046928 A1 | 2/2020 | Allan |
| 2020/0108219 A1 | 4/2020 | McAuley et al. |
| 2020/0129720 A1 | 4/2020 | McLaren et al. |
| 2020/0164169 A1 | 5/2020 | McAuley et al. |
| 2020/0197644 A1 | 6/2020 | McAuley et al. |
| 2020/0230343 A1 | 7/2020 | Sims et al. |
| 2020/0230344 A1 | 7/2020 | Huddart et al. |
| 2020/0268997 A1 | 8/2020 | McAuley et al. |
| 2020/0268998 A1 | 8/2020 | McAuley et al. |
| 2020/0338294 A1 | 10/2020 | McLaren et al. |
| 2021/0008316 A1 | 1/2021 | McLaren et al. |
| 2021/0016041 A1 | 1/2021 | Huddart et al. |
| 2022/0126049 A1 | 4/2022 | Amarasinghe |
| 2022/0331542 A1 | 10/2022 | McLaren et al. |
| 2023/0201510 A1 | 6/2023 | Hammer |
| 2023/0347090 A1 | 11/2023 | Huddart et al. |
| 2024/0024606 A1 | 1/2024 | McLaren et al. |
| 2024/0033461 A1 | 2/2024 | Felix et al. |
| 2024/0139456 A1 | 5/2024 | Freestone |
| 2024/0165360 A1 | 5/2024 | Smith et al. |
| 2024/0181194 A1 | 6/2024 | Hammer |

FOREIGN PATENT DOCUMENTS

| | | |
|---|---|---|
| CN | 2172538 | 7/1994 |
| CN | 2504493 Y | 8/2002 |
| CN | 1784250 | 6/2006 |
| CN | 1901963 A | 1/2007 |
| CN | 201033204 | 3/2008 |
| CN | 201171846 | 12/2008 |
| CN | 101432039 A | 5/2009 |
| CN | 100502972 C | 6/2009 |
| CN | 101516427 | 8/2009 |
| CN | 102753230 A | 10/2012 |
| CN | 202822396 U | 3/2013 |
| CN | 103536996 | 1/2014 |
| DE | 895692 | 11/1953 |
| DE | 2706284 | 8/1978 |
| DE | 3122034 | 12/1982 |
| DE | 3907428 | 9/1990 |
| DE | 10254399 | 6/2004 |
| DE | 102006011151 | 9/2007 |
| EP | 0 350 322 | 1/1990 |
| EP | 0 401 307 | 8/1995 |
| EP | 0 879 565 | 11/1998 |
| EP | 0 982 049 | 3/2000 |
| EP | 1 187 650 | 12/2005 |
| EP | 2 130 563 | 12/2009 |
| EP | 2 327 443 A2 | 6/2011 |
| EP | 2 517 757 | 10/2012 |
| EP | 2 022 528 | 3/2016 |
| FR | 2390116 | 3/1938 |
| FR | 2618340 | 11/1970 |
| FR | 825960 | 1/1989 |
| FR | 2658725 | 8/1991 |
| FR | 2749176 | 12/1997 |
| FR | 2804421 | 8/2001 |
| GB | 190224431 | 12/1902 |
| GB | 339522 | 12/1930 |
| GB | 826198 | 12/1959 |
| GB | 880824 | 10/1961 |
| GB | 1467828 | 3/1977 |
| GB | 2133275 | 7/1984 |
| GB | 2188236 | 9/1987 |
| GB | 1211268 | 4/2000 |
| GB | 2478305 | 9/2011 |
| GB | 2491227 | 11/2012 |
| GB | 2553475 | 3/2018 |
| JP | S46-12114 | 4/1971 |
| JP | 46-016719 | 6/1971 |
| JP | S55-89072 | 7/1980 |
| JP | 2004-016488 | 1/2004 |
| JP | 2003-053874 | 9/2004 |
| JP | 2009-125306 | 6/2009 |
| JP | 2010-090973 | 4/2010 |
| JP | 2000-102624 | 5/2013 |
| JP | 2018-127729 | 8/2018 |
| KR | 10-2011-0028950 | 3/2011 |
| NZ | 585295 | 12/2011 |
| WO | WO 95/12432 | 5/1995 |
| WO | WO 97/32494 | 9/1997 |
| WO | WO 98/003225 | 1/1998 |
| WO | WO 98/018514 | 5/1998 |
| WO | WO 99/04842 | 2/1999 |
| WO | WO 99/058181 | 11/1999 |
| WO | WO 00/50122 | 8/2000 |
| WO | WO 00/069497 | 11/2000 |
| WO | WO 00/074758 | 12/2000 |
| WO | WO 01/041854 | 6/2001 |
| WO | WO 01/097892 | 12/2001 |
| WO | WO 02/44749 | 6/2002 |
| WO | WO 02/047749 | 6/2002 |
| WO | WO 02/074372 | 9/2002 |
| WO | WO 04/041341 | 5/2004 |
| WO | WO 04/073778 | 9/2004 |
| WO | WO 05/021075 | 3/2005 |
| WO | WO 05/032634 | 4/2005 |
| WO | WO 05/046776 | 5/2005 |
| WO | WO 05/051468 | 6/2005 |
| WO | WO 05/063328 | 7/2005 |
| WO | WO 05/123166 | 12/2005 |
| WO | WO 06/130903 | 12/2006 |
| WO | WO 06/138416 | 12/2006 |
| WO | WO 07/022562 | 3/2007 |
| WO | WO 07/041786 | 4/2007 |
| WO | WO 07/068044 | 6/2007 |
| WO | WO 07/125487 | 11/2007 |
| WO | WO 07/147088 | 12/2007 |
| WO | WO 08/007985 | 1/2008 |
| WO | WO 08/060295 | 5/2008 |
| WO | WO 08/070929 | 6/2008 |
| WO | WO 08/106716 | 9/2008 |
| WO | WO 08/148086 | 12/2008 |
| WO | WO 09/026627 | 3/2009 |
| WO | WO 09/038918 | 3/2009 |
| WO | WO 09/052560 | 4/2009 |
| WO | WO 09/059353 | 5/2009 |
| WO | WO 09/092057 | 7/2009 |
| WO | WO 09/108995 | 9/2009 |
| WO | WO 09/139647 | 11/2009 |
| WO | WO 09/148956 | 12/2009 |
| WO | WO 10/066004 | 6/2010 |
| WO | WO 10/081295 | 7/2010 |
| WO | WO 10/131189 | 11/2010 |
| WO | WO 10/139014 | 12/2010 |
| WO | WO 11/072739 | 6/2011 |
| WO | WO 11/077254 | 6/2011 |
| WO | WO 12/07300 | 1/2012 |
| WO | WO 12/045127 | 4/2012 |
| WO | WO 12/069951 | 5/2012 |
| WO | WO 12/071300 | 5/2012 |
| WO | WO 12/143822 | 10/2012 |
| WO | WO 12/154883 | 11/2012 |
| WO | WO 12/177152 | 12/2012 |
| WO | WO 13/006913 | 1/2013 |
| WO | WO 13/026091 | 2/2013 |
| WO | WO 13/026092 | 2/2013 |
| WO | WO 13/064930 | 5/2013 |
| WO | WO 14/020469 | 2/2014 |
| WO | WO 14/025267 | 2/2014 |
| WO | WO 14/031673 | 2/2014 |
| WO | WO 14/075141 | 5/2014 |
| WO | WO 14/077708 | 5/2014 |
| WO | WO 14/110622 | 7/2014 |
| WO | WO 14/110626 | 7/2014 |
| WO | WO 14/129913 | 8/2014 |

(56) References Cited

FOREIGN PATENT DOCUMENTS

| WO | WO 14/175752 | 10/2014 |
|----|--------------|---------|
| WO | WO 14/175753 | 10/2014 |
| WO | WO 15/033287 | 3/2015 |
| WO | WO 15/070289 | 5/2015 |
| WO | WO 15/079396 | 6/2015 |
| WO | WO 15/083060 | 6/2015 |
| WO | WO 15/151019 | 10/2015 |
| WO | WO 15/187986 | 12/2015 |
| WO | WO 16/043603 | 3/2016 |
| WO | WO 17/030447 | 2/2017 |
| WO | WO 17/059476 | 4/2017 |
| WO | WO 17/150990 | 9/2017 |
| WO | WO 17/158474 | 9/2017 |
| WO | WO 17/158544 | 9/2017 |
| WO | WO 17/160166 | 9/2017 |
| WO | WO 17/216708 | 12/2017 |
| WO | WO 19/003094 | 1/2019 |

OTHER PUBLICATIONS

Pad A Cheek, LLC, Sleep apnea can make beautiful sleep elusive, (http://web.archive.org/web/20070701000000*/http://www.padacheek.com/;Wayback Machine), downloaded Feb. 24, 2020, 3 pp.

Philips Respironics 'System One Heated Humidifier—User Manual', 2011, pp. 1-16, [retrieved on Nov. 25, 2013] from the internet: URL: http://www.cpapxchange.com/cpap-machines-biap-machines/system-one-60-series-cpap-humidifier-manual.pdf.

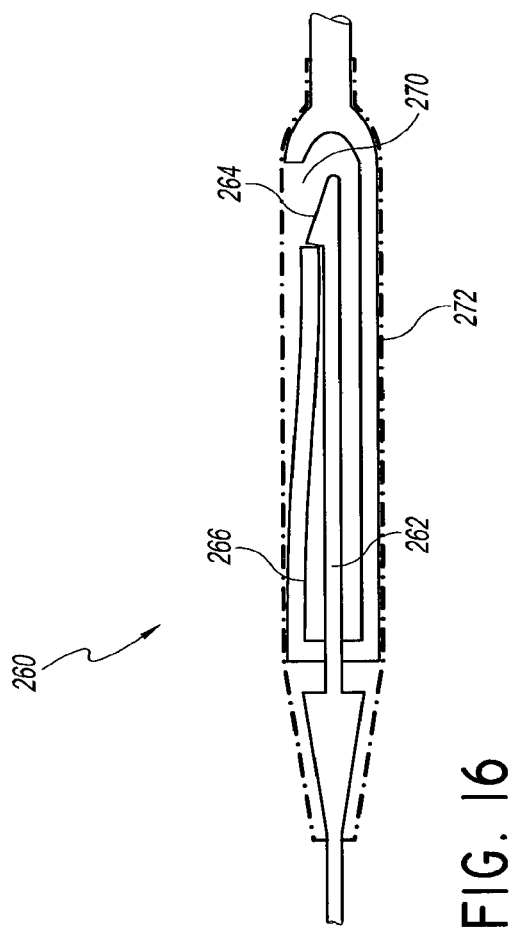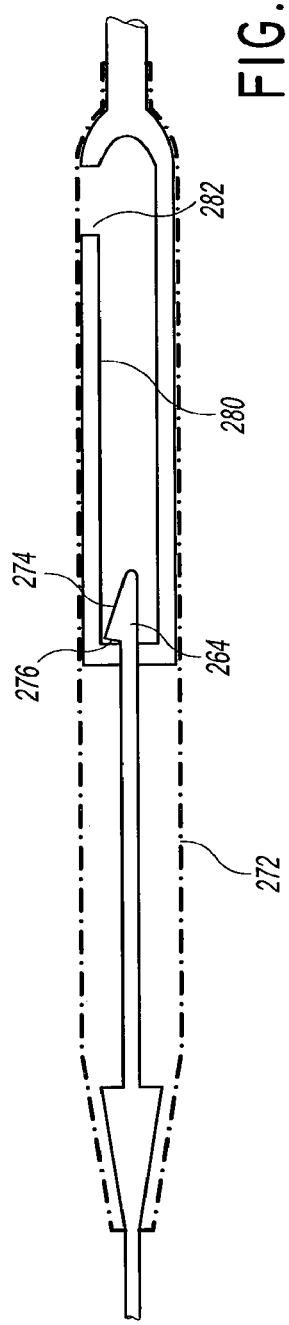

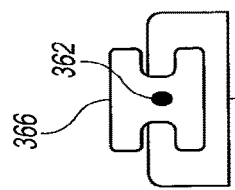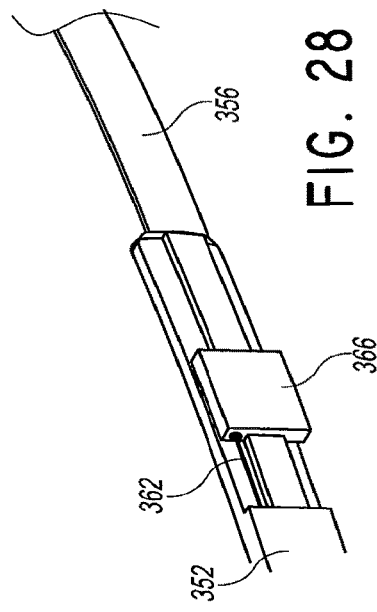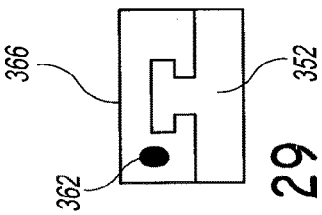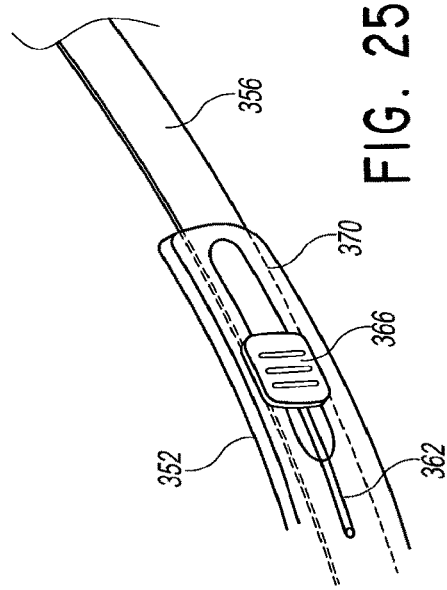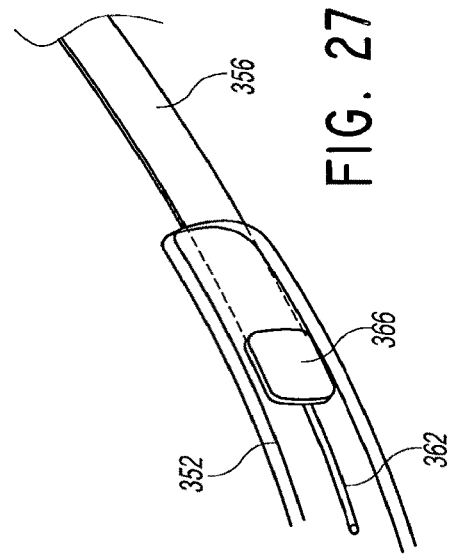

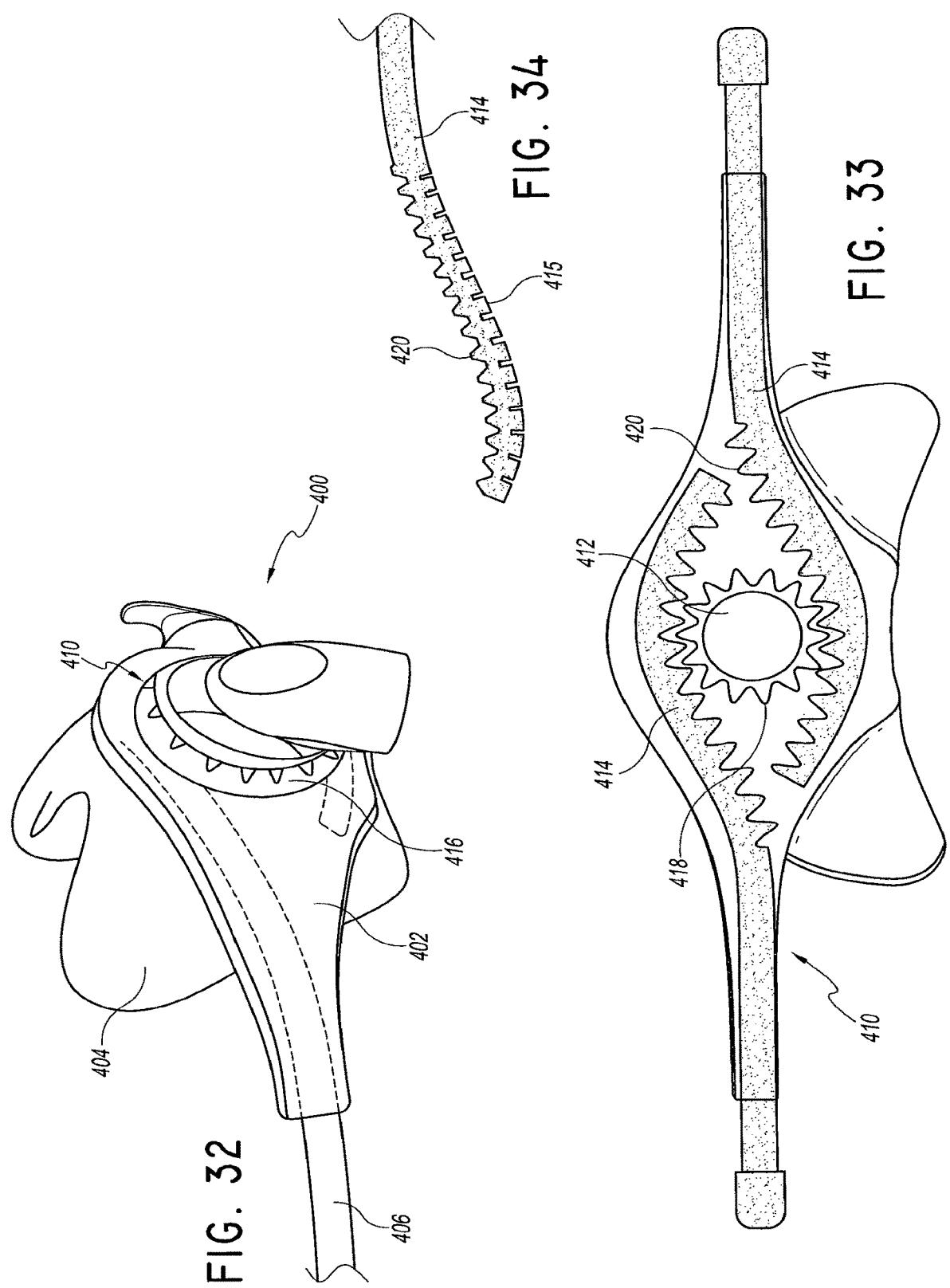

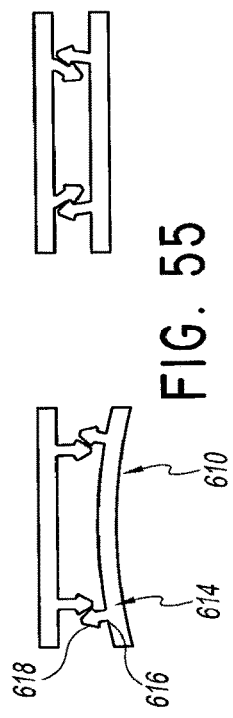
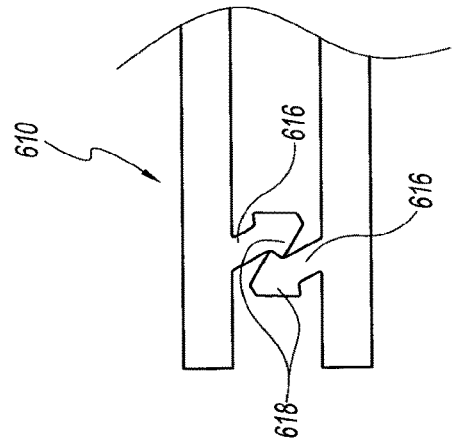
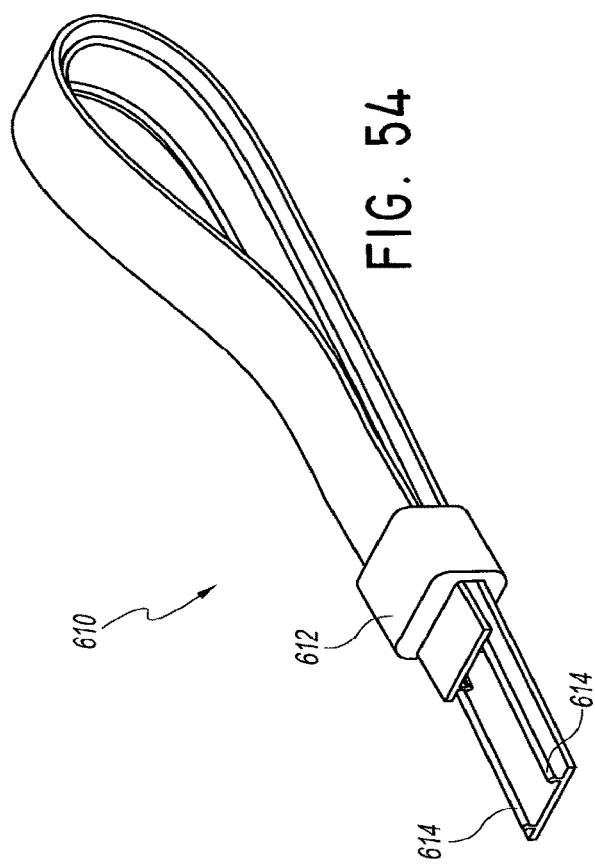
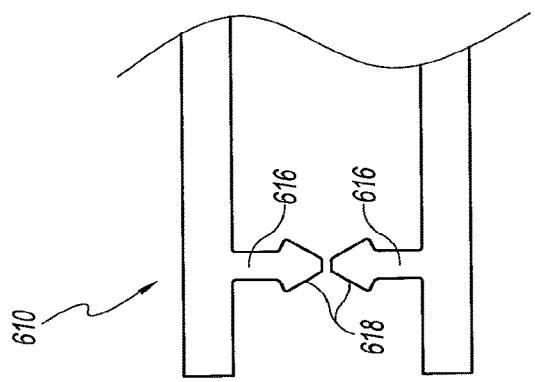

HEADGEAR FOR PATIENT INTERFACE

INCORPORATION BY REFERENCE TO ANY PRIORITY APPLICATIONS

Any and all applications for which a foreign or domestic priority claim is identified in the Application Data Sheet as filed with the present application are hereby incorporated by reference and made a part of the present disclosure.

BACKGROUND OF THE INVENTION

Field of the Invention

The present invention generally relates to masks that cover a breathing passage and structures used to secure the masks to the head. More particularly, the present invention relates to generally non-stretch structures that have at least one of an adjustment mechanism and a configuration providing a predetermined wearing length and a longer length for donning.

Description of the Related Art

Obstructive sleep apnea (OSA) is a sleep condition in which the back of the throat relaxes so much while sleeping that it narrows the airway or even entirely blocks the airway. With the constriction or closure of the airway, breathing can stop or become very shallow for a few seconds or longer.

Continuous positive airway pressure (CPAP) is used to treat OSA. CPAP sends a flow of pressurized air that splints open the airway. The flow of pressurized air can be delivered to the user with an interface. The interface can include a mask and headgear, such as an elastic strap.

When donning the interface, the elastic strap is stretched to allow the headgear to slide over the head of the user. When released, the elastic strap tends to pull the interface against the face of the user.

As the pressure within the mask increases (e.g., 4 cm $H_2O$ to 12 cm $H_2O$), the mask attempts to move away from the face of the user because the strap securing the mask against the face is elastic. In some masks, when the force moving the mask away from the face of the user causes the elastic strap to stretch, the force exerted by the mask against the face of the user decreases. Thus, as pressures increase, leaks can result in those masks and, if suitably sealed at higher pressures (e.g., 12 cm $H_2O$), the elasticity of the strap causes undesirably high pressures to be exerted against the face of the user at lower treatment pressures (e.g., 4 cm $H_2O$).

SUMMARY OF THE INVENTION

An object of the present invention is to provide an interface which will at least provide the industry and users with useful choice.

Some aspects of the present invention relate to headgear for use with an interface where the headgear is generally inelastic. Generally inelastic headgear is believed by the inventors to be superior to elastic headgear when used with pressures that vary dramatically over a treatment session, for example. However, generally inelastic headgear can be difficult to fit and use. For example, with generally inelastic headgear, there is a need for decoupling the headgear during donning, which can be problematic when it comes to adjusting the headgear for proper fit. Decoupling also can be difficult to manage for some users.

Certain features, aspects and advantages of the present invention relate to an interface assembly for use in providing a breathing treatment. The interface assembly can comprise a mask. The mask comprises a frame and a seal supported by the frame. Headgear can be connected to the mask and at least one of (i) an adjustment mechanism configured to be set to a use length for a loop defined by the mask and the headgear; and (ii) a break-fit assembly configured to selectively lengthen the loop defined by the mask and the headgear when a predetermined force has been exceeded and return to the use length when the predetermined force has not been exceeded.

In some such configurations, the interface assembly comprises both the adjustment mechanism and the break-fit assembly. In some such configurations, the adjustment mechanism couples the headgear to the mask. In some such configurations, the adjustment mechanism is positioned on the mask. In some such configurations, the adjustment mechanism is positioned on the headgear.

In some such configurations, the break-fit assembly joins the headgear and the mask. In some such configurations, the break-fit assembly joins the adjustment mechanism and the mask. In some such configurations, the break-fit assembly joins the adjustment mechanism and the headgear. In some such configurations, the break-fit assembly is positioned on the frame of the mask. In some such configurations, the break-fit assembly is positioned on the headgear.

In some such configurations, the break-fit assembly comprises a magnetic coupling.

In some such configurations, the break-fit assembly comprises a mechanical coupling.

In some such configurations, the adjustment mechanism is positioned on the mask. In some such configurations, the adjustment mechanism comprises a squeeze to lock mechanism. In some such configurations, the adjustment mechanism comprises a squeeze to unlock mechanism.

In some such configurations, the break-fit assembly comprises a biasing member. In some such configurations, the biasing member comprises an elastic sleeve. In some such configurations, the biasing member comprises a spring.

In some such configurations, the headgear is substantially nonstretch.

Certain features, aspects and advantages of the present invention relate to a mask and headgear system comprising a mask and headgear. The mask comprises a frame and a seal supported by the frame. The headgear can be connected to the mask. A break-fit assembly can be configured to elongate upon the application of a force exceeding a preselected force. The mask, headgear, and break-fit assembly together define a loop that elongates with forces that exceed the preselected force.

In some such configurations, upon application of the force exceeding the preselected force, the resulting elongation of the loop is sufficient to allow a user to don and position the mask on the user's head and face or to allow the user to remove the interface from the user's head and face. In some such configurations, the break-fit assembly resists elongation and remains connected in general use if a force less than the preselected force is applied.

Certain features, aspects and advantages of the present invention relate to a break-fit assembly for a mask and headgear assembly. The break-fit assembly comprises a mechanical coupling that resists elongation from a first length to a second length until a force is applied that exceeds a predetermined force. The mechanical coupling comprising multiple parts and a stretch biasing member that connects two or more of the multiple parts.

In some such configurations, the stretch biasing member exhibits at least one of the following: (1) elastic characteristics and (2) spring characteristics. In some such configurations, the stretch biasing member provides a connection between the parts of the mechanical coupling of the break-fit assembly. In some such configurations, the mechanical coupling requires a first force to disconnect and second force to reconnect, the second force being less than the first force.

Certain features, aspects and advantages of the present invention relate to a break-fit assembly for a mask and headgear assembly. The break-fit assembly comprises a magnetic coupling that resists elongation from a first length to a second length until a force is applied that exceeds a predetermined force. The magnetic coupling comprising multiple parts and a stretch portion.

In some such configurations, the magnetic coupling fulfills a biasing function for the break-fit assembly. In some such configurations, the stretch portion provides a connection between two or more parts of the magnetic coupling.

Certain features, aspects and advantages of the present invention relate to a mask and headgear system comprising a mask configured to be positioned on a user's face and an adjustment mechanism configured to adjust the size of the headgear to accommodate different users.

In some such configurations, the headgear comprises a material that is substantially non-elastic. In some such configurations, the headgear is substantially non-stretch. In some such configurations, the adjustment mechanism comprises a buckle. In some such configurations, the buckle comprises a hook and loop fastener. In some such configurations, the adjustment mechanism comprises a reel and coil spring. In some such configurations, the adjustment mechanism includes a winding mechanism, a spool connected to the winding mechanism, and a flexible material band configured to be wound onto the spool.

The term "comprising" as used in the specification and claims means "consisting at least in part of". When interpreting a statement in this specification and claims that includes "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

Various forms of the interface will be described with reference to the accompanying drawings.

FIG. 16 is a top sectioned view of a break-fit assembly that is arranged and configured in accordance with certain features, aspects and advantages of the present invention.

FIG. 17 is another top sectioned view of the break-fit assembly of FIG. 16.

FIG. 25 is a partial view of a portion of the interface of FIG. 24.

FIG. 26 is a sectioned view of a portion of the portion of FIG. 25.

FIG. 27 is a partial view of a portion of the interface of FIG. 24.

FIG. 28 is a partial view of a portion of the interface of FIG. 24.

FIG. 29 is a sectioned view of a portion of the portion of FIG. 28.

FIG. 32 is a perspective view of an interface with an adjustment mechanism that is arranged and configured in accordance with certain features, aspects and advantages of the present invention.

FIG. 33 is a schematic view of the interface of FIG. 32.

FIG. 34 is a view of a portion of the adjustment mechanism of FIG. 32.

FIG. 54 is a perspective view of a strap having an adjustment mechanism.

FIG. 55 is a pair of cross-sectional views of the strap of FIG. 54.

FIG. 56 is a pair of enlarged cross-sectional views of the strap of FIG. 54.

DETAILED DESCRIPTION OF THE PREFERRED EMBODIMENT

Figure 1:
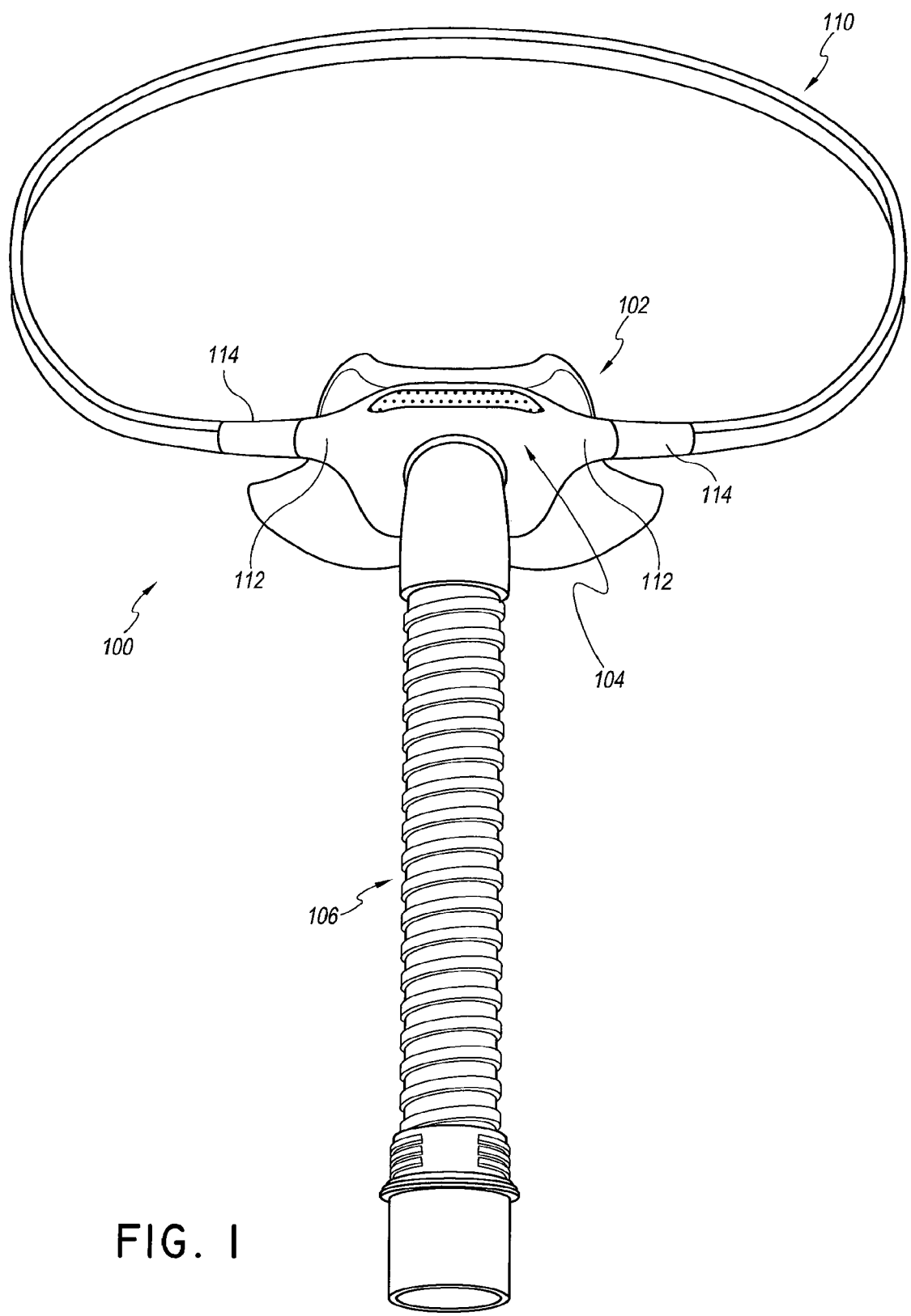
FIG. 1 is a front view of an interface that is arranged and configured in accordance with certain features, aspects and advantages of the present invention.
Figure 2:
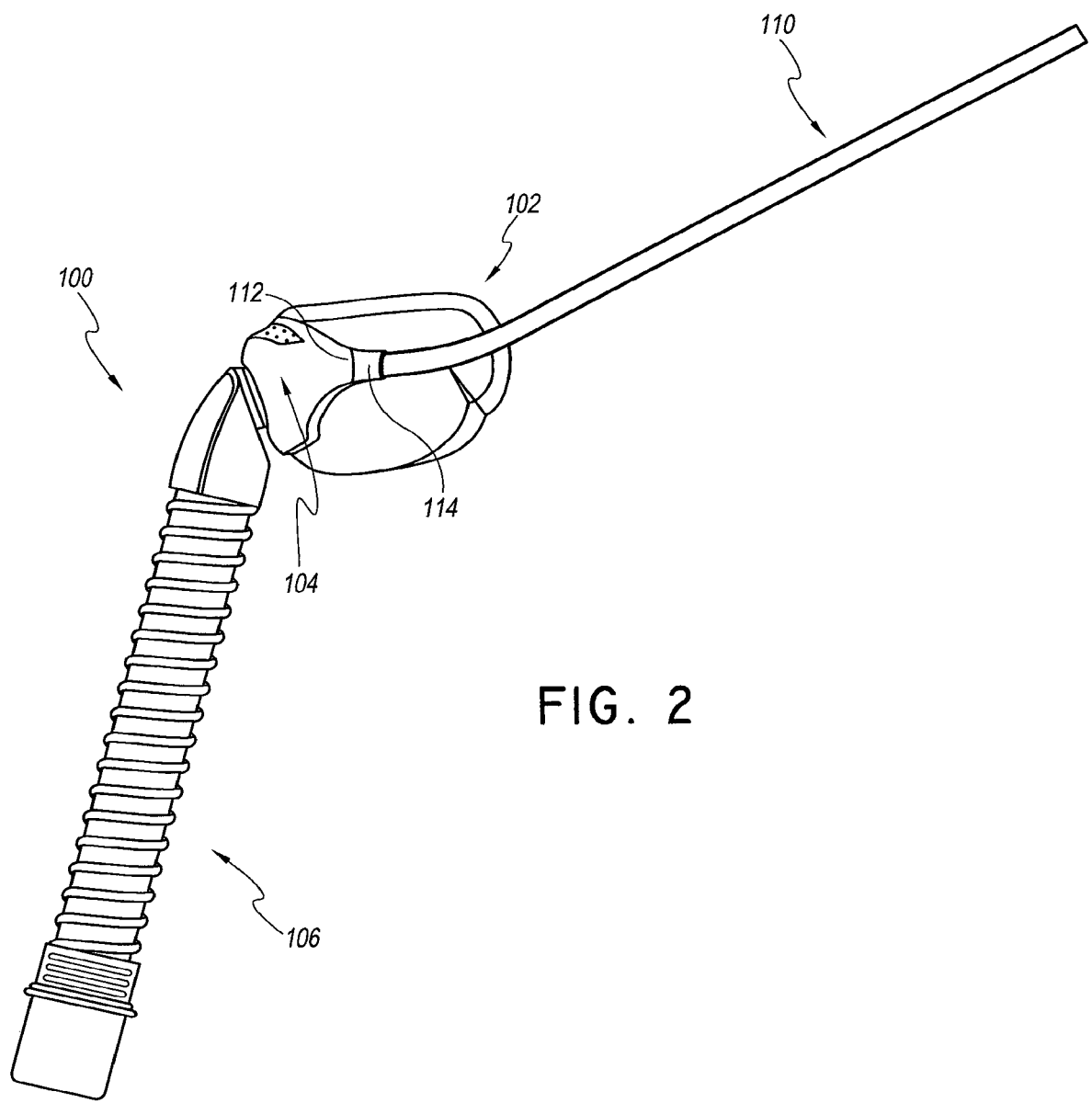
FIG. 2 is a side view of the interface of FIG. 1.

An example of an interface 100 is shown in FIGS. 1 and 2. The illustrated interface 100 comprises a seal 102 that is supported by a frame 104. A conduit 106 connects to at least one of the seal 102 and the frame 104. The conduit 106 can supply breathing gases to a user.

With reference still to FIGS. 1 and 2, headgear 110 connects to at least one of the seal 102 and the frame 104. In the arrangement illustrated in FIGS. 1 and 2, the headgear 110 comprises a single strap that extends around a head of the user. The frame 104 can comprise two mounting points 112 and the strap 110 comprises cooperating mounting members 114. In some configurations, the seal 102 can comprise the mounting points 112. Any suitable mounting points 112 and mounting members 114 can be used. The cooperating points 112 and members 114 facilitate easy connection and disconnection of the mounting points 112 and mounting members 114. In some configurations, in addition to anchoring the headgear 110, at least one of the mounting points 112 and/or the mounting members 114 comprises a suitable mechanism for adjusting a length of the headgear 110.

The illustrated headgear 110, as described above, can be a single strap 110 that passes around the back of the head. To improve stability, the strap 110 can bifurcate near the mounting members 114 such that multiple mounting points 112 and multiple mounting members 114 can be used.

To provide a consistent experience for the user at varying treatment pressures, the headgear 110 preferably is substantially completely nonstretch. For example, the headgear 110 can be formed of a generally inelastic material or can comprise at least one generally inelastic component that extends generally from one of the mounting members 114 to the other of the mounting members 114. In some configurations, the headgear exhibits limited or no substantial creep. In other words, the headgear 110 can remain substantially the same length over its useful life; the material preferably does not shrink or stretch to a significant degree. By way of example but without limitation, suede is a material that is generally inelastic and that exhibits limited or no creep.

Surprisingly, a generally inelastic headgear assembly (e.g., headgear capable of elastic elongation of less than about 1 percent at a force of about or less than about 5 newtons) has been found to improve user comfort and seal performance over elastic headgear. The generally inelastic headgear 110 does not elongate as a treatment pressure increases or varies over the course of treatment. Rather, the headgear simply reacts to oppose any forces generated by the seal during use. As such, when adjusted for a proper fit at high treatment pressures, the user does not experience too tight of a fit when the pressure decreases to a lower treatment pressure. Moreover, with the headgear adjusted and ready for use, the user generally experiences limited or no preload prior to starting a treatment pressure.

With the generally inelastic headgear 110, the headgear 110 preferably comprises a manner of adjusting a length of the loop defined by the interface 100 (e.g., the headgear 110 and the frame 104 in FIGS. 1 and 2). Many manners of adjusting the length will be described in more detail below. The adjustability facilitates customizing a fit of the inelastic headgear 110 to the particular physical anatomy of the user.

With the generally inelastic headgear 110, the headgear 110 preferably comprises a break-fit assembly. The break-fit assembly, many configurations of which will be described below, facilitates donning of the interface 100. The break-fit assembly can facilitate slight and controlled elongation of the loop defined by the interface 100 to allow the loop to expand sufficiently to slide into position around the head of the user. The extra length enables the user to pull the interface over the maximum circumference of the head while moving the headgear into position below and behind the maxima occipitus, for example. In some embodiments, the break-fit assembly provides between about 0 and 200 mm of expansion. This may be in one location or split over both sides of the associated interface.

The break-fit assembly also preferably will return to the original position, or a use length, once the interface 100 has been properly donned. In some configurations, the break-fit assembly will return automatically once the interface 100 has been donned.

The seal 102 and the frame 104 generally define a mask in the illustrated configuration. When breathing gases are supplied through the conduit 106 to a cavity defined within the mask, a lifting force is generated by the mask and the mask attempts to move away from the face of the user.

The headgear 110 opposes the lifting force. As described above, the break-fit assembly allows elongation of the loop defined by the interface 100 (e.g., by temporarily increasing a length of the strap). The break-fit assembly preferably only elongates after a break-free force has been applied to the assembly. The break-free force is greater than a maximum of the lifting force (i.e., a maximum of the lifting force generated at the highest expected treatment force). In some configurations, the break-free force is about 3 Newtons to about 8 Newtons.

As described above, the headgear 110 also can have a manner of adjusting the length of the loop. In some configurations, the length adjustment requires an adjustment force that is greater than the break-free force. In such configurations, to adjust the length, a force greater than that required to operate the break-fit assembly is required. As such, the adjustment force is greater than the break-free force and the break-free force is greater than the maximum lifting force. The adjustment force also is greater than the maximum lifting force, which can be particularly relevant if a break-fit assembly is not used.

While the above-description has been generally directed to the assembly of FIGS. 1-2, the description of the materials and relative forces preferably applies to any assembly in which either or both of a break-fit assembly and an adjustment configuration have been provided. In addition, any combination of masks, break-fit assemblies and adjustment configurations described herein is possible, is specifically contemplated and should be understood to be within the scope of this disclosure and certain features, aspects and advantages of this invention.

Figure 3:
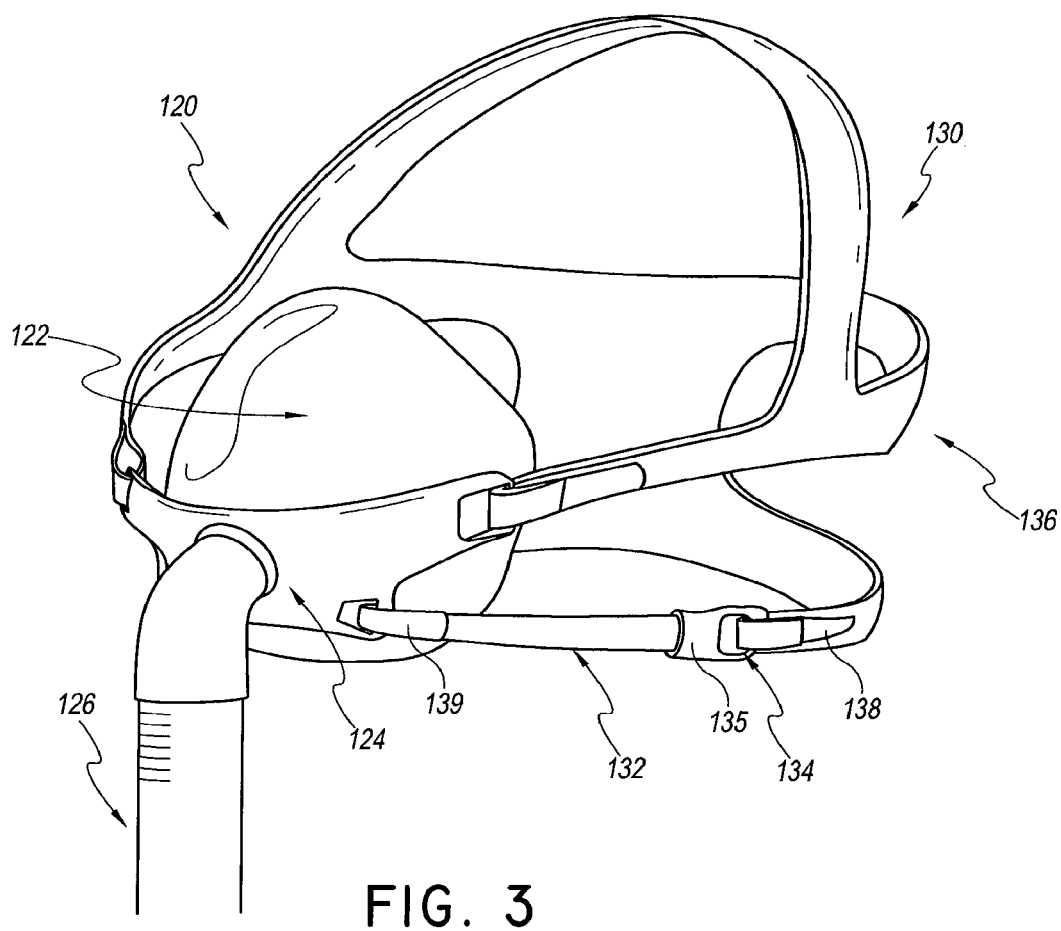
FIG. 3 is a perspective view of another interface that is arranged and configured in accordance with certain features, aspects and advantages of the present invention.

With reference to FIG. 3, another interface 120 is illustrated therein. The interface 120 also comprises a seal 122, a frame 124, a conduit 126 and headgear 130. While the interface 100 of FIGS. 1 and 2 was a nasal interface, the interface 120 of FIG. 3 is a full face interface. Certain features, aspects and advantages of the present invention can be used with any style of interface, including but not limited to nasal, oral, oral-nasal, full face, or the like.

The illustrated headgear 130 comprises a break-fit assembly 132 and an adjustment mechanism 134. The break-fit assembly 132 is shown in connection with only the lower straps but the break-fit assembly 132 also could be used on any and/or all of the straps if desired. While both the break-fit assembly 132 and the adjustment mechanism 134 are shown integrated into the interface, it also is possible to incorporate only one of the break-fit assembly 132 and the adjustment mechanism 134 into the interface. Moreover, any suitable break-fit assembly and/or any suitable adjustment mechanism can be used.

The headgear 130 preferably comprises a generally inelastic portion 136, the break-fit assembly 132 to facilitate donning of the interface 120, and the adjustment mechanism 134 to allow customization of the headgear 130 to the individual user. In some configurations, the headgear 130 comprises Breathoprene with a nonstretch component added to it. For example, the material could be a three layer laminate (i.e., foam, UBL (unbroken loop) and a nonstretch layer). In some configurations, a nonstretch layer can be a center layer of a five or more layer laminate: nonstretch as a central layer with foam and UBL on each side.

Figure 4:
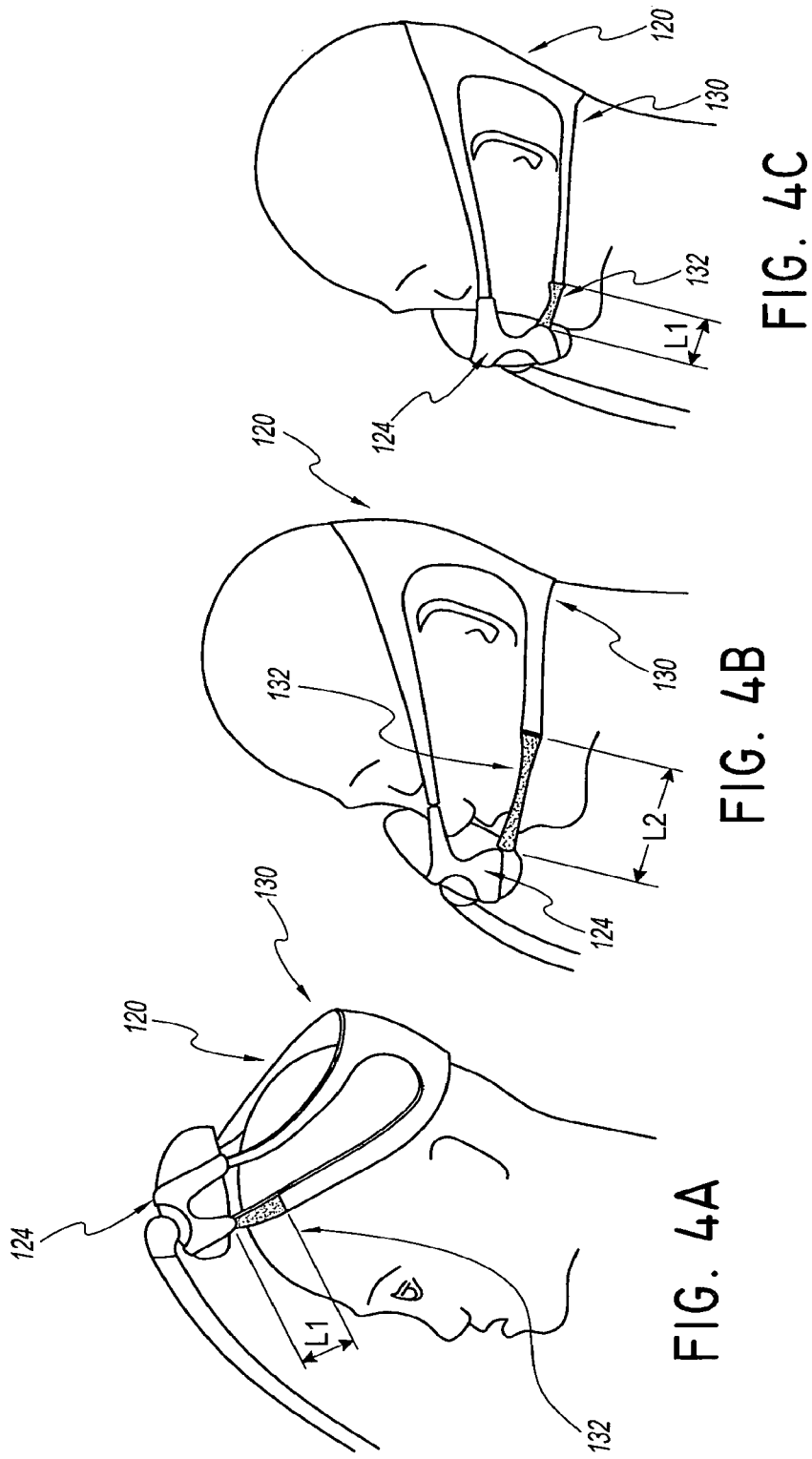
FIG. 4A is a schematic side elevation view of a first step of the process of donning the interface of FIG. 3 to a user.
FIG. 4B is a schematic side elevation view of a second step of the process of donning the interface of FIG. 3 to a user.
FIG. 4C is a schematic side elevation view of a third step of the process of donning the interface of FIG. 3 to a user.

With reference now to FIG. 4, the interface 130 is shown being donned by a user. As shown, the break-fit assembly 132 can extend from a first length L1 to a second length L2, which is greater than the first length L1. By extending from L1 to L2, the size of the loop defined by the headgear 130 and the frame 124 can be increased. By increasing the size of the loop, the loop can be sized to a desired size for normal use yet be extensible to a second larger size for donning without upsetting the ability to immediately return to the desired size for normal use.

Figure 5:
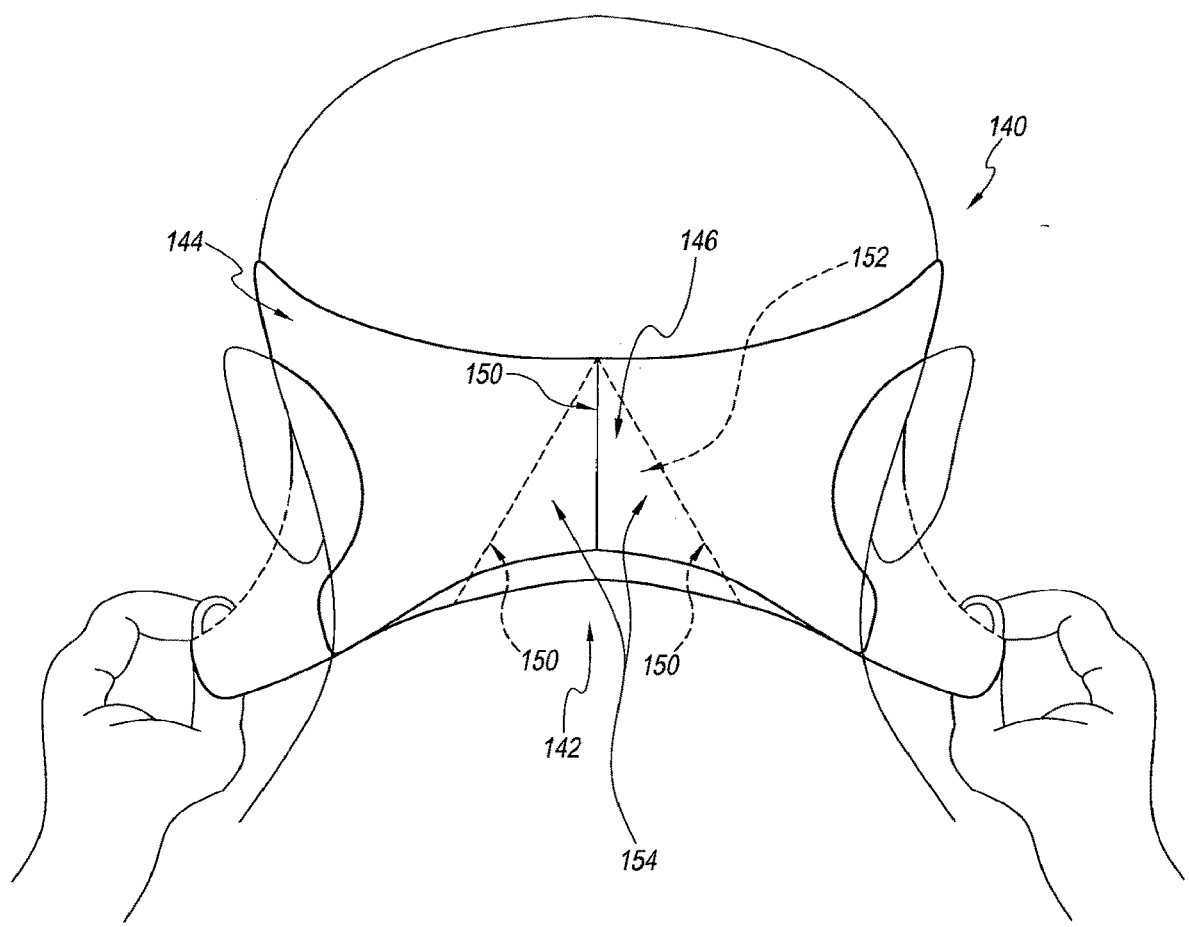
FIG. 5 is a rear view of headgear that is arranged and configured in accordance with certain features, aspects and advantages of the present invention.

FIG. 5 illustrates headgear 140 in which a break-fit assembly 142 is shown on another portion of the headgear relative to the configuration shown in FIG. 4. In FIG. 5, the break-fit assembly 142 is positioned on a rear portion of the headgear 140 while, in FIG. 4, the break-fit assembly 132 is positioned between the generally inelastic portion 136 (seen in FIG. 3) of the headgear 130 and the frame 124. Thus, the break-fit assembly can be positioned between the generally inelastic portion of the headgear and the frame as in FIG. 3, for example, or the inelastic portion of the headgear can be positioned between the break-fit assembly and the frame. In some configurations, the break-fit assembly can be integrated into the headgear (e.g., FIGS. 3 and 5).

With reference to FIG. 5 still, the headgear 140 comprises a generally inelastic portion 144. A coupling portion 146, several different embodiments of which will be described in detail below, can be positioned along a separable seam 150. The seam 150 can be temporarily joined together by the coupling portion 146. In other words, the seam 150 is defined by two edges (shown in dashed lines) that can be separated but, when in close proximity, the two edges are joined by the coupling portion 146. In some configurations, the coupling portion 146 comprises one or more magnets. For example, two magnets or one magnet and one magnetizable component (e.g., an iron component) can be used.

With continued reference to FIG. 5, a return component 152 can be integrated into the headgear 140. In the illustrated configuration, the return component 152 can comprise an elastic material. The return component 152 can span a gap that otherwise would exist between two flaps 154 that reside to each side of the seam 150. As such, when the gap is increased by pulling the headgear 140 (see dashed lines) and separating the flaps 154, the return component 152 can stretch to allow donning of the headgear 140. When the headgear 140 is released, the return component 152 can act to restore the headgear 140 to a position in which the flaps 154 can approach each other and the coupling portion 146 can join the flaps 154 along the seam 150.

In the illustrated configuration, the return component 152 comprises an elastic layer. For example, the return component 152 can comprise one or more portion formed of Lycra, rubber bands, and elastic knit. The elastic layer preferably can stretch up to about 40 mm when subjected to a tensile force of about 5 N (values may differ for a larger mask, such as a full-face mask). In some arrangements, rather than a full layer, the return component 152 can comprise strips, cords, bands or the like.

In the illustrated configuration, the coupling portion 146 comprises two components that are positioned at a lower portion of the headgear 140. Such a location is desired because it is less likely to be felt when sleeping in the headgear 140. Other locations are possible. In addition, while only two components are shown, more than two components are possible. In some configurations, the full length of the seam 150, a substantial portion of the full length of the seam 150 or a majority of the full length of the seam 150 can be formed of a magnetic material or the like such that the coupling portion 146 also can assist in pulling the seam 150 back together.

In some configurations, the break-fit assembly can be integrated into the frame and/or the seal. For example, with reference to FIGS. 6 through 8, an interface 160 has a frame 162 that incorporates a break-fit assembly 164. Thus, the break-fit assembly 164 shown in FIGS. 6 through 8 has been integrated into the mask (e.g., the frame of the mask).

Figure 6:
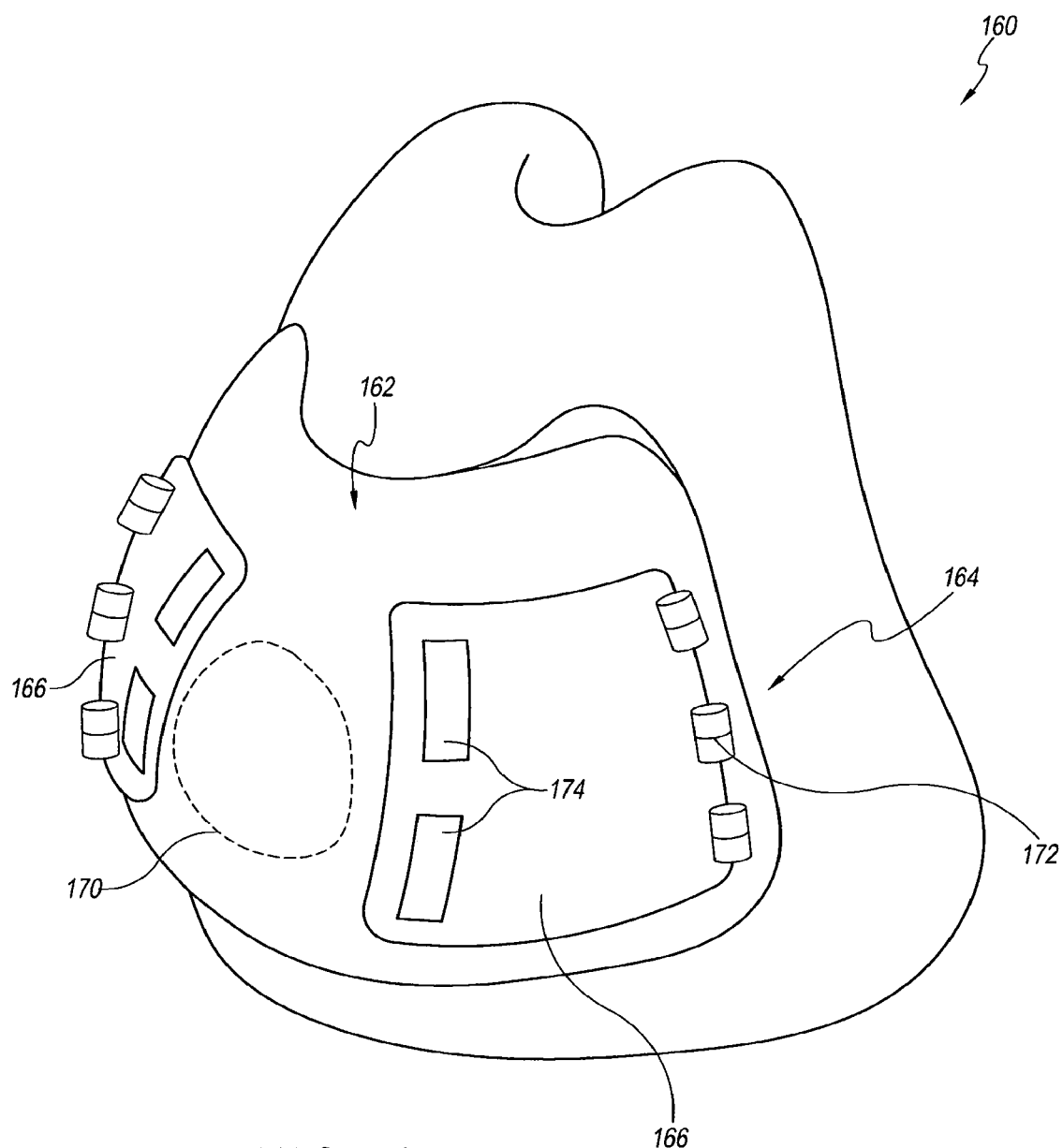
FIG. 6 is a perspective view of another interface that is arranged and configured in accordance with certain features, aspects and advantages of the present invention.

With continued reference to FIG. 6, the break-fit assembly 164 can have one or more flaps 166. The flaps 166 can seat against an outer surface 170 of the frame 162. As illustrated, the flaps 166 can be connected to the frame 162 with hinges 172. The illustrated flaps 166 can be connected to the frame 162 with one or more hinges; three hinges 172 are used in the illustrated interface 160. In some configurations, biasing members, such as springs or the like, can be used to provide a biasing force that will tend to return the flaps 166 to a closed or latched position, which position is described below.

Any suitable manner of holding the flaps 166 in position relative to the outer surface 170 of the frame 162 also can be used. In the illustrated configuration, a magnetic coupling 174 has been used. For example, the illustrated magnetic coupling 174 comprises at least one magnet and at least one corresponding component from a magnetic material; the illustrated configuration comprises two magnets and two corresponding components from magnetic materials on each flap 166. For the coupling 174 to function, each paired component comprises at least one magnet and at least one component formed of a magnetic material (e.g., a material that is attracted to a magnet).

Figure 7:
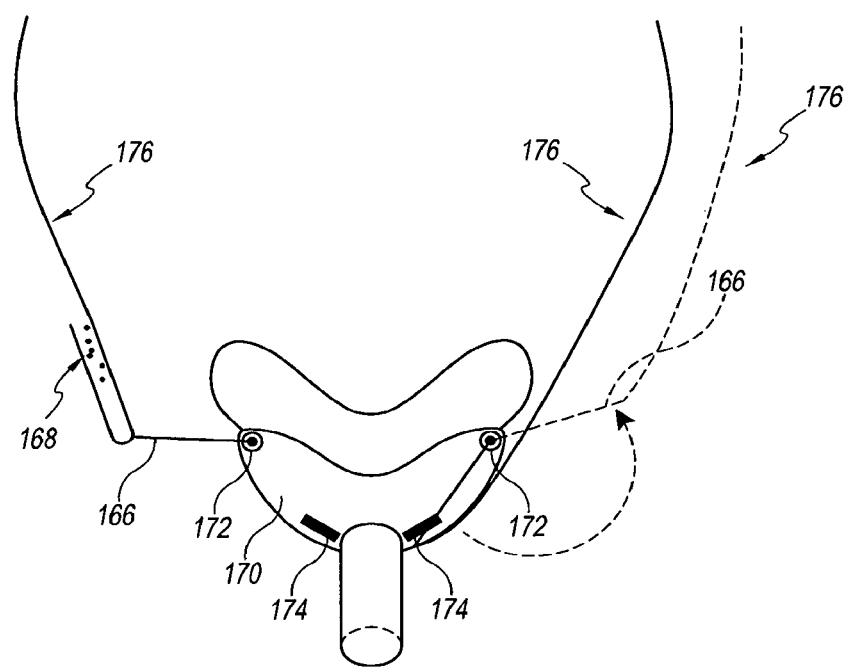
FIG. 7 is a top view of the interface of FIG. 6.
Figure 8B:
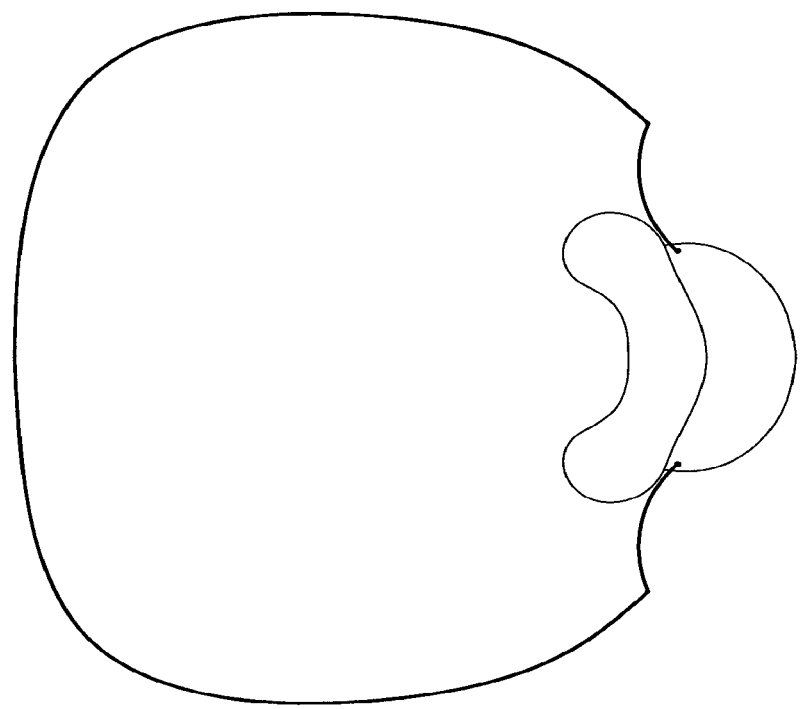
FIG. 8B is a schematic top plan view of a second step of adjusting a strap length for donning the interface of FIG. 6.
Figure 8A:
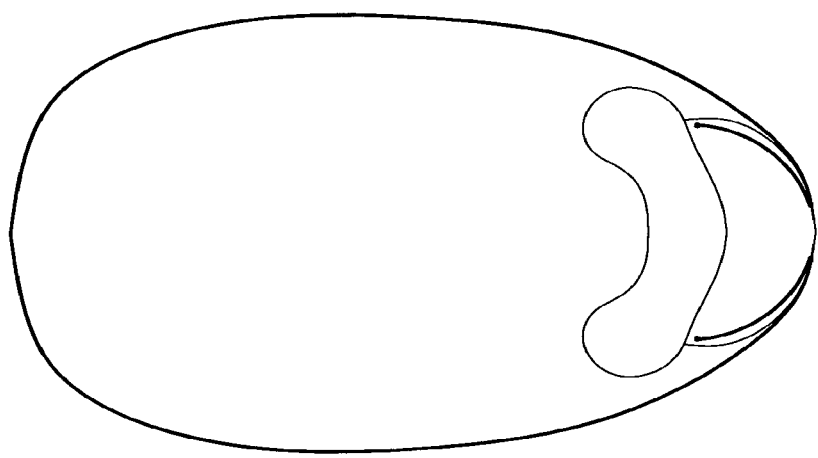
FIG. 8A is a schematic top plan view of a first step of adjusting a strap length for donning the interface of FIG. 6.

With reference to FIG. 7, headgear 176 is connected to the flaps 166 in any suitable manner. The length of the flaps 166 between the hinges 172 and the point at which the headgear 176 couples to the flaps 166 defines the length by which the loop can be increased (e.g., two times this length can be added). Thus, lengthening the distance between the hinges and the coupling point can increase the usable length for the break-fit assembly 164 (as seen in FIG. 6). In addition, while a single flap 166 is shown, the flaps 166 can comprise two or more leafs that accordion over each other. Thus, multiples of the length between the hinges and the coupling point can be attained.

With reference still to FIG. 7, the flaps 166 can open independently of each other. On the left side of FIG. 7, the flap 166 is opened and connected to the headgear 176. On the right side of FIG. 7, the flap 166 is shown in solid lines in the closed or latched position and is shown moving to the opened position. As indicated by the dashed arrow, the flap 166 swings between the latched position and the open position. Both flaps 166 are shown in the closed position on the left in FIG. 8 and both flaps 166 are shown in the open position on the right in FIG. 8. The movement is shown in dashed lines in FIG. 7.

Figure 9:
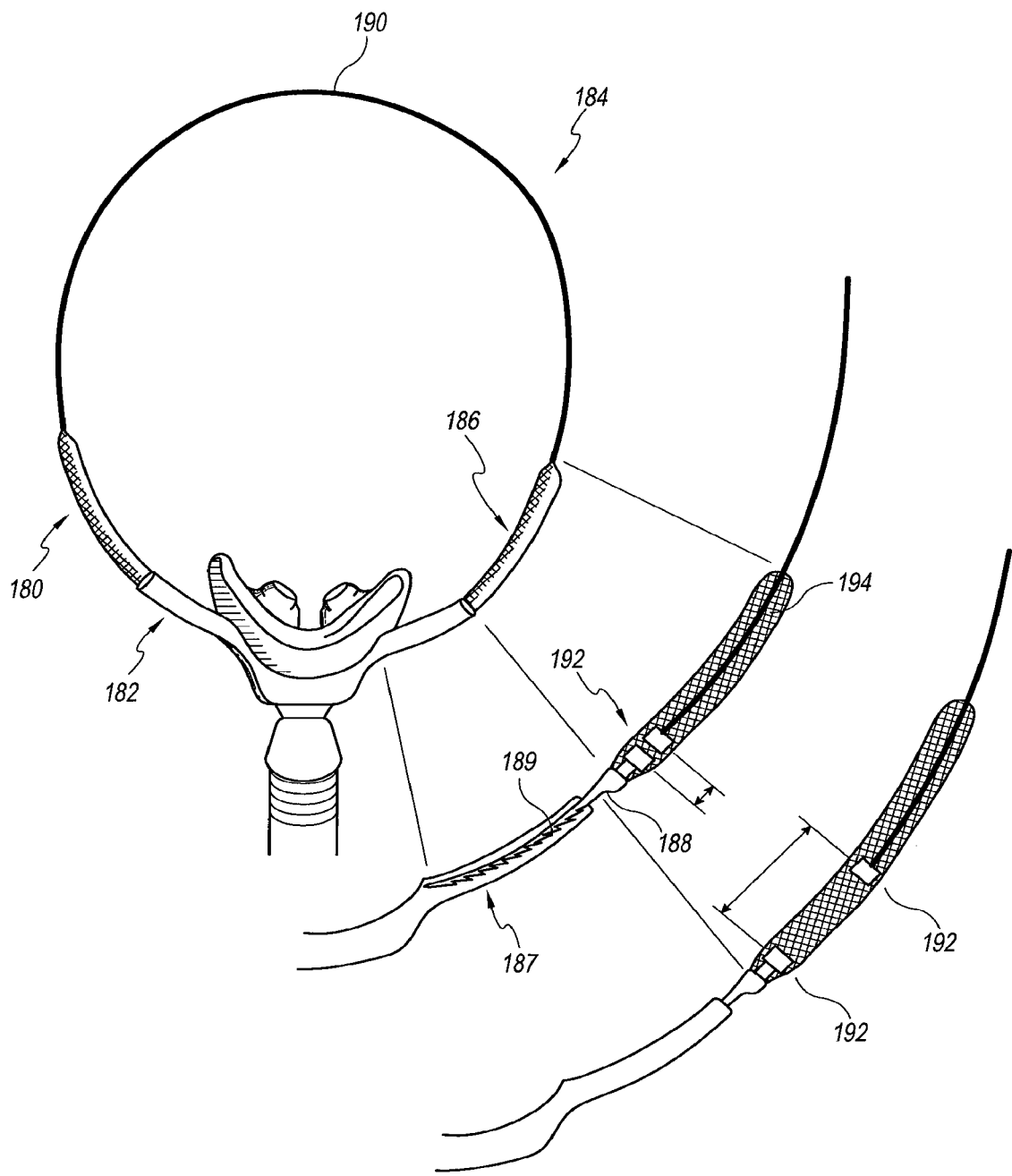
FIG. 9 is a top view and two section views of an interface that is arranged and configured in accordance with certain features, aspects and advantages of the present invention.

With reference now to FIG. 9, an interface 180 has a frame 182 and headgear 184. A break-fit assembly 186 can be positioned between the frame 182 and the headgear 184. The headgear 184 can comprise a generally inelastic portion 190. The generally inelastic portion 190 can extend between two break-fit assemblies. At least one break-fit assembly can connect the generally inelastic portion 190 to the frame 182, directly (see FIG. 10) or indirectly (see FIG. 9). In the configuration of FIG. 9, two break-fit assemblies connect the generally inelastic portion 190 to the frame 182.

The break-fit assembly 186 comprises two magnetic members 192. As described above, the magnetic members 192 can include at least one magnet or a combination of at least one magnet and at least one magnetizable member (e.g., a ferrous material). The magnetic members 192 are oriented to be attracted to each other. As such, when the magnetic members 192 are brought within a range to allow magnetic coupling, the magnetic members 192 self-align and self-connect.

The magnetic members 192 have a range of movement relative to each other that results in the magnetic members 192 moving outside of the range for magnetic coupling. For example, when the magnetic members 192 move beyond about 10 to about 20 mm apart, the magnetic coupling force is not strong enough to draw the magnetic members 192 back together.

Accordingly, to assist with reconnection and alignment, a flexible sheath 194 can envelop the magnetic members 192. Because the magnetic members 192 are very forgiving with respect to alignment, the flexible sheath 194 is sufficient to guide the magnetic members 192 back together and keep the magnetic members 192 generally on the same path for reconnection. The flexible sheath 194 can be any suitable elastic material. In some configurations, the flexible sheath 194 can be formed from silicone, a stretchy plastic material, a stretchy rubber material, or a stretch textile.

The magnetic members 192 can be fixed at least axially within the flexible sheath 194. In some configurations, the magnetic members 192 are fixed rotationally and/or axially within the flexible sheath 194. The magnetic members 192 can be attached to the flexible sheath 194 in any suitable manner. For example but without limitation, the magnetic members 192 can be glued, sewn, overmolded, or the like to secure the magnetic members 192 and the flexible sheath 194 together.

The magnetic member 192 closest to the frame 182 can be attached directly (see FIG. 10) or indirectly (see FIG. 9) to the frame 182. The magnetic member furthest from the frame 182 can be attached to an end of the generally inelastic member 190. In some configurations, the magnetic member 194 furthest from the frame 182 can be directly connected to the end of the generally inelastic member 190, as illustrated in FIG. 9 for example but without limitation.

In the illustrated configuration, a portion of the sheath 194 extends along and/or wraps around at least a portion of the inelastic member 190. In some configurations, the sheath 194 extends the full distance or substantially the full distance from one side of the frame 182 to the other side of the frame 182. Moreover, in some configurations, the sheath 194 can be secured to at least a portion of the inelastic member 190. For example, the sheath 194 can be bonded to at least a portion of the inelastic member 190. Other configurations also are possible. In the illustrated configurations, a distance from the laterally outermost portion of the sheath 194 to the magnetic member 192 secured to the inelastic member 190 generally will not change. However, a distance from the laterally innermost portion of the sheath 194 to that same magnetic member 192 will vary due to stretching of the sheath 194

As illustrated in FIG. 9, when the outer magnetic members 192 move away from the inner magnetic members 192, the length of the headgear 180 increases. The movement of the magnetic members 192 away from each other is resisted of the elastic material of the sheath 194. Thus, stretching of the sheath 194 establishes a restoration force that will act to return the magnetic members 192 toward each other for reconnection to a resting position. The resting position is a position where the break-fit assembly is connected by a force sufficient to withstand the forces generated by the seal of the interface during normal use of the CPAP plus hose drag. Hose drag can be any force applied to the mask system by the CPAP hose being pulled away from the user or being dragged over any surface. In other words, the force coupling the magnetic members 192 preferably is above a maximum force created by the pressurized breathing gases within the interface, which pressurized breathing gases originate from the CPAP blower force. For example but without limitation, at about 20 cm H$_2$O, there is a force of about 5 N pushing the mask away from the face of the users so the magnetic members 192 preferably exert a coupling force of greater than about 5 N. In some configurations, the magnetic attraction is preferably greater than about 4 to 5 N, which this takes into account a relatively high treatment pressure (e.g., about 20 cm H$_2$O) and a difficult to seal patient geometry.

With reference now to FIGS. 11 through 17, additional break-fit assemblies are illustrated therein. The break-fit assemblies illustrated in FIGS. 11 through 17 achieve a break-fit function through the use of mechanical couplings rather than magnetic couplings. Each of the break-fit assemblies can be connected to inelastic headgear as described above and can be used in place of, or in combination with, any of the other break-fit assemblies described herein. As described above, the break-fit assemblies facilitate a temporarily enlargement of a loop defined by the interface to ease donning; the mechanical arrangements described herein can provide an extension of between about 25 mm and about 100 mm in some configurations. In some configurations, the extension is between about 30 mm and about 70 mm. In some configurations, the extension is about 50 mm. It should be noted that the mechanical break-fit assemblies tend to have a longer axial length than the magnetic break-fit assemblies do. However, the mechanical break-fit assemblies offer other distinct advantages over the use of magnets.

Figure 11:
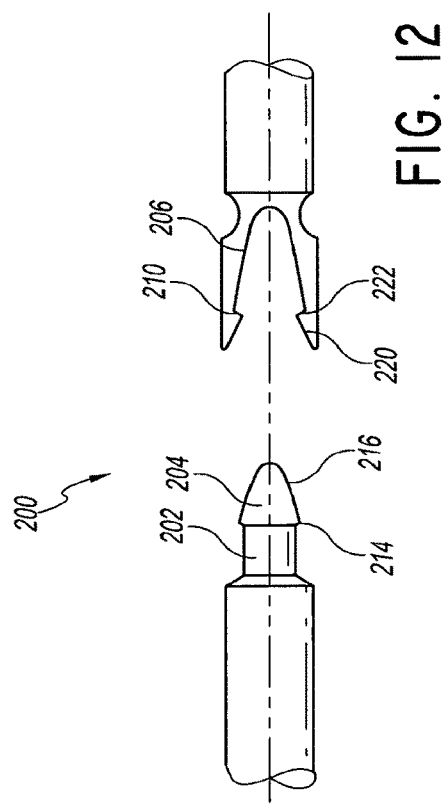
FIG. 11 is a top view of a break-fit assembly that is arranged and configured in accordance with certain features, aspects and advantages of the present invention.
Figure 12:
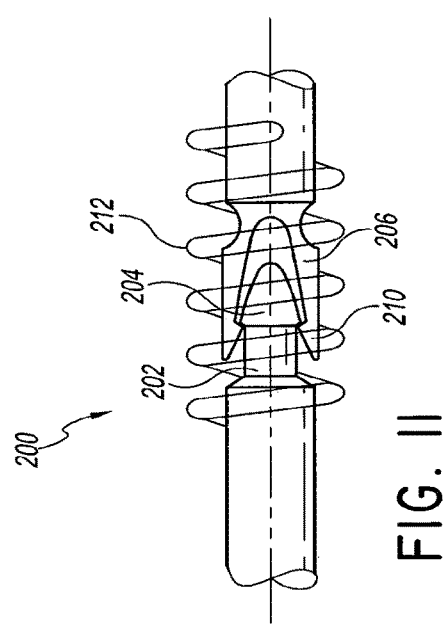
FIG. 12 is an orthogonal view of a portion of the break-fit assembly of FIG. 11 in an open state.

With reference first to FIGS. 11 and 12, a break-fit assembly 200 has a construction that allows a separation of a first component and a second component at a predetermined force while facilitating rejoining of the first component and the second component in a mechanical manner. In the illustrated embodiment of FIGS. 11 and 12, the first component can comprise a post 202 with a head 204 and the second component can comprise a receptacle 206 with a resilient opening 210. The first component and the second component can be joined by a biasing member 212, such as an elasticated sleeve or spring, for example but without limitation. The biasing member 212 can be secured to the first component and the second component in any suitable manner. In addition, in the illustrated configuration, the biasing member 212 overlies any gap that will be created when the first component and the second component separate. Thus, the biasing member 212 can act to guide the reconnection of the first and second components.

The head 204 in the illustrated configuration has a gently sloping portion 216 and a more severely angled portion 214. Similarly, the receptacle 206 has a gently sloping portion 220 and a more sharply angled portion 222. The surfaces 214, 216, 220, 222 are but one configuration of surfaces that can be used. Advantageously, the illustrated configuration using the gently sloping interfaces 216, 220 facilitates a low coupling force while using the more sharply angled interfaces 214, 222 causes a higher separation force. Accordingly, the illustrated break-fit assembly 200 will separate at a relatively higher force than the force required by the assembly 200 to recombine. As with the assemblies discussed above, preferably, the assembly 200 will separate at a tensile load of about 4 N or 5 N or more.

Figure 13:
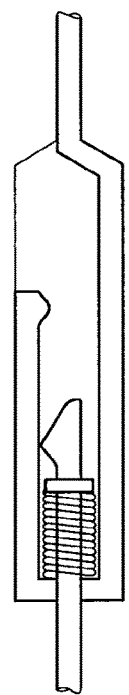
FIG. 13 is a top sectioned view of a break-fit assembly that is arranged and configured in accordance with certain features, aspects and advantages of the present invention.
Figure 14:
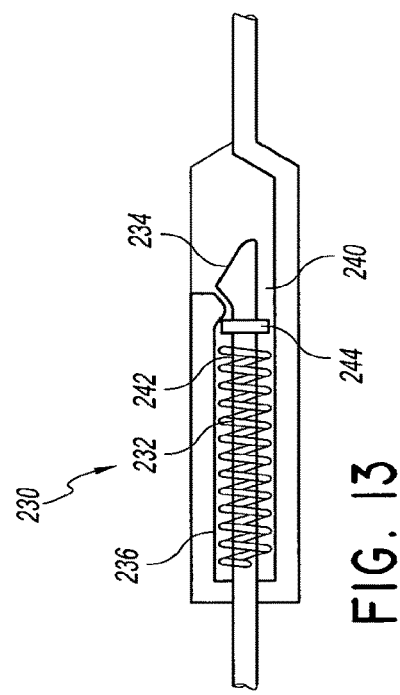
FIG. 14 is an enlarged view of a portion of the break-fit assembly of FIG. 13.
Figure 15:
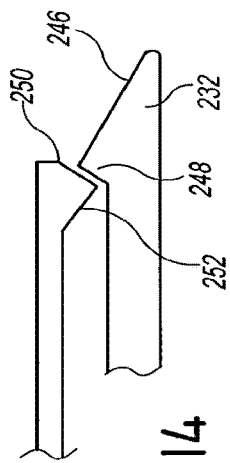
FIG. 15 is a top sectioned view of the break-fit assembly of FIG. 13.

With reference now to FIGS. 13 through 15, another break-fit assembly 230 has a construction that allows a separation of a first component and a second component at a predetermined force while facilitating rejoining of the first component and the second component in a mechanical manner. In the illustrated embodiment of FIGS. 13 through 15, the first component can comprise a post 232 with a head 234 and the second component can comprise a receptacle 236 with an opening 240. The post 232 can extend through a wall that defines the receptacle 236. As such, the post 232 can slide within the receptacle 236. With the post 232 sliding within the receptacle 236, alignment generally results.

A return force between the first component and the second component can be created by a biasing member 242. In the illustrated assembly 230, the biasing member is positioned within the second component. As shown, the biasing member 242 is positioned within the receptacle 236. The biasing member 242 can be a spring, for example but without limitation. The illustrated biasing member 242 comprises a compression spring. A retainer 244 secures the biasing member 242 over the post 232. The retainer can be integrally formed with the post 232 or can be separately formed and secured thereto in any suitable manner. The biasing member 242 therefore bears against a surface of the receptacle 236 and the retainer 244.

With reference to FIG. 14, the head 234 in the illustrated configuration has a gently sloping portion 246 and a more severely angled portion 248. Similarly, the receptacle 236 has a gently sloping portion 252 and a more sharply angled portion 250. The surfaces 246, 248, 250, 252 are but one configuration of surfaces that can be used. Advantageously, the illustrated configuration using the gently sloping interfaces 246, 252 facilitates rejoining at a low coupling force while using the more sharply angled interfaces 248, 250 results in separation occurring at a higher separation force. Accordingly, the illustrated break-fit assembly 230 will separate at a relatively higher force than the assembly 230 will recombine. As with the assemblies discussed above, preferably, the assembly 230 will separate at a tensile load of about 4 N or 5 N or more.

With reference now to FIGS. 16 and 17, another break-fit assembly 260 has a construction that also allows a separation of a first component and a second component at a predetermined force while facilitating rejoining of the first component and the second component in a mechanical manner. In the illustrated embodiment of FIGS. 16 and 17, the first component can comprise a post 262 with a head 264 and the second component can comprise a receptacle 266 with an opening 270. The post 262 can extend through a wall that defines the receptacle 266. As such, the post 262 can slide within the receptacle 266. With the post 262 sliding within the receptacle 266, alignment generally results.

A return force between the first component and the second component can be created by a biasing member 272. In the illustrated assembly 270, the biasing member overlays at least a portion of each of the first and second components. The biasing member 272 can be a spring or a resilient sleeve, for example but without limitation. The illustrated biasing member 272 is a resilient fabric sleeve that generally encases the first component and the second component.

With reference to FIG. 17, the head 264 in the illustrated configuration has a gently sloping portion 274 and a more severely angled portion 276. Similarly, the receptacle 266 has a gently sloping portion 280 and a more sharply angled portion 282. In the illustrated configuration, the gently sloping portion 280 of the second component comprises a displaced inner wall of the receptacle 266 and the more sharply angled portion 282 comprises an end of that wall that forms the gently sloping portion 280. The surfaces 274, 276, 280, 282 are but one configuration of surfaces that can be used. Advantageously, the illustrated configuration using the gently sloping interfaces 274, 280 facilitates a low coupling force while using the more sharply angled interfaces 276, 282 causes a higher separation force. Accordingly, the illustrated break-fit assembly 260 will separate at a relatively higher force than the assembly 260 will recombine. As with the assemblies discussed above, preferably, the assembly 260 will separate at a tensile load of about 4 N or 5 N or more.

As introduced above, when using generally inelastic headgear, the user may desire some form of adjustment. In some instances, the adjustment will occur during set-up of the device and no further adjustment will be performed. In other instances, the user may wish to be able to adjust the headgear as desired. Accordingly, FIGS. 3, 7, 9 through 11, and 18 through 62 will be used to describe various adjustment mechanisms that are arranged and configured in accordance with certain features, aspects and advantages of the present invention.

With reference initially to FIG. 3, as discussed above, the illustrated interface 120 includes an adjustment mechanism 134. In addition, FIG. 7 illustrates a similar adjustment mechanism 168 and FIG. 10 also illustrates a similar adjustment mechanism 198. Accordingly, the following description of the adjustment mechanism 134 shown in FIG. 3 can apply equally to the adjustment mechanism 168 shown in FIG. 7 and/or the adjustment mechanism 198 shown in FIG. 10.

The adjustment mechanism 134 is a simple buckle 135 with a hook and loop fastening configuration 138 formed on the inelastic portion 136 of the headgear 130. A tab of the hook and loop fastening configuration 138 can be passed through an opening defined within the buckle 135 and then secured in position after being doubled back upon itself, for example but without limitation. Other buckle configurations also can be used, including pin-based buckles or the like.

With continued reference to FIG. 3, the headgear 130 can be connected to the balance of the interface 120 using hooks 139 or the like. As illustrated, the hook 139 can be connected to a mounting structure formed on or connected to at least one of the frame 124 and the seal 122. Other assemblies are possible. In the configuration illustrated in FIG. 3, both the upper strap and the lower strap include the adjustment mechanism 134.

With reference now to FIG. 9, another adjustment mechanism 187 is illustrated therein. The adjustment mechanism 187 can comprise an insert 188 that includes teeth 189 and that is secured to the break-fit assembly 186. The insert 188 can be mated with an opening in the frame 182. The insert 188 interlocks with a structure in the frame 182. In some configurations, the teeth 189 of the insert 188 interlock with a structure in the frame 182. Preferably, the insert 188 is easy to move inward into the frame 182 but significantly more difficult to retract from the frame 182. An adjustment force is used to adjust the headgear. In some configurations, the frame 182 may include a release button that, when depressed, facilitates withdrawal of the insert 188 from the frame 182.

Figure 18:
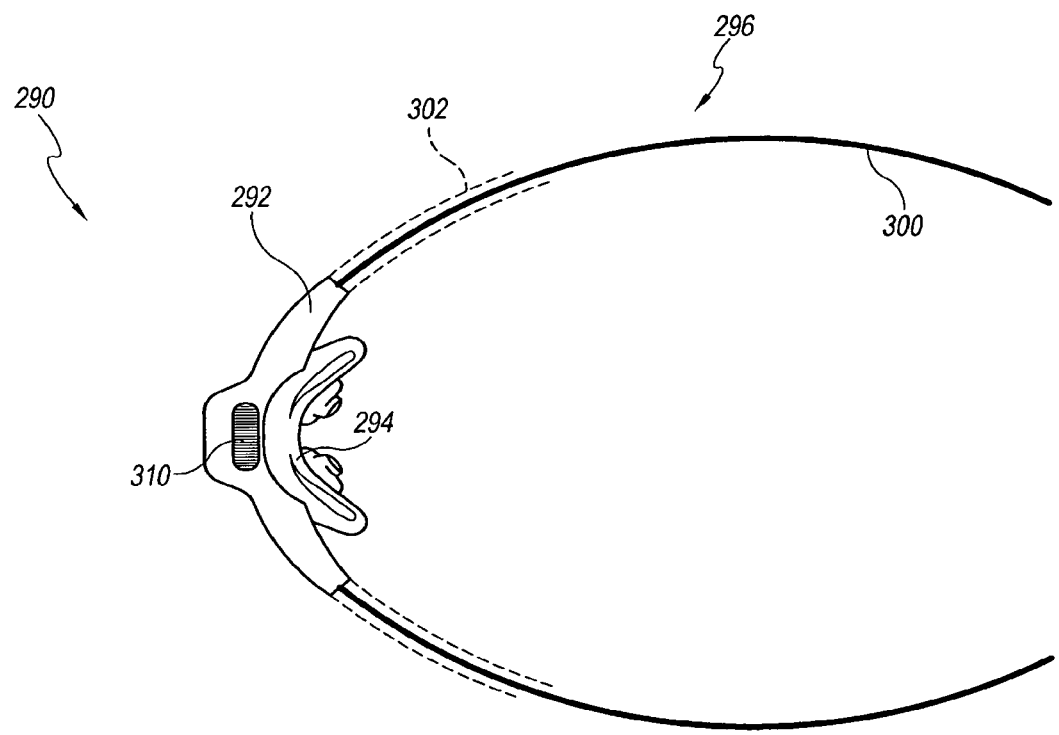
FIG. 18 is a top view of an interface that is arranged and configured in accordance with certain features, aspects and advantages of the present invention.
Figure 19:
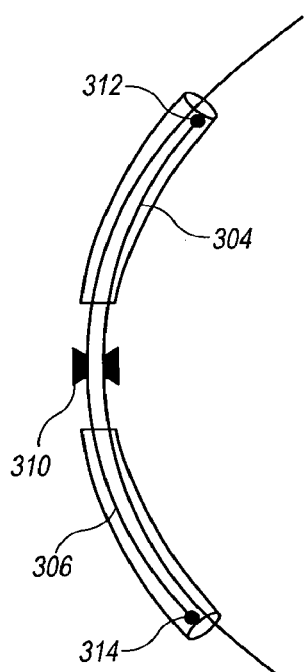
FIG. 19 is a partial view of a portion of the interface of FIG. 18 showing an adjustment mechanism.
Figure 20:
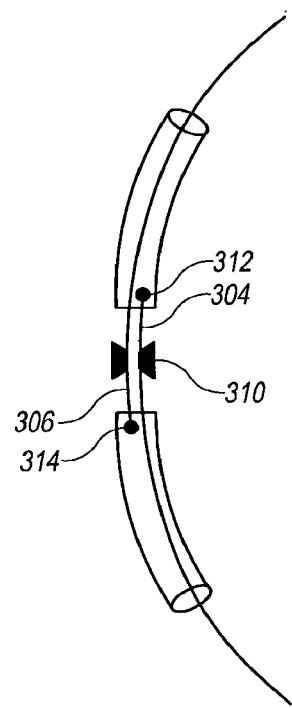
FIG. 20 is another partial view of a portion of the interface of FIG. 18.

With reference now to FIGS. 18-20, an interface 290 comprises a frame 292 and a seal 294. Headgear 296 is connected to the frame 292 in any suitable manner. The headgear 296 can comprise a generally inelastic member 300 and an outer cover member 302. The outer cover member 302 can comprise an elastic sleeve. The elastic sleeve 302 can be attached to the frame 292 in any suitable manner. The generally inelastic member 300 can move substantially freely within the sleeve 302.

With reference to FIG. 19 and FIG. 20, the generally inelastic inner member 300 has a first end 304 and a second end 306. The first end 304 and the second end 306 can overlap in the region of the frame 292. Movement of the ends 304, 306 changes the size of the loop defined by the headgear 296 and the frame 292 in the illustrated configuration. The stretch material of the elastic sleeve 302 proves a force that urges the inner generally inelastic member to a first position (e.g., the position shown in FIG. 19); the stretch material of the elastic sleeve 302, however, allows the ends 304, 306 to slide relative to each other such that the loop can be expanded. Thus, during donning of the interface 290, the headgear can be expanded and, when released, the elastic sleeve 302 attempts to return the headgear to the starting position.

With reference again to FIG. 18, the frame 292 can comprise a lock button 310. While a centrally located lock button 310 is shown, two or more lock buttons can be used. In some configurations, a separate lock button can be used for each of the ends 304, 306 and the lock buttons can be disposed laterally of the center point.

In some configurations, depressing the lock button 310 can release the ends 304, 306 to allow movement of one or both of the ends 304, 306. In some configurations, depressing the lock button 310 can lock the ends 304, 306 relative to each other and relative to the frame 292 such that the size of the loop no longer changes. If the lock button 310 requires depression to lock the ends 304, 306, it is possible to allow the headgear 296 to function like an elastic headgear until the lock button 310 is depressed. In some configurations, the lock button 310 operates a release mechanism (e.g., a clothing toggle) that allows movement when depressed and, in some configurations, the lock button 310 operates a clamping mechanism (e.g., friction brake) that reduces or eliminates the likelihood of movement when depressed. Any suitable locking mechanism can be used.

In the illustrated configuration, at the extremities of the ends 304, 306 are stops 312, 314. The stops 312, 314 can be used to limit the amount of stretch provided by the headgear 296. For example, the stops 312, 314 can be constructed such that, while the ends 304, 306 can pass through the frame 292, the stops cannot fully pass through the frame 292. In some configurations, the stops 312, 314 are configured to not enter the frame 292 at all. Other configurations also are possible.

Figure 21:
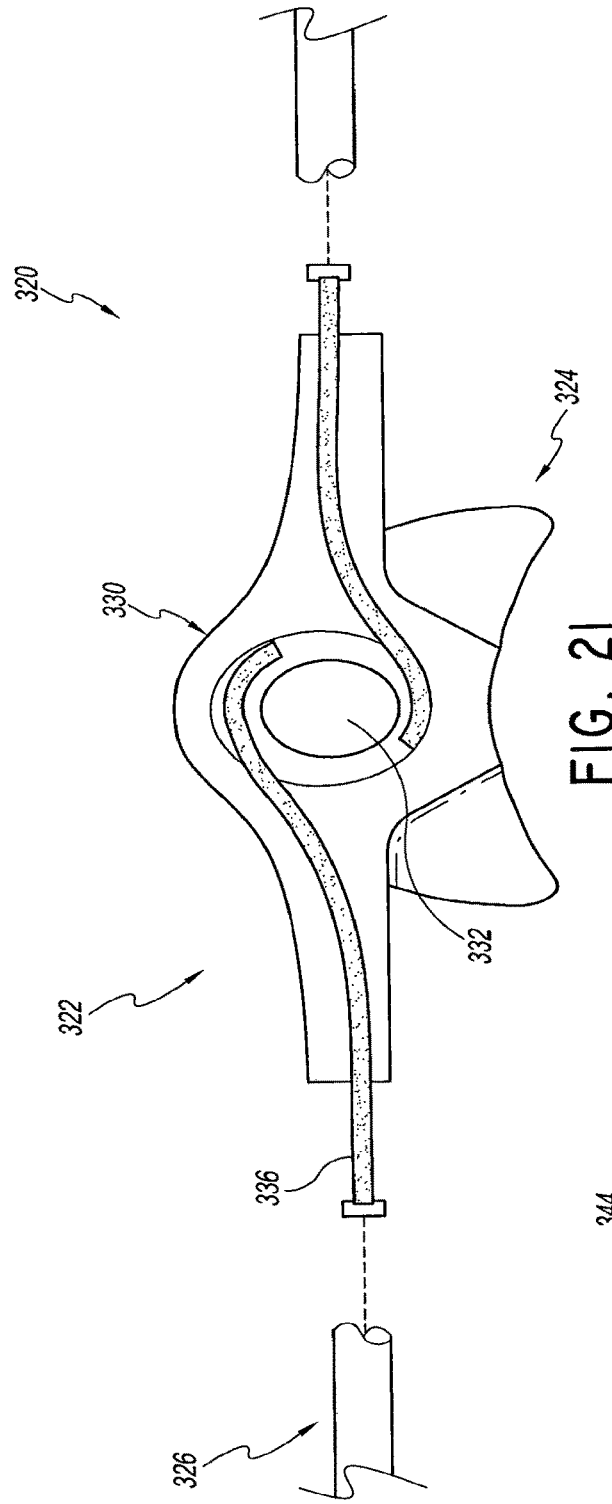
FIG. 21 is a top view of an interface having an adjustment mechanism that is arranged and configured in accordance with certain features, aspects and advantages of the present invention.
Figure 23:
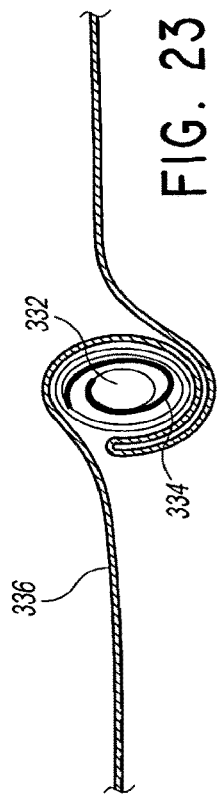
FIG. 23 is a simplified view of a portion of an adjustment mechanism similar to that of FIG. 21, which adjustment mechanism is arranged and configured in accordance with certain features, aspects and advantages of the present invention.
Figure 22:
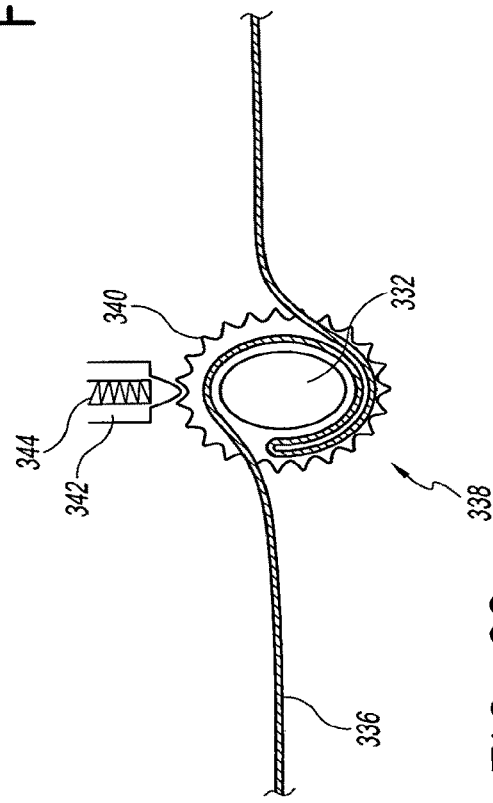
FIG. 22 is a simplified view of a portion of the adjustment mechanism of FIG. 21.
Figure 24:
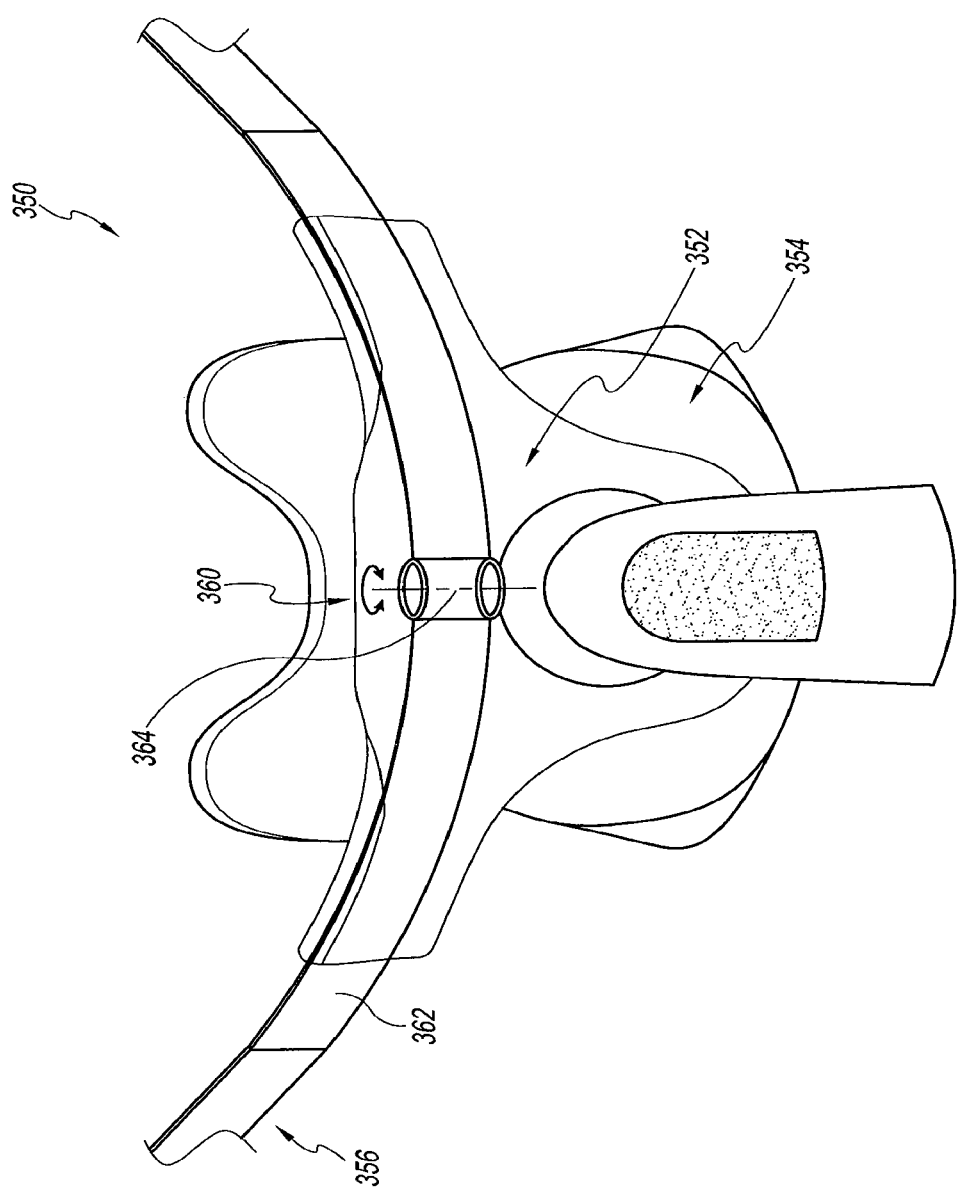
FIG. 24 is a view of an interface having an adjustment mechanism that is arranged and configured in accordance with certain features, aspects and advantages of the present invention.

FIGS. 21 through 23 illustrate another interface 320 having a frame 322, a seal 324 and headgear 326. The frame 322 in the illustrated configuration comprises an adjustment mechanism 330. FIGS. 22 and 23 illustrate slightly different variations of the adjustment mechanism 330, mostly relating to a biasing member.

The adjustment mechanism 330 can be connected to the headgear 326 in any suitable manner. For example, the headgear 326 can be formed within an inelastic member and can include hooks, clasps, or other mechanical connection members. Moreover, in some configurations, a break-fit assembly, including but not limited to any break-fit assembly described herein, can be interposed between the headgear 326 and the adjustment mechanism 330.

The adjustment mechanism 330 can be positioned within a housing of the frame 322. The adjustment mechanism 330 can be positioned around an inlet that is coupled to a supply conduit (not shown). Such a positioning provides an efficient use of space and results in a symmetric configuration. With reference to FIG. 22, the adjustment mechanism 330 is shown in a simplified view. The adjustment mechanism 330 can comprise a reel disk 332 and a coil spring 334 (see FIG. 23). In some configurations, a coil spring can be omitted. In some configurations, rather than the coil spring 334, such as that of FIG. 22, an elastic outer member (not shown) can be used in a manner similar to that used in the configuration of FIGS. 18 through 20.

At least one extensible member 336 can be connected to the reel disk 332. Two extensible members 336 are shown in FIG. 21 while a single extensible member is shown in FIGS. 22 and 23. When a single extensible member 336 is used, the member 336 preferably folds back over itself in at least one location. The extensible member 336 can be a cord, string, tape, or the like, for example but without limitation. The extensible member 336 preferably is generally inelastic and is mounted such that it can be unwound from and retracted back onto the reel disk 332.

The reel disk 332 can be mounted on a spool or axle (not shown) such that the reel disk 332 can rotate about an axis. A locking mechanism 338 can be provided to secure the length of extensible member 336 that is extended from the housing. The reel disk 322 can be provided with, or connected to a member that includes, locking structure 340, such as recesses, teeth, or the like. A locking pin 342 can be biased, such as by a spring 344 for example but without limitation, into the locking structure 340. In some configurations, a locking assembly using a friction brake or the like can be used. Desirably, the locking assembly reduces or eliminates the likelihood of further withdrawal of the extensible member. While the extensible member 336 can be retracted into the housing following obtaining a setting in certain configurations, the extensible member 336 preferably cannot be pulled further out from the housing once locked.

With reference to FIGS. 24-29, an interface 350 is illustrated that includes a frame 352, a seal 354 and headgear 356. An adjustment mechanism 360 can be provided that connects the headgear 356 to the balance of the interface 350. The adjustment mechanism 360 comprises a winding mechanism similar to that discussed directly above. For example, the adjustment mechanism 360 includes a thin band of material 362, such as a cord, tape or the like, that winds onto and off of a spool 364 such that the band of material 362 can coil about the spool 364.

With reference to FIG. 25, the headgear 356 can be generally inelastic and can be joined to the band 362 in any suitable manner. In the illustrated configuration, the headgear 356 and the band 362 can be connected by a shuttle member 366. Advantageously, using the shuttle 366 results in the band 362 being continuously retained within the frame 352. By retaining the band 362 within the frame 352, the band 362 can be formed of a very thin material yet be protected from wear and abuse.

The shuttle member is configured to move axially along at least a portion of the frame 352. Movement of the shuttle 366 toward the spool 364 (e.g., to the left in FIG. 25) acts to remove slack in the headgear 356 (i.e., shorten the loop) while movement of the shuttle 366 away from the spool 364 (e.g., to the right in FIG. 25) acts to increase slack in the headgear 356 (i.e., lengthen the loop). Any suitable locking mechanism can be used to secure the assembly at a desired position. For example, any of the following can be locked in position: the spool 364, the band 362, the shuttle 366 or the headgear 356. In some configurations, the spool 364 comprises a locking mechanism such as those described above. In some configurations, the shuttle 366 can have detent components that click from one position from the next or the shuttle 366 can move between a clamped position and a freely slidable position (e.g., a clamped position can be created when the shuttle 366 is squeezed into position on a frame component such that it clamps onto the frame component and a freely slidable position can be created when the shuttle is pulled from the frame component and able to slide along the frame component).

In the illustrated configuration, the shuttle member 366 is positioned in a slot 370 formed within the frame 352. The slot 370 can be positioned as desired. For example, the slot 370 can be on a surface of the frame 352 that faces the user, that faces away from the user, that faces up or that faces down. Adjacent to the slot 370 can be graduated markings to help users identify a desired setting. In some configurations, the slot can be omitted (see, e.g., FIG. 27). In some configurations, the frame 352 can simply comprise an opening rather than a slot (see, e.g., FIG. 28).

As also illustrated in FIGS. 26-29, the shuttle member 366 can be captured or connected to the frame 352 in any desired manner. For example, the shuttle member 366 can include recesses that receive flanges of the frame 352. In some configurations, the frame 352 can include recesses that receive flanges of the shuttle member 366. Desirably, the shuttle member 366 is connected to the frame 352 in such a manner that the shuttle member 366 can translate along at least a portion of the frame 352.

Figure 30:
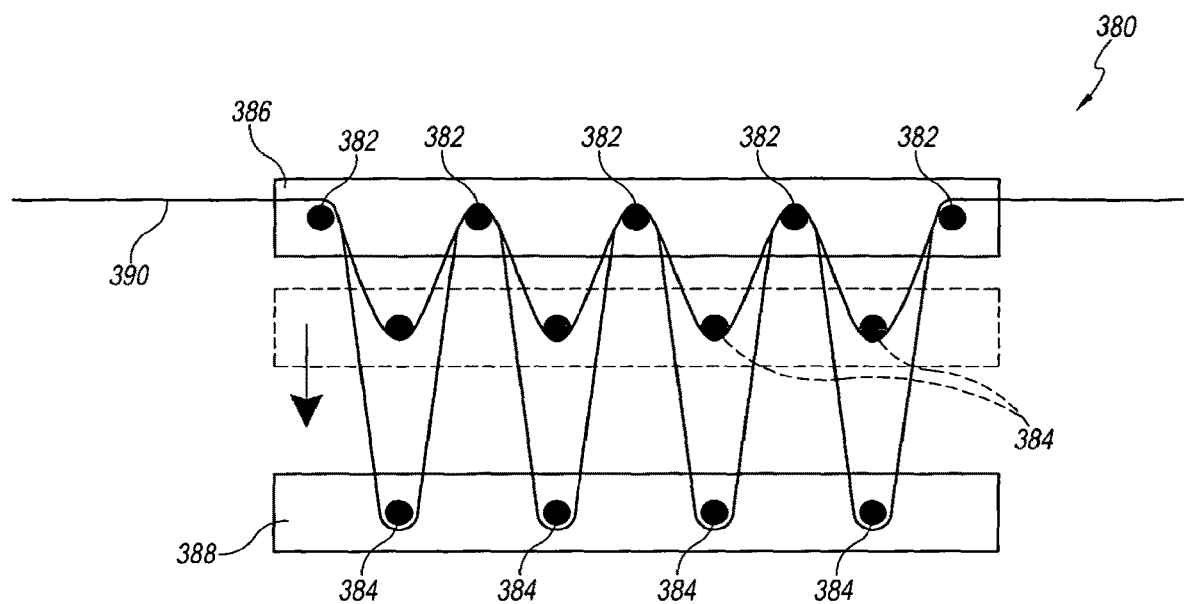
FIG. 30 is a schematic view of an adjustment mechanism that is arranged and configured in accordance with certain features, aspects and advantages of the present invention.
Figure 31:
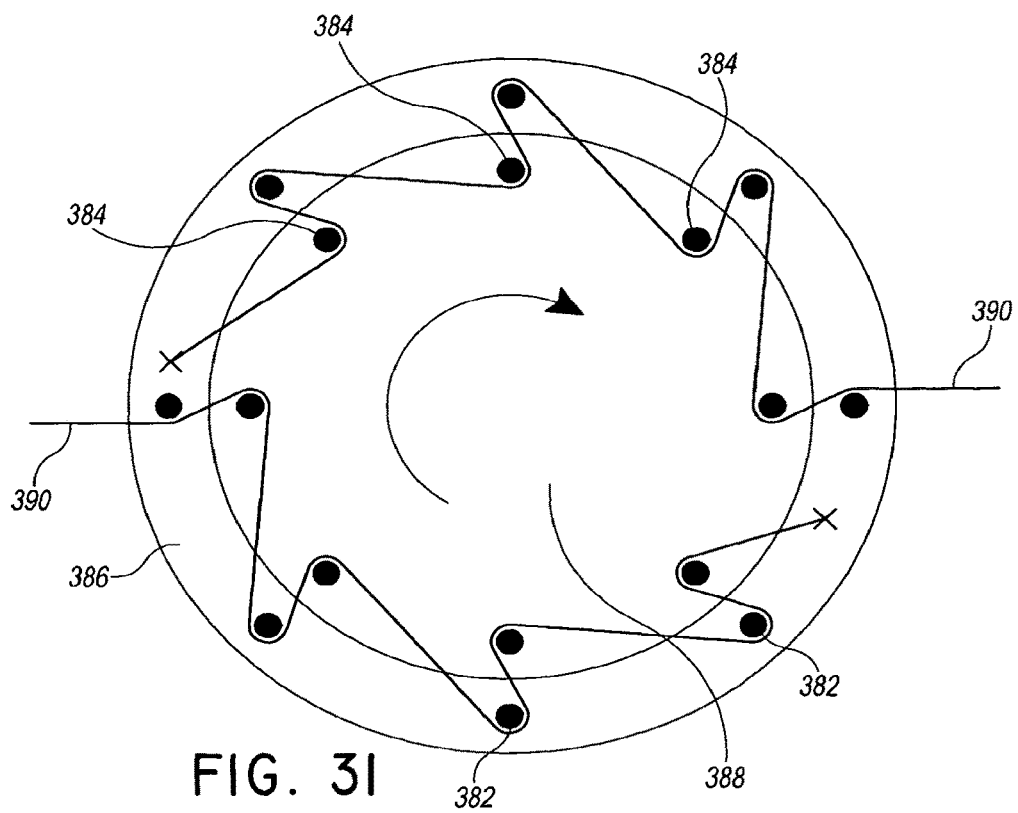
FIG. 31 is a schematic view of another adjustment mechanism that is arranged and configured in accordance with certain features, aspects and advantages of the present invention.

With reference now to FIGS. 30 and 31, two different adjustment mechanisms 380 are illustrated in a schematic fashion. The mechanism 380 can be positioned in a frame of the interface (e.g., in a recess within the frame) or in a separate housing. In some configurations, the mechanism 380 can be positioned in a housing located along a portion of the headgear, for example but without limitation. As described above, spools have been used to remove slack or adjust a length of the headgear. The takeup mechanisms 380 can be used to adjust the length of the headgear in any of the configurations described herein. The illustrated mechanisms 380 comprise a first set of pins 382 and a second set of pins 384. The first set of pins 382 are positioned on a first body 386 and the second set of pins 384 are positioned on a second body 388.

By moving the first body 386 relative to the second body 388, a length of an extensible member 390 can be adjusted. In FIG. 30, a single member 390 is shown and, in FIG. 31, two members 390 are shown with each member secured to one of the bodies (e.g., the first body 386).

FIG. 30 illustrates a linear movement while FIG. 31 illustrates a rotational movement. Advantageously, a very small relative movement between the first body 386 and the second body 388 can result in a significant change in length of the extensible member 390. Increasing the number of pins 382, 384 increases the effect on length. Reducing the number of pins 382, 384 reduces the effect on length.

Any suitable movement can be used. In FIG. 31, the outer body 386 can be rotated while the inner body 388 remains stationary or the outer body 386 can remain stationary while the inner body 388 rotates or both bodies 386, 388 may rotate. The relative movements can be created in any suitable manner. For example, linear movements can be controlled by a lever, a button or the like, which can be connected to one or both of the bodies 386, 388. Rotational movements also can be control by dials, levers, buttons or the like.

With reference now to FIGS. 32 through 34, another interface 400 is illustrated that includes a frame 402, a seal 404 and headgear 406. An adjustment mechanism 410 can be provided. With reference to FIGS. 33 and 34, the adjustment mechanism 410 comprises a rack and pinion assembly.

A pinion 412 can be mounted between two racks 414. The pinion 412 and the racks 414 can be positioned within the frame 402. The ends of the racks 414 can connect to the headgear 406 or can be integrated into the headgear 406. In some configurations, the racks 414 connect to the headgear 406 outside of the frame 402. In some configurations, the racks 414 connect to the headgear 406 inside of the frame 402. The racks 414 can be flexible enough to wrap slightly around the pinion 412 to provide more purchase between the racks 414 and the pinion 412 and bring the racks into alignment for generally symmetrical headgear attachment. In some configurations, relief recesses 415 can be provided to increase the flexibility of the racks 414.

With reference again to FIG. 32, a ring or other input device 416 can be positioned on a surface of the frame 402. For example but without limitation, the ring 416 can be positioned on the front of the frame 402 and can surround a connector through which breathing gases are supplied to the interface 400. Rotation of the input device 416 causes rotation of the pinion 412.

The pinion 412 comprises teeth 418 and the racks 414 include cooperating teeth 420. As the pinion 412 rotates, the teeth 418, 420 cause axial movement of the racks 414. In this manner, the racks 414 can be used to adjust the loop. Any suitable locking mechanism can be used to lock the position of the headgear 406, the racks 414, the pinion 412 and/or the ring 416. For instance, a pin or the like can be used to inhibit rotation of the pinion 412 and/or the ring 416. In some configurations, a friction brake, a clamping mechanism, a cammed break member or the like can be used to inhibit movement of one or more of the headgear 406, the racks 414, the pinion 412 and/or the ring 416. Moreover, while not illustrated, a break-fit assembly can be used as well. For example, the input device can have limits that are adjustable and that limit the range of rotation. In some such configurations, a coil spring or other biasing member can urge the input device toward the limit associated with the smaller headgear size. As such, the headgear can expand but then automatically retract to the predetermined use size under the influence of the biasing member.

Figure 35:
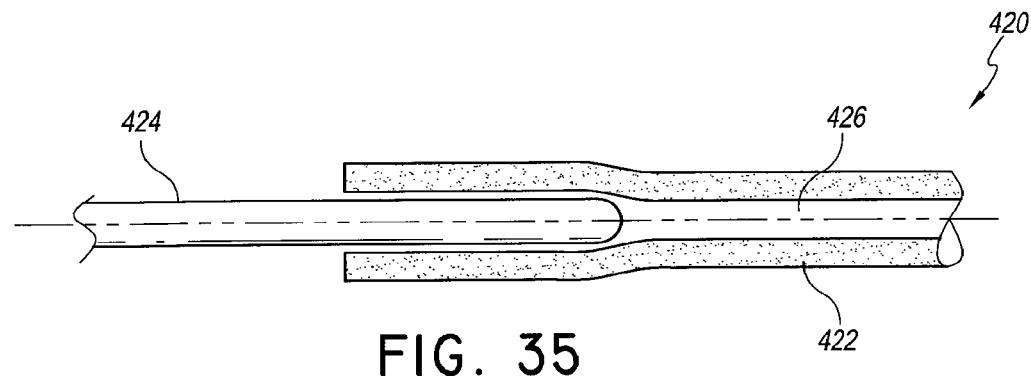
FIG. 35 is a schematic view of an adjustment mechanism that is arranged and configured in accordance with certain features, aspects and advantages of the present invention.
Figure 36:
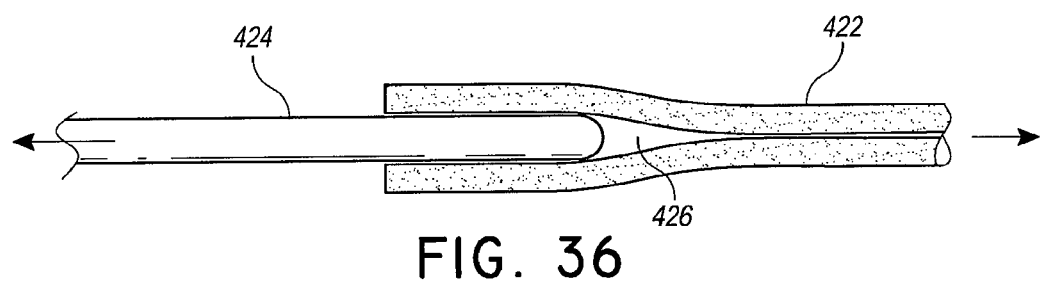
FIG. 36 is another schematic view of the adjustment mechanism of FIG. 35.
Figure 37:
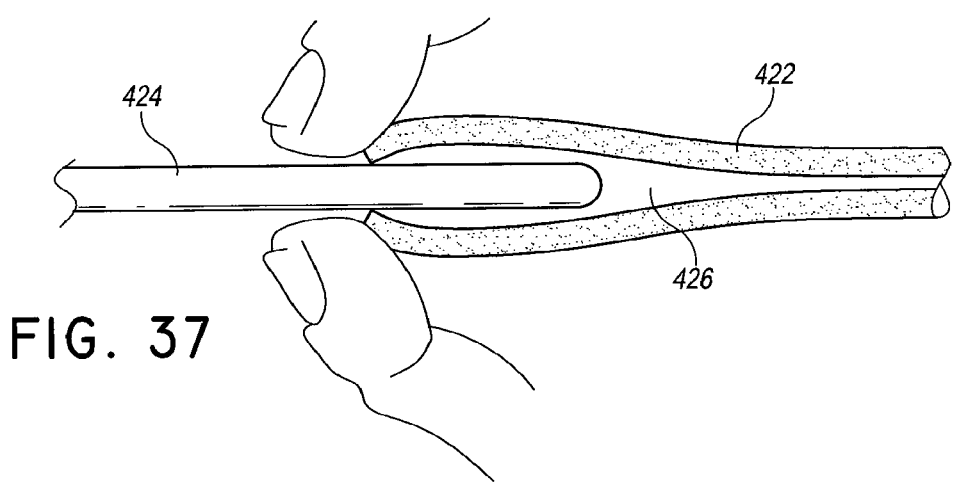
FIG. 37 is a further schematic view of the adjustment mechanism of FIG. 35.

With reference now to FIGS. 35-37, a further adjustment mechanism 420 is illustrated. The adjustment mechanism 420 comprises a resilient sleeve 422 and a post 424. The resilient sleeve 422 can be formed from any suitable material. In some configurations, the resilient sleeve 422 is formed from silicone, for example but without limitation. In some configurations, the resilient sleeve 422 can be formed from a woven material, which material may or may not be resilient. The post 424 can be formed from any suitable material. In some configurations, the post 424 is formed from a steel roll, for example but without limitation.

The resilient sleeve 422 includes a passage 426. The passage 426 can have an inner diameter or inner dimension that is smaller than an outer diameter or corresponding outer dimension of the post 424. The post can be easily inserted into the passage 426. Insertion of the post 424 into the passage 426 causes stretching of the resilient sleeve 422. The stretching of the sleeve 422 causes the material to become tight against the post 424. Any attempt to simply apply tensile forces to the two members causes further tightening of the interface between the sleeve 422 and the post 424. See FIG. 36. As shown in FIG. 37, to release the post 424 from the sleeve 422, an end of the sleeve 422 can be manipulated to effectively limit the necking of the sleeve 422 while withdrawing the post 424. Thus, the end of the sleeve 422 can be moved axially away from the post 424 by causing axial compression of the sleeve. Thus, the sleeve 422 and the post 424 can form a very effective adjustment mechanism.

Figure 38:
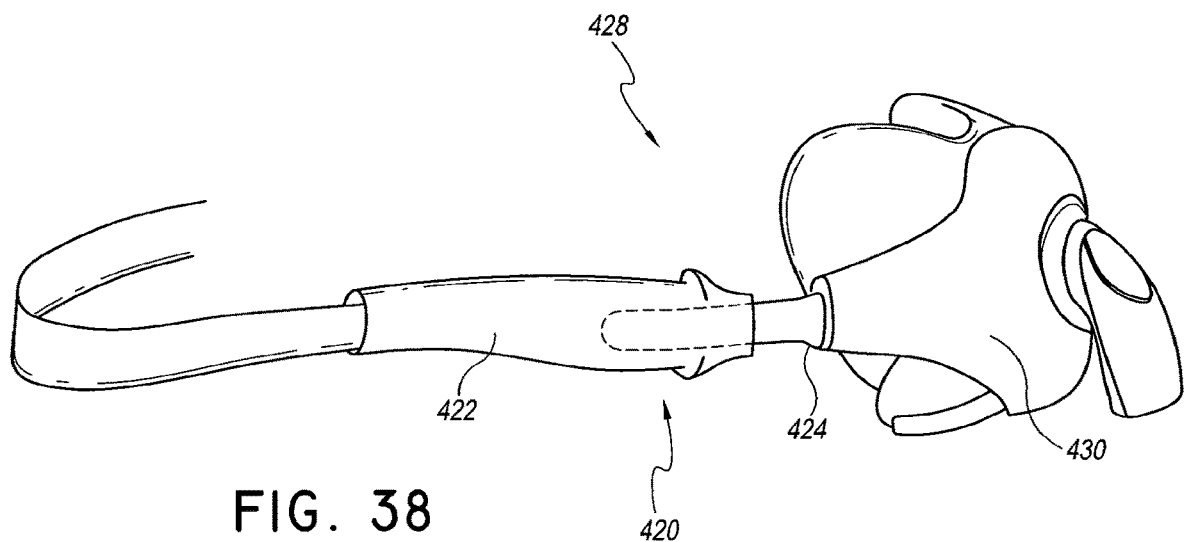
FIG. 38 is a side view of an interface using the adjustment mechanism of FIG. 35.
Figure 39:
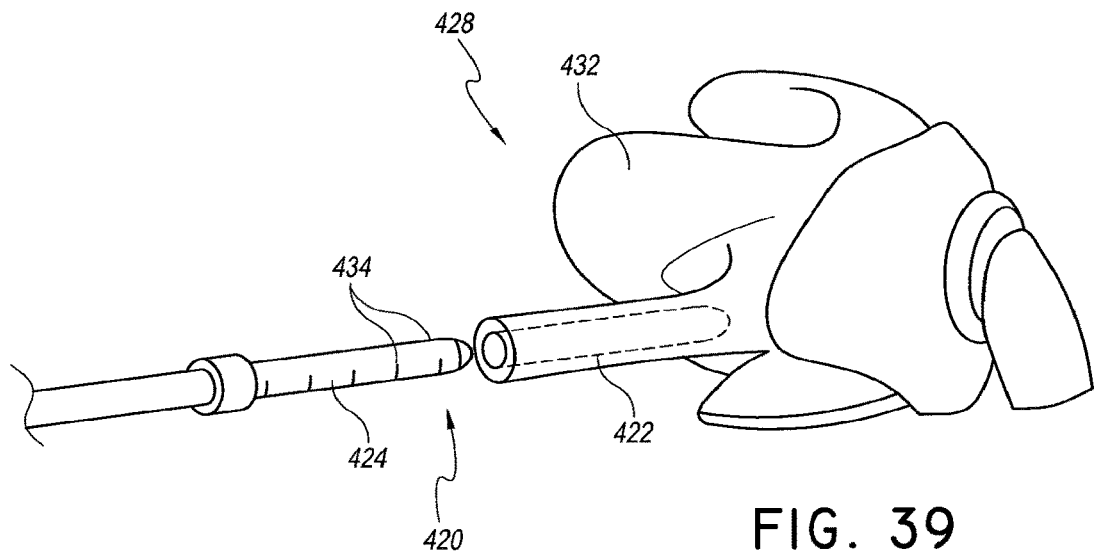
FIG. 39 is a side view of another interface using the adjustment mechanism of FIG. 35.

With reference to FIGS. 38 and 39, these figures illustrate two ways of integrating the adjustment mechanism 420 into an interface 428. As illustrated therein, the post 424 can be formed as part of the mask (FIG. 38) or as part of the headgear (FIG. 39) and the sleeve 422 can be formed as part of the headgear (FIG. 38) or as part of the mask (FIG. 39). With respect to the component that is formed on the mask side, the component can be integrated into the frame or the seal. In FIG. 38, the post 424 is formed as part of a frame 430 while, in FIG. 39, the sleeve 422 is formed as part of a seal 432. Moreover, as shown in FIG. 39, a scale 424 or other demarcations can be provided along a portion of the post 424 to indicate the length of the post 424 that has been fed into the sleeve 422. In some configurations, the sleeve 422 can include demarcations as well or as an alternative to the demarcations 434 on the post 424.

Figure 40:
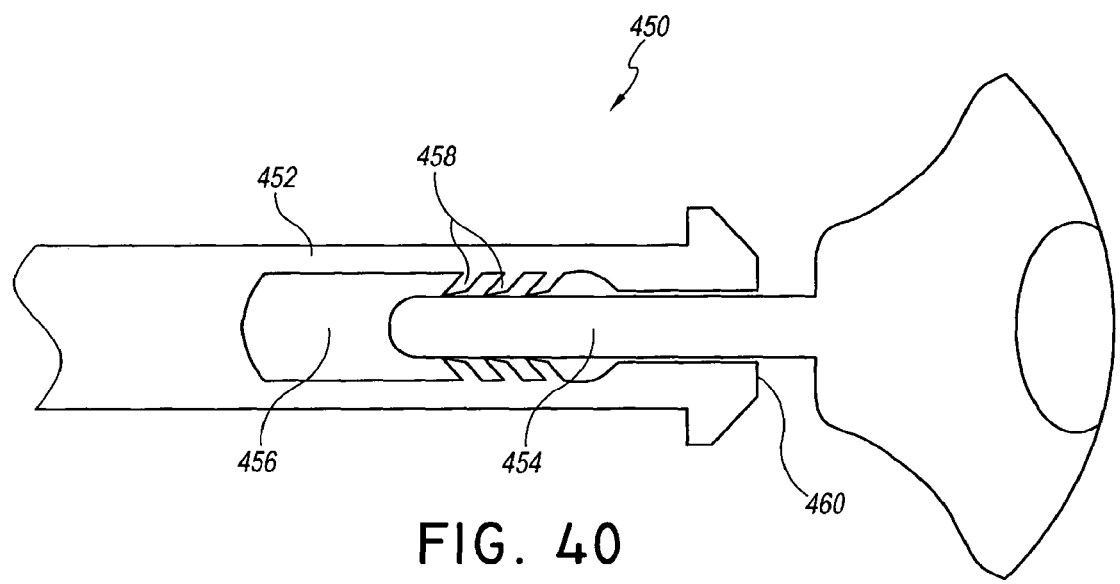
FIG. 40 is a schematic view of an adjustment mechanism that is arranged and configured in accordance with certain features, aspects and advantages of the present invention.
Figure 41:
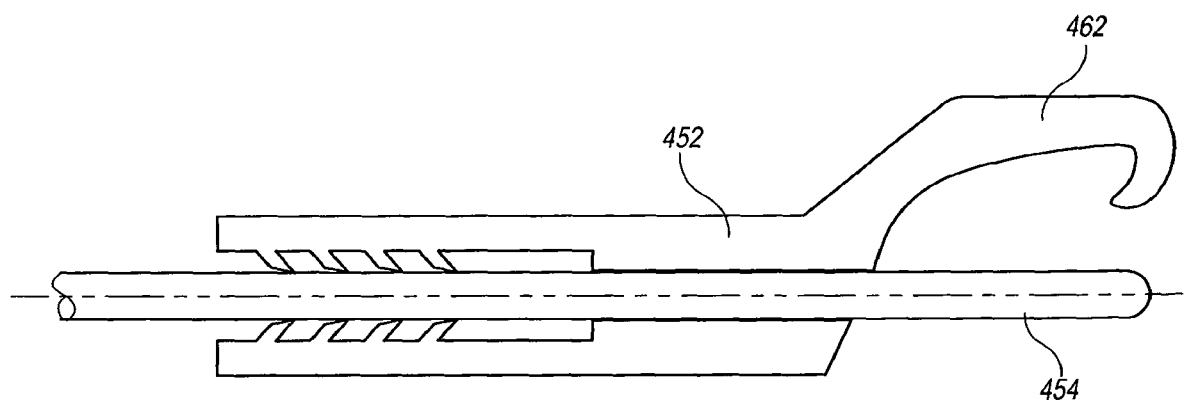
FIG. 41 is a schematic view of an adjustment mechanism that is arranged and configured in accordance with certain features, aspects and advantages of the present invention.

With reference to FIGS. 40 and 41, two further adjustment mechanisms 450 are illustrated therein. As illustrated, the adjustment mechanisms comprise a sleeve 452 and a post 454. As with the configuration just described, the post 454 is received within a passage 456 of the sleeve 452. As illustrated in FIG. 40, the passage 456 can comprise one or more tabs 458 that resist withdrawal of the post 454 from the passage 456. For example, the tabs 458 may slant away from an opening 460 of the sleeve 452 or the tabs 458 may be sufficiently flexible and sufficiently long that, upon insertion of the post 454 into the passage 456, the tabs 458 deflect away from the opening 460. Attempts to withdraw the post 454 from the passage 456 will be resisted by the tabs 458 but the tabs will not prevent the withdrawal of the post 454 upon the application of sufficient force. The distance between the tabs will be smaller than the diameter or width of the post 454 such that when the post is inserted the tabs will grip on the post and be forced to bend inwards. The length of the tabs and their material may cause them to grip on the post and deform, thus increasing the interference with the post and requiring a greater force to remove the post from the sleeve.

As with the embodiment above, the adjustment mechanism 450 can be formed between the headgear and the mask. For example, the post 454 can be connected to, or integrally formed with, a portion of the mask while the sleeve 452 is formed with or connected to the headgear (see FIG. 40). In some configurations, the sleeve 452 can be integrated into, or joined to, a hook 462. As such, the sleeve 452 and the hook 462 can be used to connect a mask and headgear together while also providing adjustability. See FIG. 41.

Figure 42:
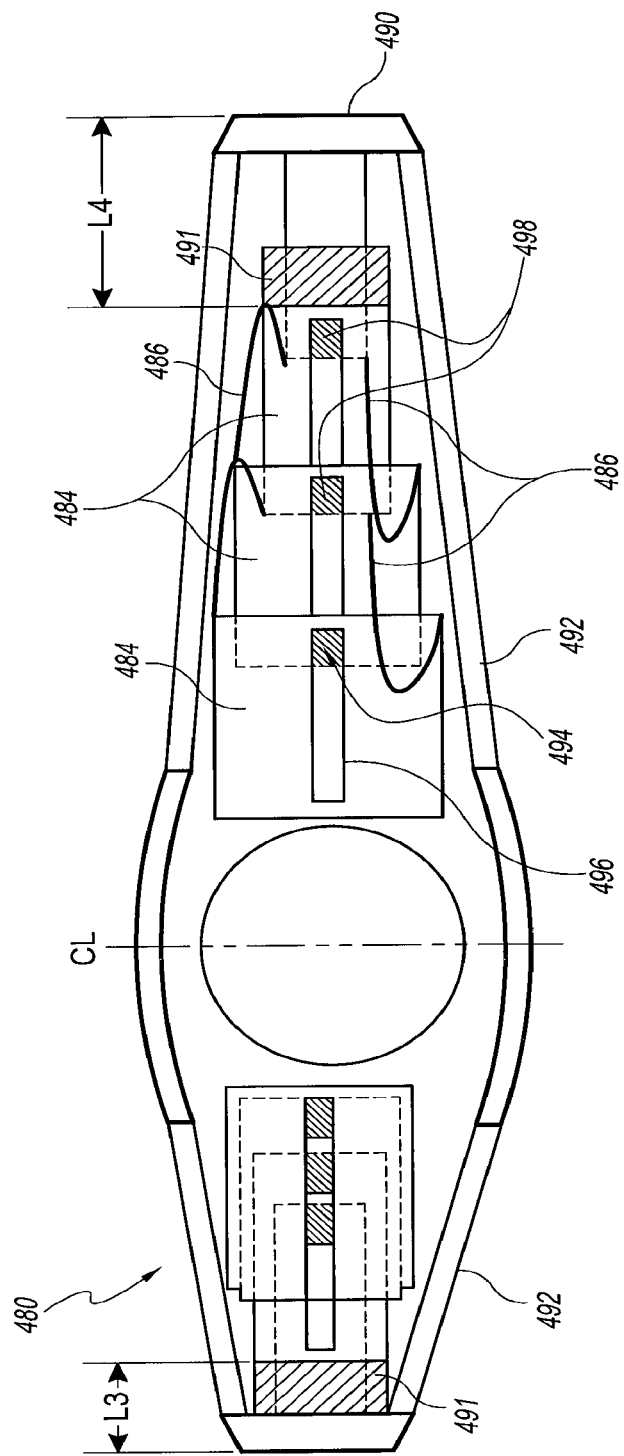
FIG. 42 is a schematic view of another adjustment mechanism that is arranged and configured in accordance with certain features, aspects and advantages of the present invention.
Figure 43:
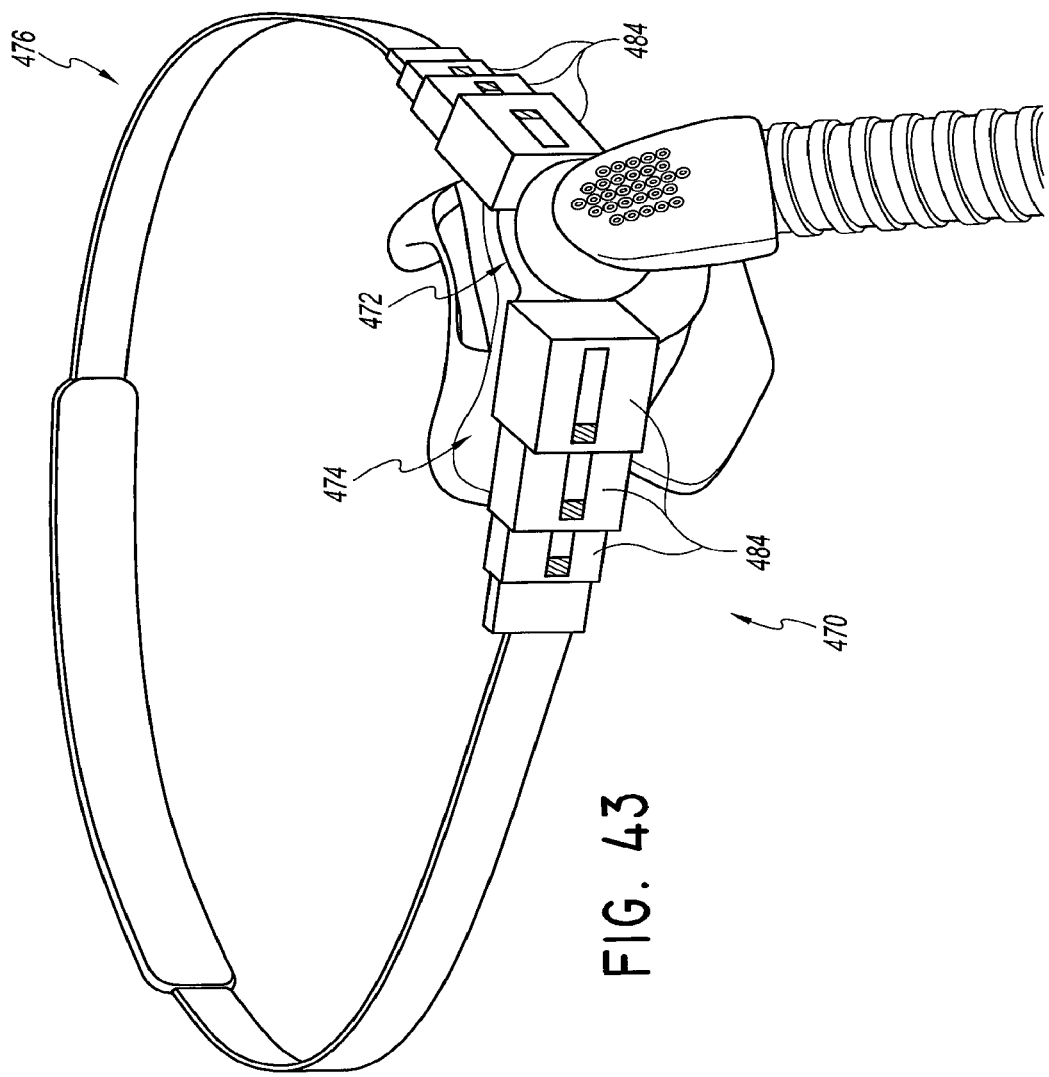
FIG. 43 is a schematic view of an interface having the adjustment mechanism of FIG. 42.
Figure 44:
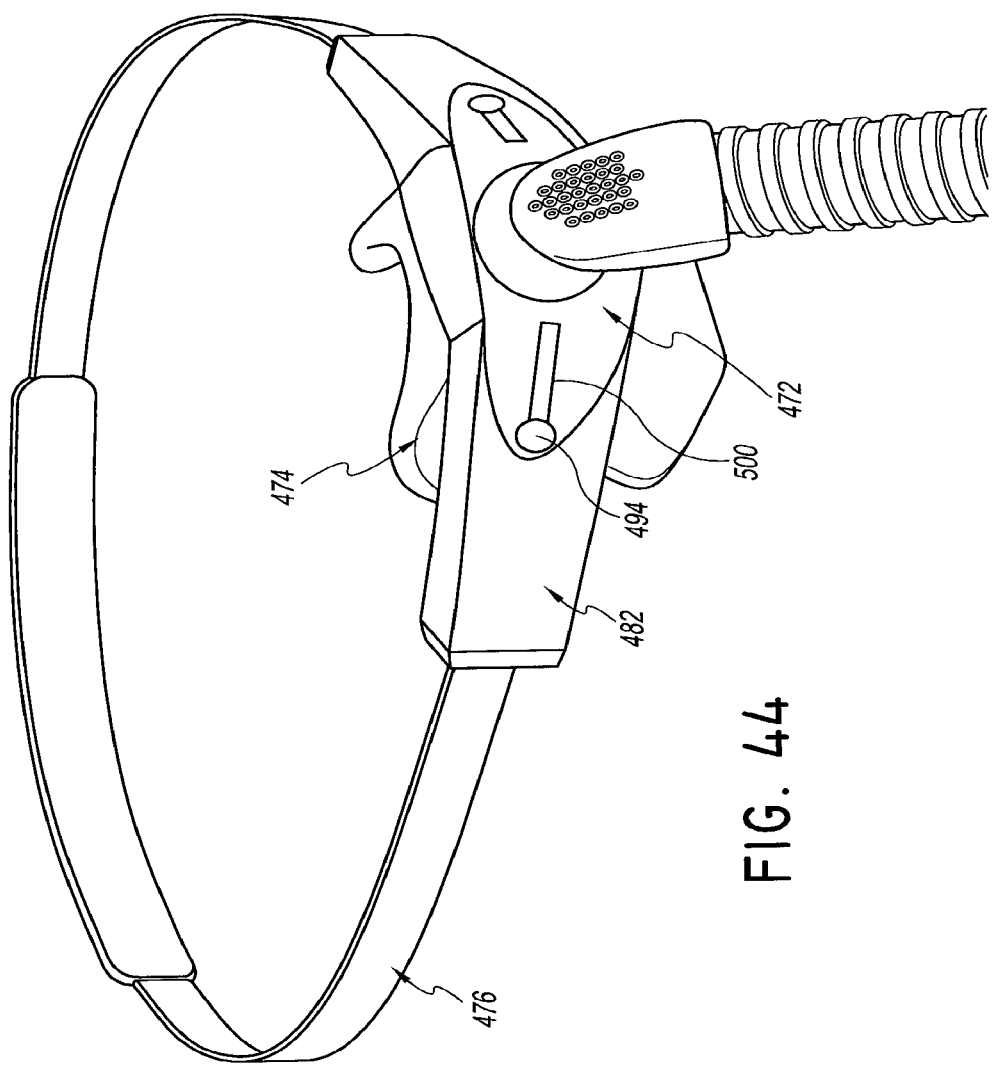
FIG. 44 is another schematic view of the interface of FIG. 43.

With reference now to FIGS. 42 through 44, an interface 470 is illustrated. The interface 470 comprises a frame 472, a seal 474 and headgear 476. An adjustment mechanism 480 can connect the headgear 476 to the balance of the interface 470. For example, as illustrated in FIG. 44, the frame 472 can include a housing 482 that contains the adjustment mechanism 480, which is shown in FIGS. 42 and 43. The adjustment mechanism connects to the headgear 476.

FIG. 43 illustrates that the adjustment mechanism 480 can include a plurality of telescoping members 484. The telescoping members 484 are designed to nest one inside of another. As such, when collapsed, the telescoping members 484 define a first length and, when extended, the telescoping members 484 define a second length that is longer than the first length. This relationship is best shown by comparing the left side of FIG. 42 and the right side of FIG. 42.

To provide for symmetrical movement of the telescoping members 484, connecting cables 486 can be used. For example, a first connecting cable 486 can join an upper portion of a first member 484 to a lower portion of a third member 484 by looping over an upper portion of a second member 484 (see cables on upper portion of FIG. 42). Similarly, a second connecting cable 486 can join a lower portion of the third member 484 to an upper portion of the first member 484 by looping under a lower portion of the second member 484 (see cables on lower portion of FIG. 42). When the members 484 move, the cable or cables 486 maintain balanced positions that result in the members moving in a synchronized manner.

The outermost member 484 can define an end magnet or magnetizable material that can be connected to, or can define, an end cap 490 of the adjustment mechanism 480. Located at the upper portion of the third member 484 can be another magnet or magnetic material that defines a base 491, which in one position is adjacent the end cap 490. The end cap 490 and the base 491 may both comprise magnets, respectively, or one may comprise a magnet while the other comprises a magnetizable material. The end cap 490 and the base 491 are held together with a magnetic force. When adjacent to each other, the distance or length between the lower portion of the base 491 to the upper portion of the end cap 490 is defined as L3. If a force exceeding the magnetic force is applied in an opposing direction the one or more magnets will be forced apart to define a distance or length of L4 where L4 is greater than L3.

Figure 10:
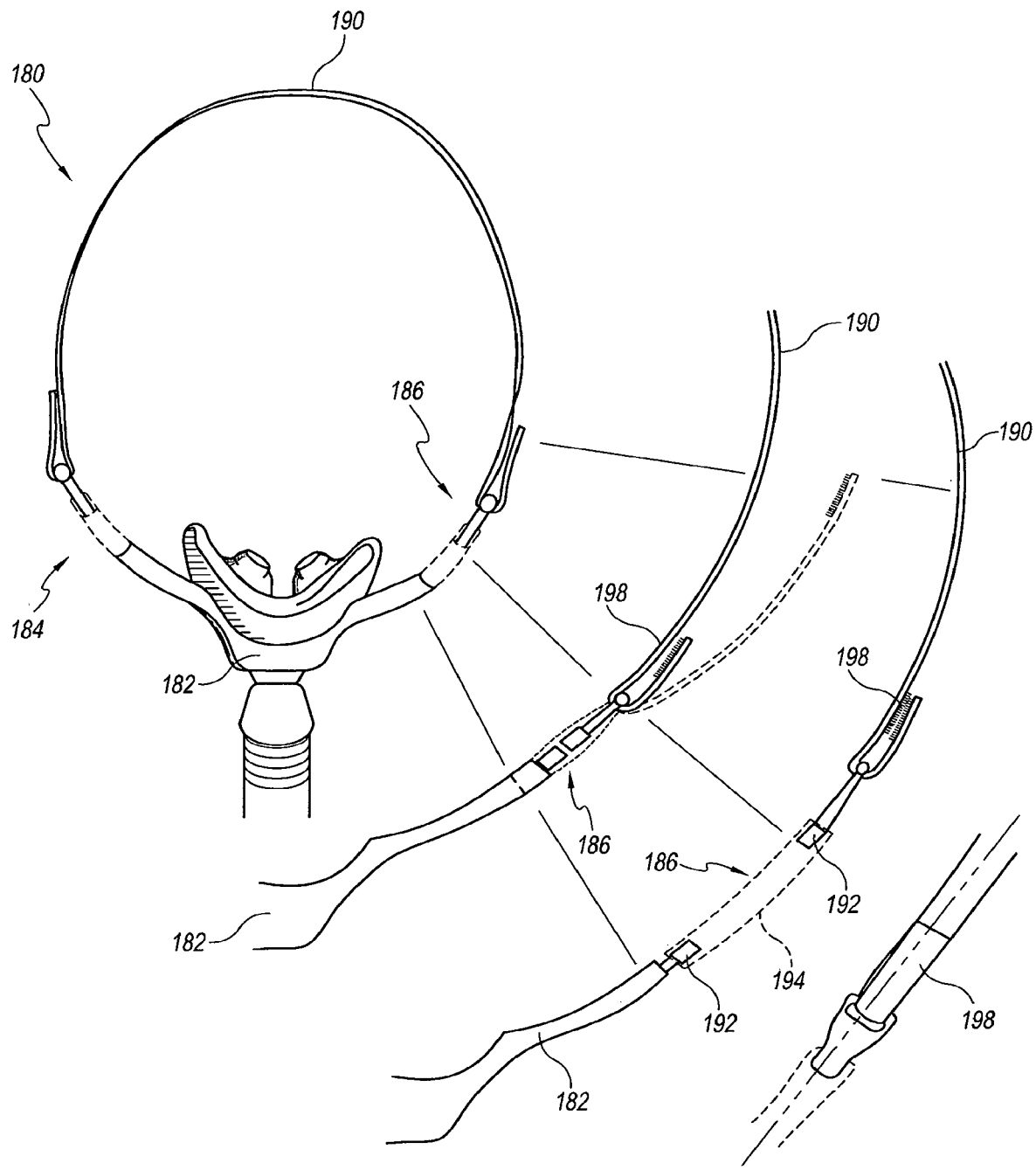
FIG. 10 is a top view, two section views and a partial side view of an interface that is arranged and configured in accordance with certain features, aspects and advantages of the present invention.

The end cap 490 and the base 491 together provide the same or a similar break-fit function as those described in FIGS. 9 and 10. When an axial force is applied to the end cap 490, the end cap 490 pulls away from the base 491 thereby loosening the tension on the headgear 476, which may be beneficial for ease of removal or adjustment. Because of the magnetic force between the end cap 490 and the base 491, the two elements may tend to be drawn back together when the force keeping them apart is removed or reduced. Other elements of the headgear 476 may also draw the two elements back together. For example, a resilient member 492 (as described in greater detail below) may comprise an elastic material that will draw the end cap 490 and the base 491 back toward each other if separated.

In some embodiments, the end cap 490 is secured to the upper portion of a telescoping member 484. In FIG. 42, end cap 490 is shown as affixed to the upper portion of the fourth telescoping member 484. Because the fourth telescoping member 484 slides into and out of the third telescoping member 484, the base 491 positioned at the upper end of the third telescoping member 484 may be configured to accommodate such movement. For example, in some embodiments, the base 491 comprises an annular shape that allows the fourth telescoping member 484 to slide into and out of both the base 491 as well as the third telescoping member 484. Such movement comes into play in the break-fit operation of the end cap 490 and base 491. In some embodiment, the base 491 comprises any number of shapes having an interior opening to accommodate the fourth telescoping member 484. In some embodiments, the base 491 is positioned to one or more sides of the slot 496 of the third telescoping member 484. Thus, the movement of the fourth telescoping member 484 is not impeded and the end cap 490 can still be held in place with a magnetic force.

The members 484, the connecting cables 486, the end magnet and the end cap 490 can be enclosed with a resilient member 492. Any suitable resilient member 492 can be used. In some configurations, the resilient member 492 is a strip of material. In other applications, the resilient member 492 forms an envelope around the members 484 and the end cap 490. As best shown in FIG. 42, the illustrated resilient member 492 resists movement of the end cap 490 away from the centerline CL. More importantly, the resilient member applies a restorative force when the members 484 extend outward.

Because the telescoping members 484 are nested and are slidingly connected and can include one or more connecting cables 486, the entire assembly can be locked into a position by locking only one of the members 484. In other words, the connecting cables 486 operate in a balanced manner and so stopping the movement of one member 484 relative to another member 484 causes all of the members 484 to stop. More particularly, by controlling the movement at lock point 494, the entire adjustment mechanism can be controlled. For example, clamping together the centermost member 484 and the adjacent member 484 will reduce or eliminate the likelihood of movement of the other members 484.

The members 484 can include slots 496. Pins 498 can extend between adjacent members 484 in a slot such that the members are coupled together. To provide the lock point 494, one of the pins 498 can extend through a slot 500 formed in the housing 482, as shown in FIG. 44. Other locking configurations also can be used. For example, multiple stops can be provided with a pin fitting into one of the holes that define the multiple stops. Desirably, the locking configuration will lock out movement between at least one of the members 484 and the housing 482 or will lock out movement between at least two adjacent members 484.

Figure 45:
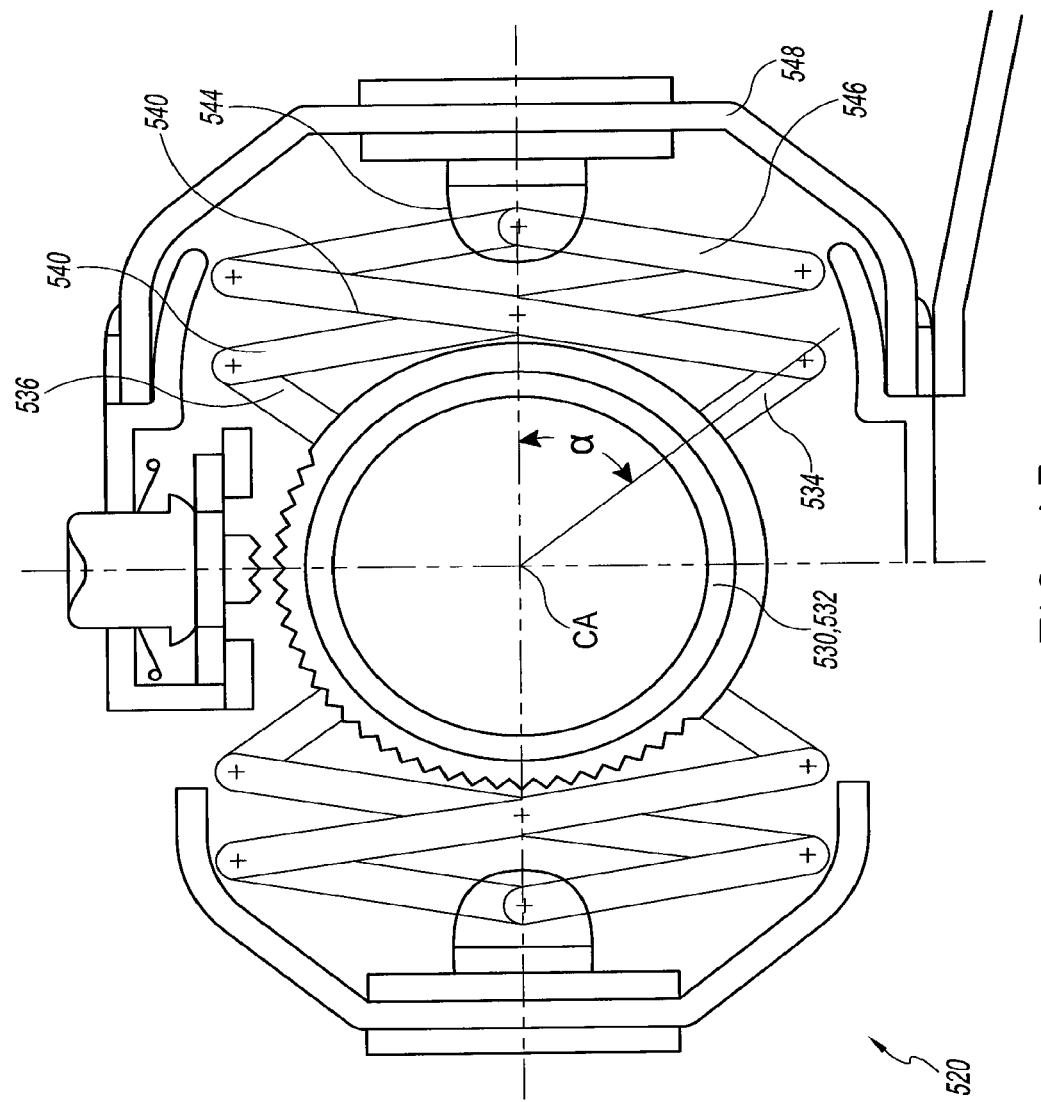
FIG. 45 is a schematic view of an adjustment mechanism that is arranged and configured in accordance with certain features, aspects and advantages of the present invention.
Figure 46:
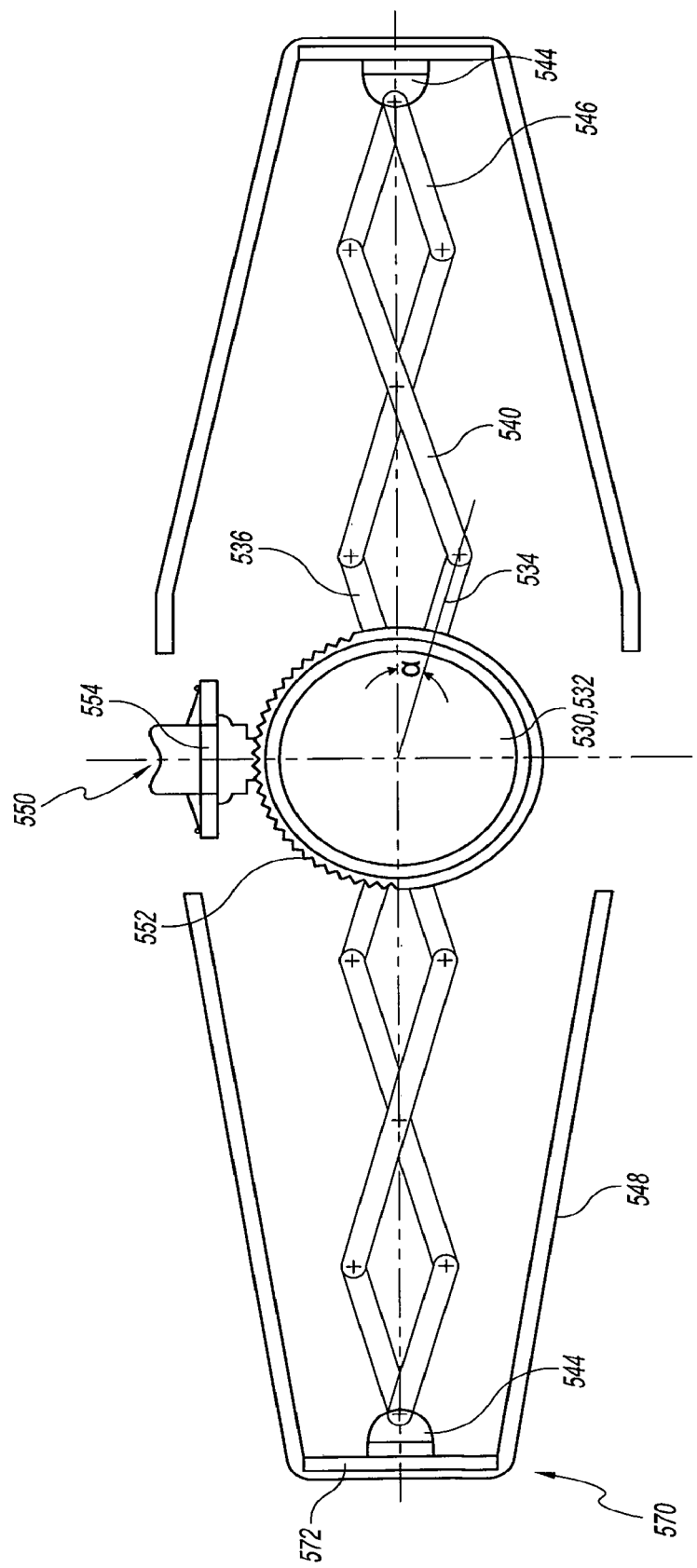
FIG. 46 is another schematic view of the adjustment mechanism of FIG. 45.
Figure 47:
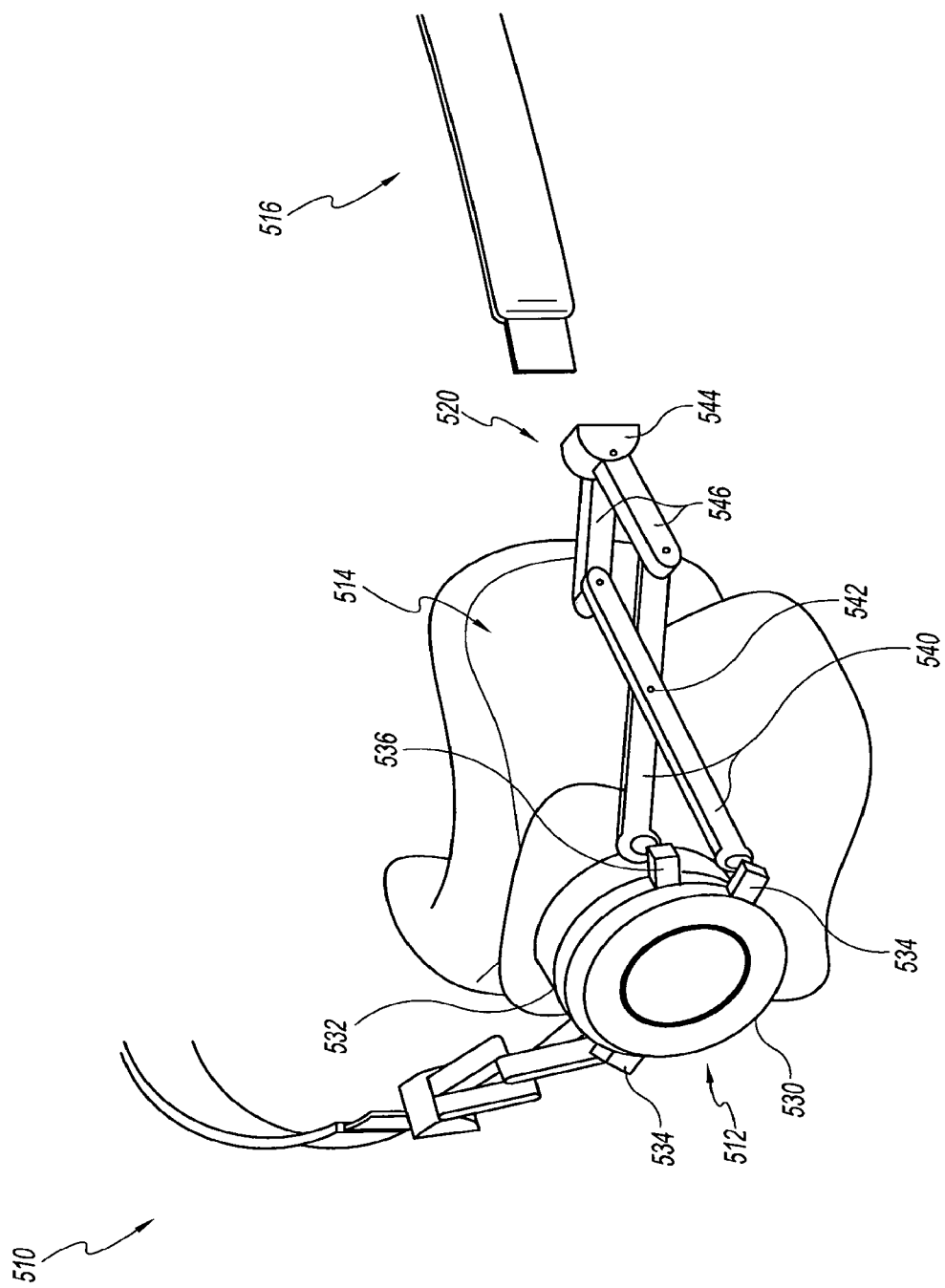
FIG. 47 is a schematic view of an interface having the adjustment mechanism of FIG. 45.
Figure 48:
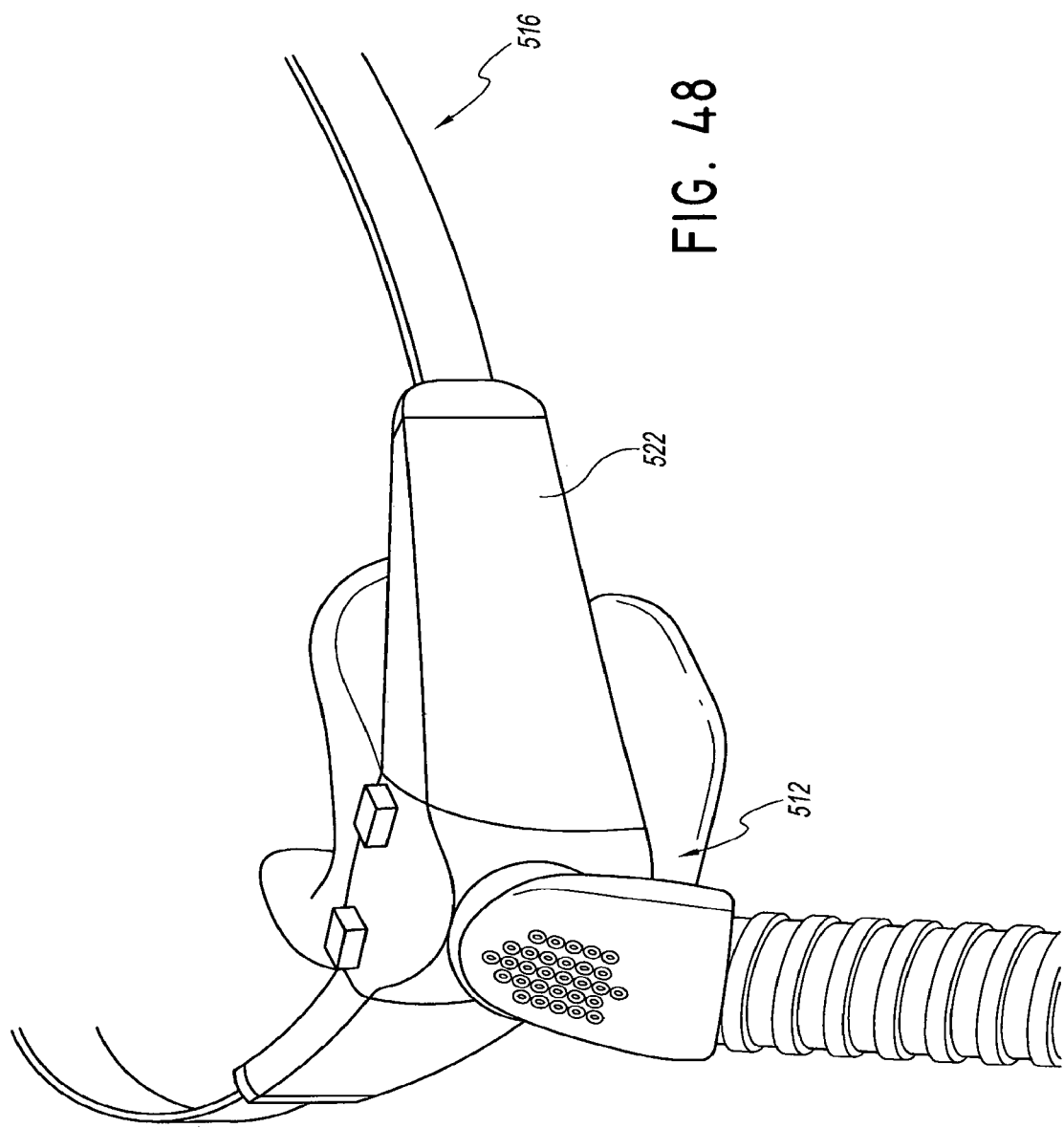
FIG. 48 is another schematic view of the interface of FIG. 47.

With reference now to FIGS. 45 through 50, and especially to FIGS. 47 and 48, an interface 510 is illustrated that has a frame 512, a seal 514, headgear 516 and an adjustment mechanism 520. The adjustment mechanism 520 can comprise a scissor mechanism, as will be described. In some configurations, the adjustment mechanism 520 can be connected to the frame 512. In some configurations, the adjustment mechanism 520 can be positioned within a housing 522. In some configurations, the housing 522 can be connected to the frame 512. In some configurations, the housing 522 forms a portion of the frame 512. In some configurations, the headgear 516 is connected to the frame 512 with the adjustment mechanism 520 contained within the housing 522.

With reference to FIG. 47, the adjustment mechanism 520 preferably comprises a first base component 530 and a second base component 532. The first and second components 530, 532 can comprise rings in some configurations. The first ring 530 and the second ring 532 can be positioned side by side with a single rotational axis extending through the two rings 530, 532. The first ring 530 includes two lugs 534 that are approximately 180 degrees apart. The second ring 532 includes two lugs 536 that also are approximately 180 degrees apart.

A pair of crossing scissor arms 540 connect to the lugs 534, 536 on each side of the rings 530, 532. The scissor arms 540 can be connected at a pin joint 542. In addition, the connections between the scissor arms 540 and the lugs 534, 536 can be pin joints. While one set of scissor arms 540 are shown for each side of the adjustment mechanism 520, other numbers can be used.

An end piece 544 can be connected to the scissor arms 540 with stub arms 546. A first end of the stub arms can be connected to the scissor arms 540 with pin joints. Similarly, a second end of the stub arms can be connected to the end piece 544 with pin joints.

When the end piece 544 is moved relative to the first ring 530 and the second ring 532, the stub arms 546 and the scissor arms 540 fold and unfold while the first ring 530 and the second ring 532 rotate. For example, as shown in FIG. 45, when the end piece 544 is in the contracted position, an angle α between the lugs 534 and an line that extends through the rotational axis of the rings 530, 532 as well as the pin joints of the scissor arms 540 is greater than when the end piece 544 is in the extended position. Thus, the angle α decreases as the distance between the center axis CA and the end piece 544 increases.

The adjustment mechanism 520 includes a biasing member 548. In the illustrated arrangement, the biasing member 548 urges the end piece 544 toward the center axis CA. In some configurations, the biasing member 548 can be one or more strips of an elastomeric material or a spring member. In some configurations, the biasing member 548 can be an enveloping stretchable fabric or other material. Any suitable biasing member can be used. In some configurations, the biasing member 548 also is the housing 522. The biasing member provides a restorative force that seeks to return the end pieces 544 to the contracted position.

With reference still to FIGS. 45 and 46, a locking component 550 can be used to secure the adjustment mechanism 520 in a desired position. For example, in the illustrated configuration, the rings 530, 532 can comprise one or more recesses 552 that extend around the periphery of the rings 530, 532. The recesses can be in the form of teeth, for example but without limitation. A pin 554 can engage with the recesses 552 to reduce or eliminate the likelihood of rotation of the rings 530, 532 when movement is not desired. In some configurations, only one of the first and second rings 530, 532 is secured against movement.

Figure 49:
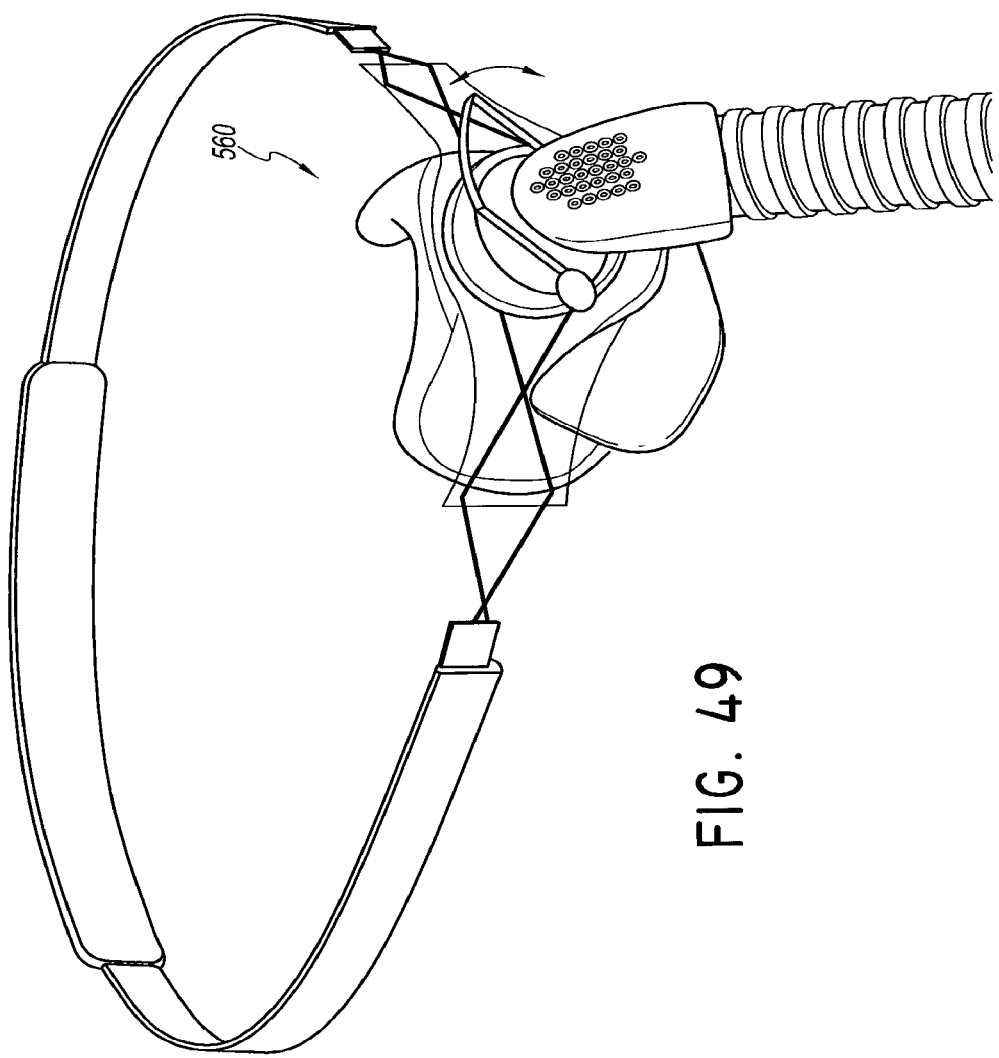
FIG. 49 is another schematic view of an interface having the adjustment mechanism of FIG. 45.
Figure 50:
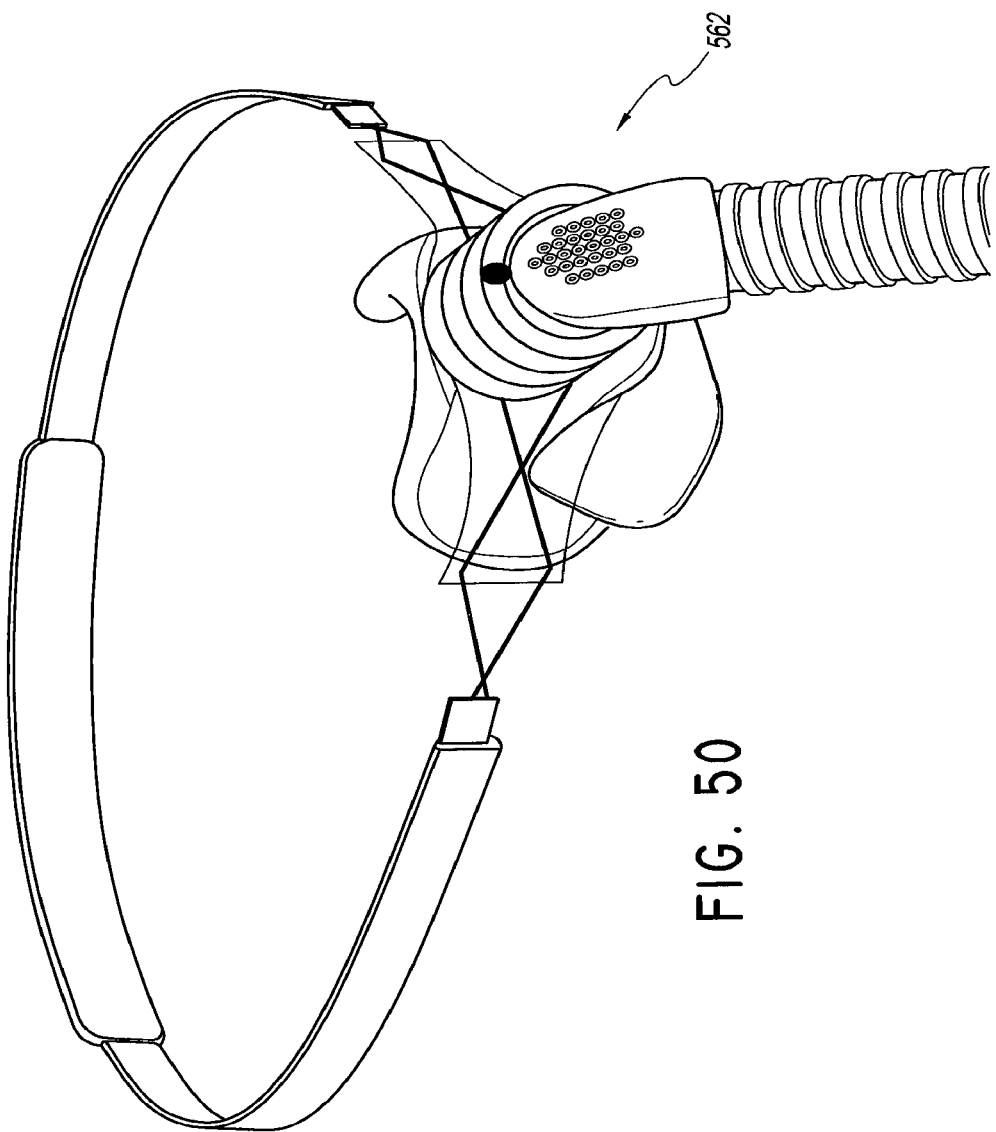
FIG. 50 is a schematic view of another interface having the adjustment mechanism of FIG. 45.

Of course, any other suitable locking mechanism can be used. FIG. 49 illustrates a cam assembly 560. The cam assembly 560 can use a cam mounted to a lever. The first and second rings 530, 532 can be squeezed together by the cam. As such, when the lever is moved to the locked position, at least one of the first and second rings 530, 532 cannot rotate. In some configurations, both of the first and second rings 530, 532 cannot rotate. Another mechanism, illustrated in FIG. 50, can include a threaded ring assembly 562, which features a locking ring that tightens against at least one of the first and second rings 530, 532. The locking ring, when tightened, can secure at least one or both of the first and second rings 530, 532 from rotation.

As discussed above, the adjustment mechanisms described herein can be used with break-fit assemblies where desired. With reference to FIG. 46, an integration of an adjustment mechanism and a break-fit assembly will be described. The adjustment mechanism has been described above. To integrate a break-fit assembly 570, the end piece 544 and a plate 572 can be releasably coupled together. In some configurations, the end piece 544 and the plate 572 can be magnetically coupled. In some configurations, at least one of the end piece 544 and the plate 572 is or includes a magnet. The magnetic coupling between the end piece 544 and the plate 572 is sufficiently strong to allow the connection to remain during treatment yet sufficiently weak to allow separation between the end piece 544 and the plate 572 when donning the interface 510. The elastic member 548 continues to stretch even beyond the full range of adjustment by the adjustment mechanism 520 (e.g., about an additional 50 mm). Thus, if the adjustment mechanism 520 is locked at a position between collapsed and extended, the elastic member 548 will continue to stretch when the plate 572 breaks free from the end piece 544 during donning of the interface 510.

While the adjustment mechanism 520 described with respect to FIGS. 45 through 48 featured a coordinated expansion to both sides due to the interconnecting rings 530, 532, an adjustment mechanism 580 can have independent movement of the two sides. For example, the adjustment mechanism 580 shown in FIGS. 51-53 can allow adjustment of two sides independently of each other. As illustrated, the adjustment mechanism 580 can include at least a first gear 582 and a second gear 584. The first gear 582 and the second gear 584 can be engaged such that rotation of one of the gears 582, 584 results in rotation of the other one of the gears 582, 584.

A first lever arm 586 can extend away from the first gear 582 and a second lever arm 588 can extend away from the second gear 584. The first lever arm 586 and the first gear 582 are coupled for rotation and the second lever arm 588 and the second gear 584 are coupled for rotation.

A pair of crossing scissor arms 590 connect to the lever arms 586, 588. The scissor arms 590 can be connected at a pin joint 592. In addition, the connections between the scissor arms 590 and the lever arms 582, 584 can be pin joints. While one set of scissor arms 590 are shown for each side of the adjustment mechanism 580, other numbers can be used.

An end piece 594 can be connected to the scissor arms 590 with stub arms 596. A first end of the stub arms 596 can be connected to the scissor arms 590 with pin joints.

Similarly, a second end of the stub arms 596 can be connected to the end piece 594 with pin joints.

Figure 51:
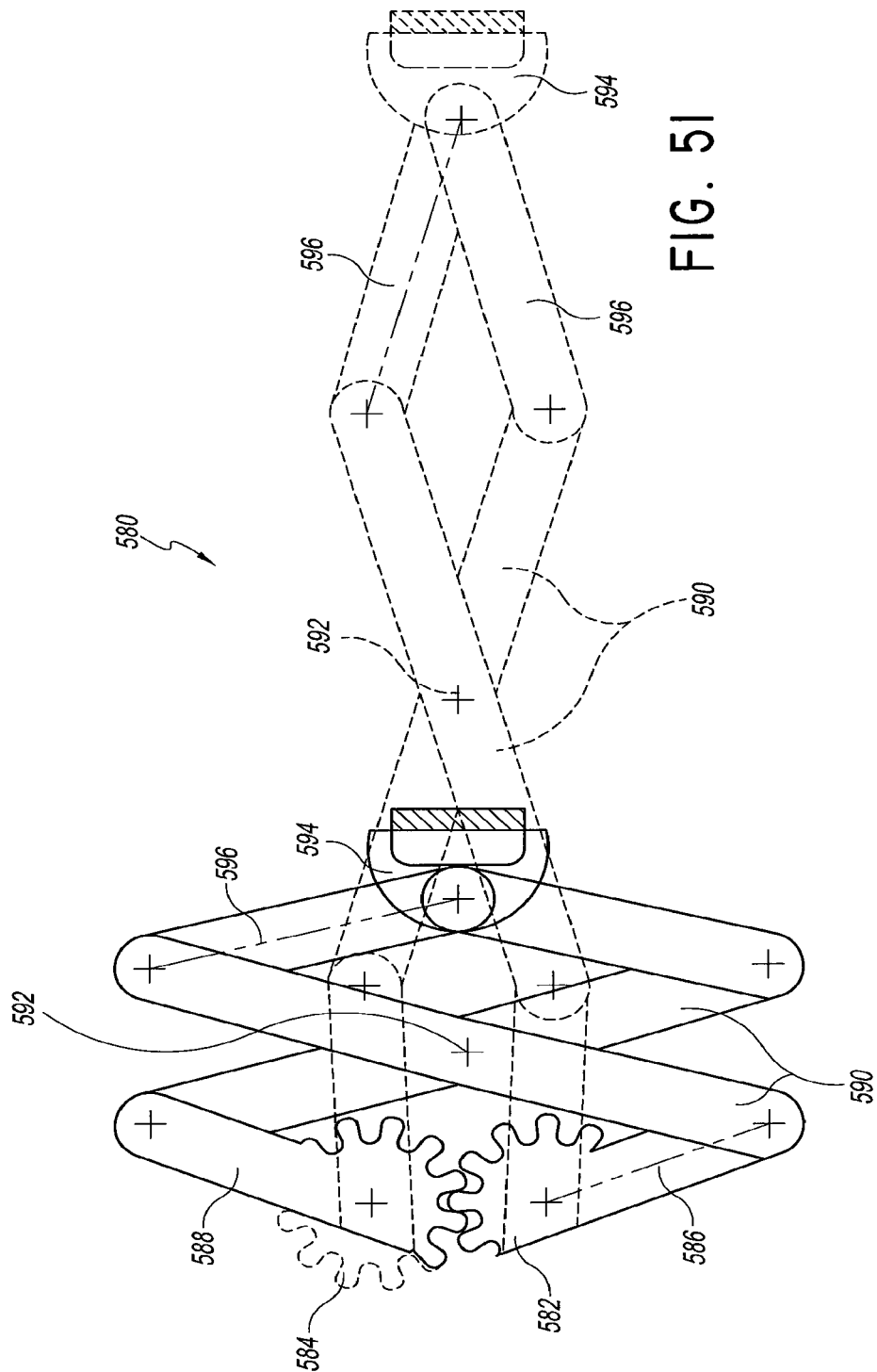
FIG. 51 is a schematic view of an adjustment mechanism that is arranged and configured in accordance with certain features, aspects and advantages of the present invention.

When the end piece 594 is moved relative to the gears 582, 584, the stub arms 596 and the scissor arms 590 fold and unfold while the gears 582, 584 rotate. As shown in FIG. 51, the end piece 594 can move between a contracted position (solid lines) and an extended position (dashed lines).

Figure 52:
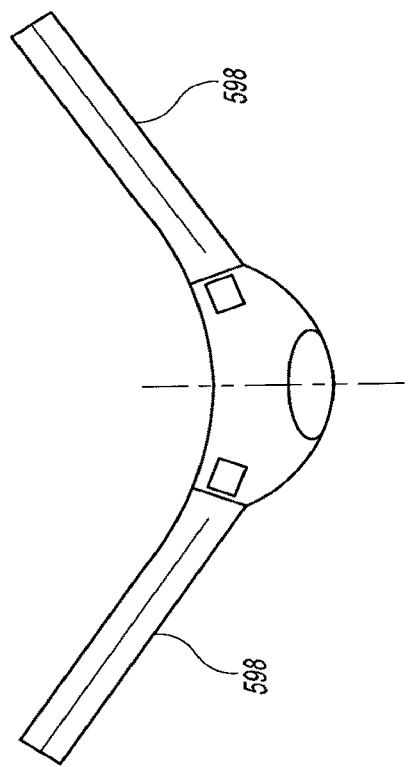
FIG. 52 is a schematic view of an interface having the adjustment mechanism of FIG. 51.
Figure 53:
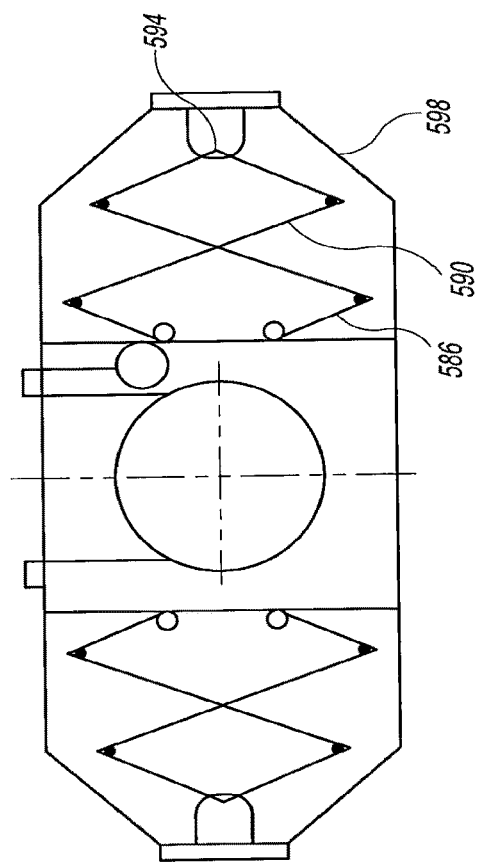
FIG. 53 is a schematic view of a portion of the interface of FIG. 52.

As shown in FIG. 52, the adjustment mechanism 580 can comprise an elastic cover 598, similar to the configurations described above. The cover 598 encloses the mechanical assembly and applies a force that urges the mechanism back to the contract position. Any of the biasing structures described herein can be used. In addition, the break-fit assembly described above can be integrated in the same manner. Effectively, relative to the other scissor arms assembly described above, the assembly of FIGS. 51-53 exchanges the two rings for four gears and isolates the movement of the two sides.

As described above, it is possible to use hook and loop fasteners with buckles or the like to provide an adjustment mechanism. With reference to FIGS. 54-58, a few assemblies that can be used in place of hook and loop fasteners are illustrated. These assemblies feature components that can be formed of silicone or another polymeric material. Accordingly, these features facilitate molding with either headgear or another component of the interface.

With reference to FIG. 54, a strap 610 is shown doubled back on itself. A slider 612 can be used to slide over at least a portion of the strap 610. The strap 610 can include one or more rails 614. The rails 614, as shown in FIG. 55, can include a narrow rib 616 with an enlarged cap 618. When pressed together on itself, each rail 614 can deflect. As illustrated, the enlarged cap 618 can interlock with itself to join the strap. The slider 612, as it slides over the doubled over portion of the strap 610, helps to cause the rails 614 to interlock. As an adjustment mechanism, the straps 610 allow a significant length that can be used and, because of the construction and the interlocking of the rails 614, the straps 610 will not be prone to having a free end dangling. In other words, the excess length is easily managed.

Figure 57:
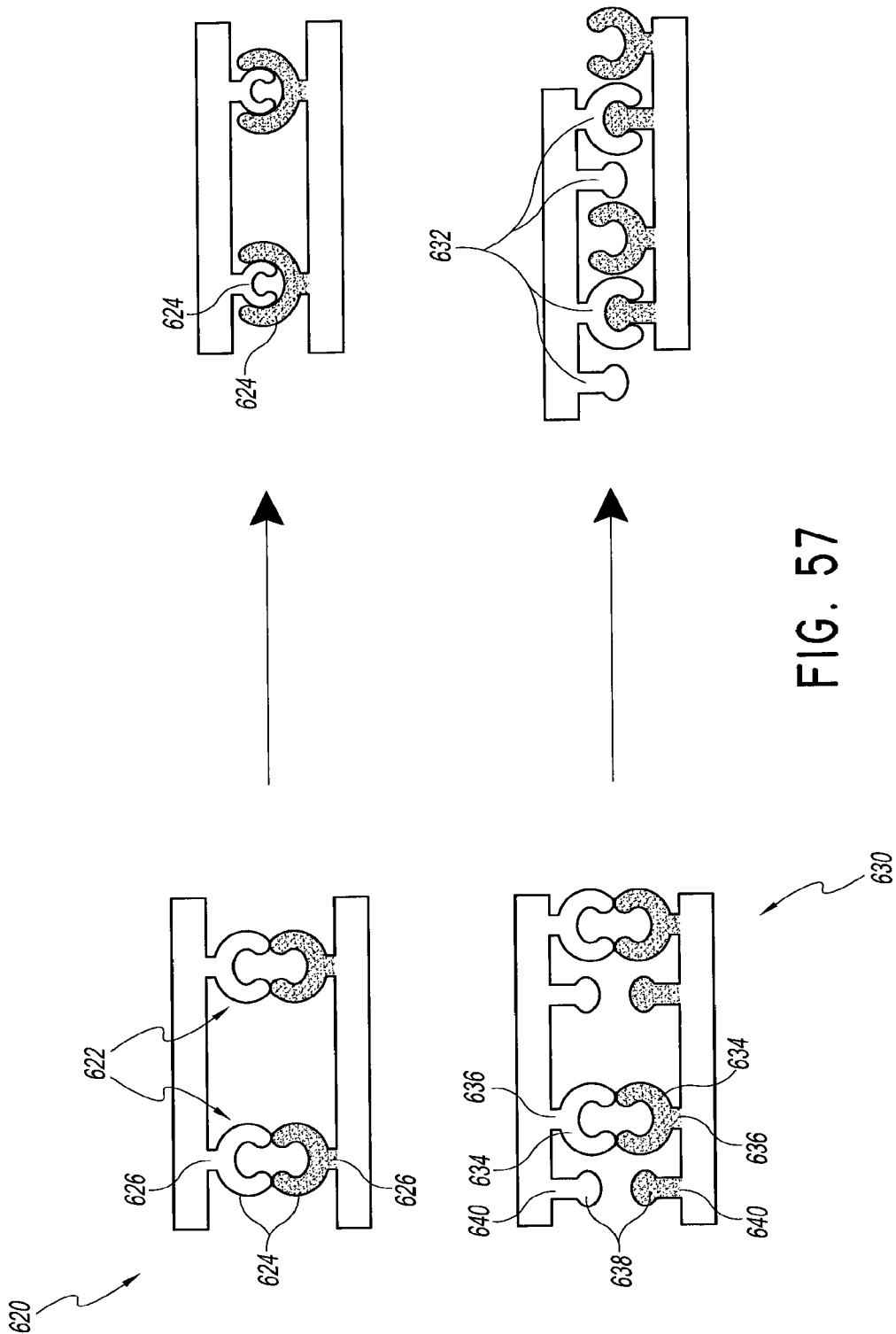
FIG. 57 is a group of cross-sectional views of other strap configurations that are arranged and configured in accordance with certain features, aspects and advantages of the present invention.

With reference to FIG. 57, another strap 620 is illustrated. The strap 620 comprises two rails 622. Each of the rails 622 can comprise a C-shaped cap 624 that sits atop a narrower rib 626. As illustrated, when pressed together, one of the two caps 624 will compress to fit inside of the other of the two caps 624. Thus, when the strap is doubled over itself and pressed together, the strap 620 doubled over portion can lock to itself in the longitudinal direction.

FIG. 57 also illustrates a second strap 630. The strap 630 comprises four rails 632. Two of the rails 632 each comprise a C-shaped cap 634 that sits atop a narrower rib 636. Two of the rails 632 each comprise a small head 638 that sits atop a narrower rib 640. When pressed together, the small head 638 can snap into the recess of the C-shaped cap 634. Thus, when the strap 630 is doubled over itself and pressed together, the strap 630 can lock to itself in the longitudinal direction.

Figure 58:
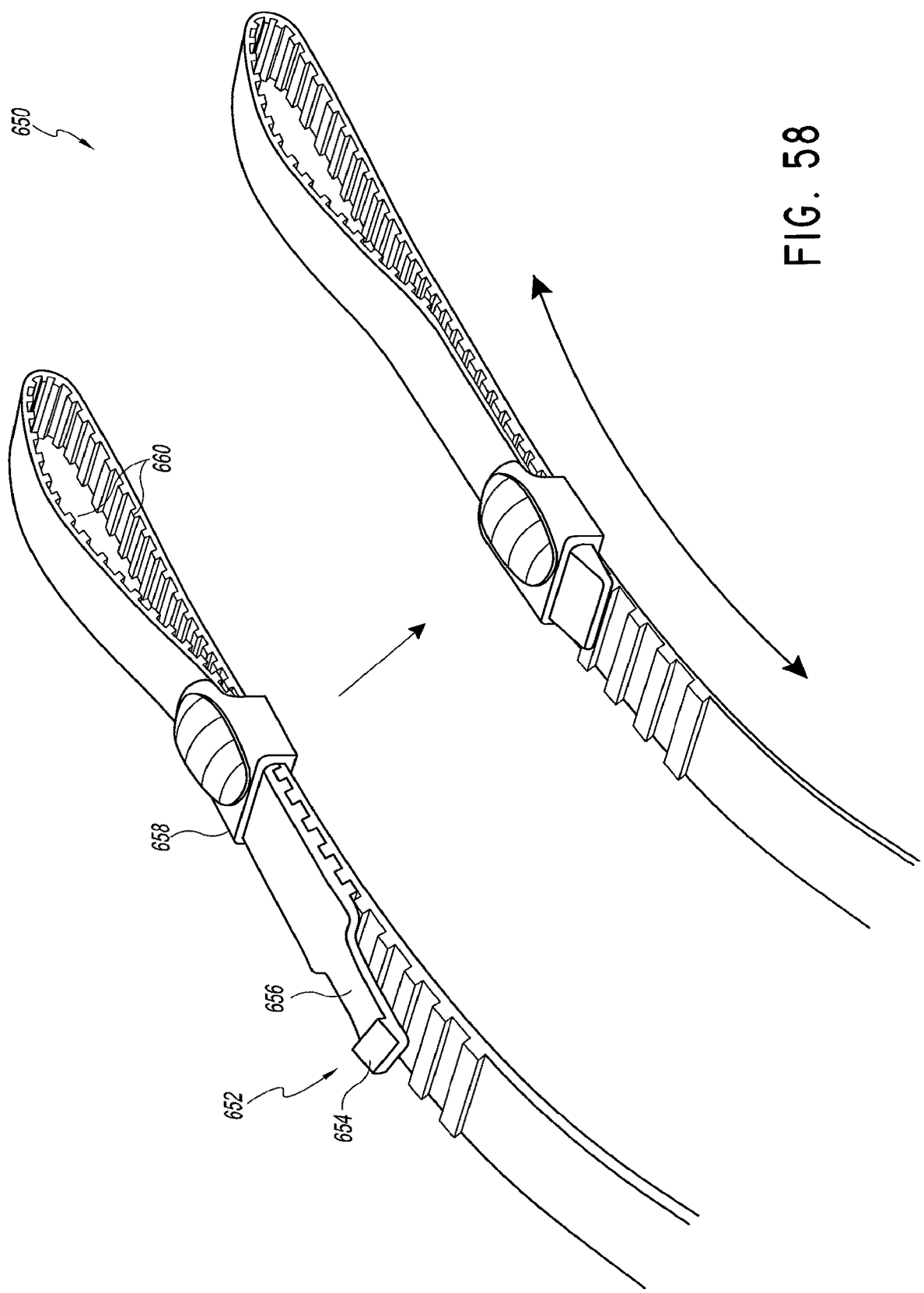
FIG. 58 is a pair of perspective views of further strap configurations having adjustment mechanisms that are arranged and configured in accordance with certain features, aspects and advantages of the present invention.
Figure 59:
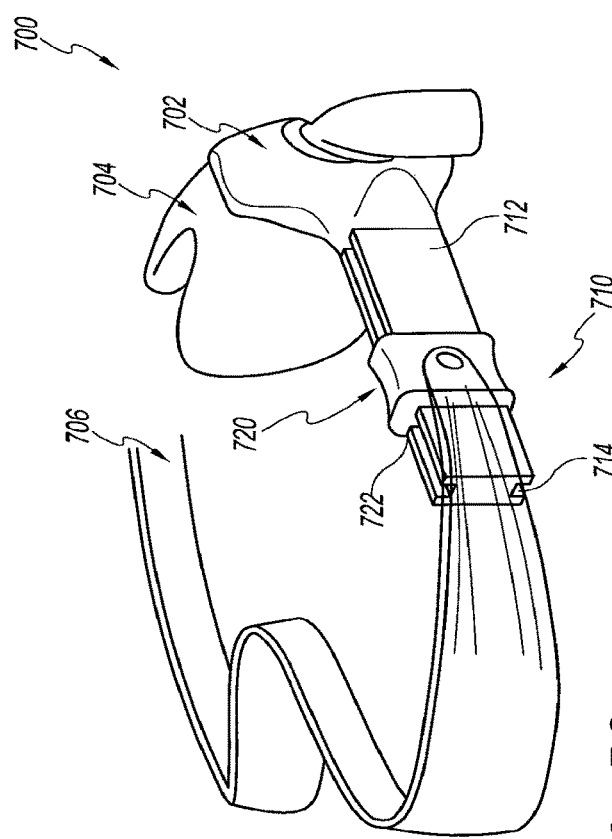
FIG. 59 is a perspective view of an interface with an adjustment mechanism that is arranged and configured in accordance with certain features, aspects and advantages of the present invention.

FIG. 58 shows another strap 650. The strap 650 can lock to itself in a transverse direction. As illustrated, the strap 650 can comprise an end 652 with a stop 654. In addition, the end 652 can include a tab 656, which can be sized to accommodate a slider member 658. The slider member 658 can track along the axial direction of the strap 650.

One side of the illustrated strap 650 includes transversely extending ribs 660. The ribs 660 are shaped to enable the ribs 660 to lock together when pressed. The other side of the illustrated strap 650 is substantially smooth.

The slider member 658 has an opening large enough to accommodate two thicknesses of the strap 650 so long as the two thicknesses have the ribs 660 interlocked. Accordingly, the tab portion 656 is generally smooth on both sides such that, when the slider member 658 is positioned over the tab portion 656, the location of the tab portion 656 can be adjusted (see lower portion of FIG. 58). Once positioned as desired, the slider member 658 can be slid away from the stop 654. As the slider member 658 traverses the strap 650, the ribs 660 are pressed together and the strap locks to itself in a transverse direction.

With reference now to FIGS. 59 through 62, an interface 700 is illustrated. The interface 700 includes a mask frame 702, a seal 704 and headgear 706. An adjustment mechanism 710 connects the headgear 706 to the balance of the interface 700.

In the illustrated configuration, the frame 704 comprises arms 712 that extend laterally outward. As illustrated, the arms 712 can include recessed grooves 714 that extend along one or both of the top and bottom.

The headgear 706 connects to a slide 720. In the illustrated configuration, the headgear 706 is pivotally connected to the slide 720. Other types of connections also can be used. The slide 720 can include a tooth 722 that fits into each of the recessed grooves 714 of the arms 712. The slide 720 should define a larger inside dimension than a corresponding outside dimension of the arm 712 such that the slide 720 can be compressed toward the arm 712.

Figure 60:
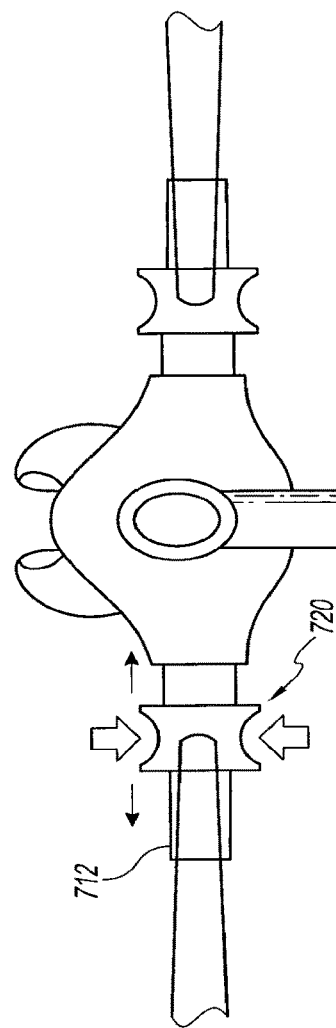
FIG. 60 is a front view of the interface of FIG. 59.
Figure 62:
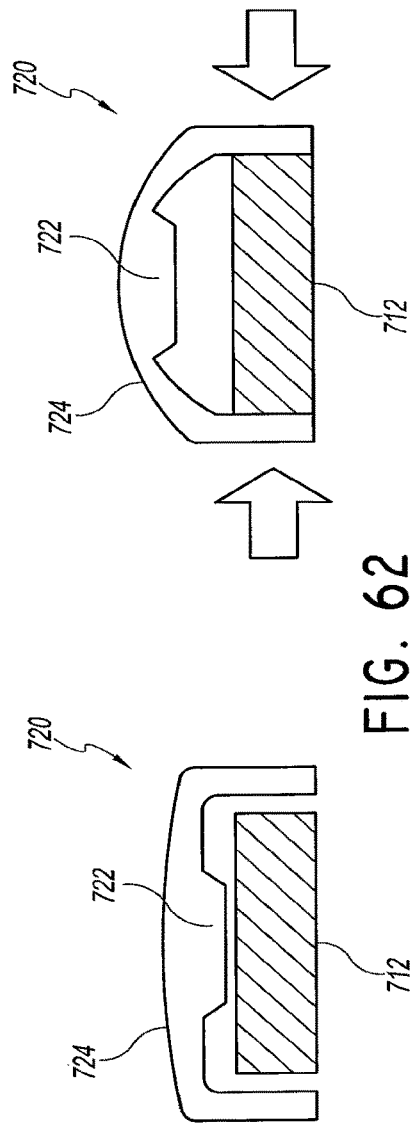
FIG. 62 is a pair of cross-sections of the portion of the interface of FIG. 61.

With reference to FIG. 60, the slide 720 generally is locked in position along the arm 712 until compressed. For example, as illustrated in FIG. 60, compressing the slide 720 in the direction of the teeth (e.g., vertically as shown) releases the slide 720 and enables the slide 720 to translate along the arm 712. FIG. 62 demonstrates that the slide 720 can include a tooth or friction generator 722 that contacts the arm 712 until the slide 720 is compressed. When the slide 720 is compressed toward the arm 712, a wall 724 of the slide 720 deflects away from the arm 712, which raises the tooth or friction generator 722 away from the arm 712 to facilitate movement of the slide 720 along the arm 712.

Figure 61:
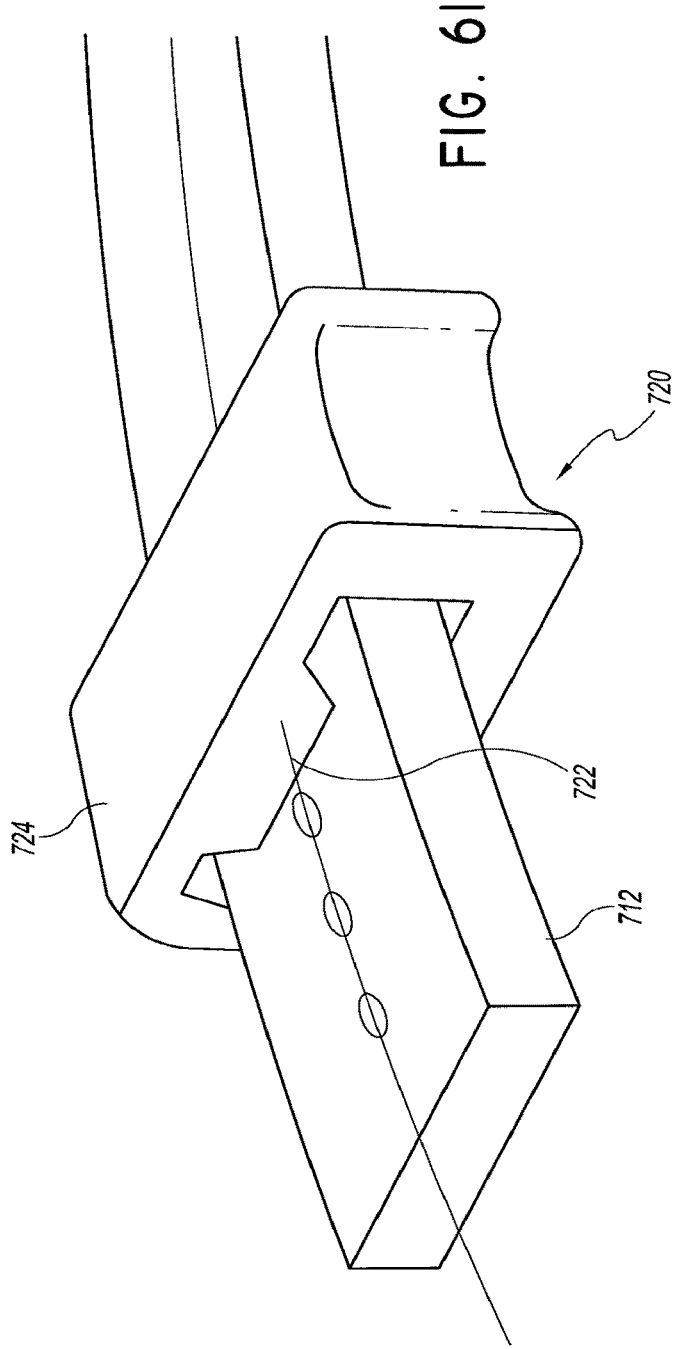
FIG. 61 is an enlarged perspective view of a portion of the interface of FIG. 59.

As illustrated in FIG. 61, the arm 712 can include markings or indicia to assist with determining the location of the slide 720 along the length of the arm 712.

As discussed above, a non-stretching headgear generally indicates that the headgear should be set to a specific, customized size for each user. Preferably, the sizing is performed once and then is not changed during subsequent use. Using the break-fit assemblies described herein, the sizing can be temporarily adjusted for ease of donning the interface while facilitating automatic reconnection of the headgear to the predetermined size. As discussed above, the break-fit assembly can be positioned on the mask (e.g., on the frame or on the seal), in-line by connecting to one or more of the straps of the headgear, or in another portion of the headgear (e.g., along a seam in the back of the headgear).

In some configurations, a component assembly can be provided to reduce the likelihood of accidental adjustment of a predetermined sizing of the headgear. For example but without limitation, the component assembly can be created to operate an adjustment mechanism only with deliberate interaction. In one configuration, a key can be used to lock or unlock the adjustment mechanism. By key, it is intended to have a broad interpretation of a device that establishes control over the mechanism. The key could be a traditional key or could be another item. For example, the key could be a magnet or a magnetic component that attracts another component to interact with an adjustment mechanism. By way of another example, the key could be a household item, such as a screwdriver, pin, or the like. In one configuration, once the size has been adjusted, a component can be removed to lock the adjustment mechanism against inadvertent or undesirable resizing.

In some configurations, electronics can be added to improve the function of the interface. For example, a strap or other component can have an incorporated track that acts as an electronic tape measure. When an initial fitting of the interface is performed (e.g., by a sleep technician), the initial sizing can be bookmarked in an electronic component of the interface. With each subsequent fitting or donning of the interface, the electronics can signal when the headgear is at the proper or predetermined size. For example, the user can stretch the interface during donning and then tighten until the electronics indicate that the predetermined length has been reached. Similarly, an actuator could be provided to automatically tighten the interface to the predetermined size. The actuator could be a small motor, solenoid or the like. The actuator could be integrated into the frame or the headgear, for example but without limitation. Furthermore, using the electronics, operating characteristics of a CPAP device could be monitored such that an adjustment could be made to the headgear automatically to compensate for leaks as soon as the leaks occur or are likely to occur.

While various embodiments have been described, it should be noted that any of the adjustment mechanisms can be combined with any of the break-fit assemblies. In addition, the adjustment mechanisms can be used without a break-fit assembly and the break-fit assemblies can be used without an adjustment mechanism. Further, any interface (i.e., mask and headgear) can be used with either or both of an adjustment mechanism described herein and/or a break-fit assembly.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

What is claimed is:

1. An interface assembly for use in providing a breathing treatment, the interface assembly comprising:
    a mask comprising a frame and a seal supported by the frame;
    a headgear connected to the mask; and
    a break-fit assembly configured to selectively lengthen a loop defined by the mask and the headgear when a predetermined force has been exceeded and return the loop to a use length when the predetermined force has not been exceeded;
    wherein the break-fit assembly comprises a magnetic coupling that resists elongation from a first length to a second length until a force is applied that exceeds a predetermined force, wherein the magnetic coupling comprises two magnetic members, wherein a flexible sheath envelopes the two magnetic members, and wherein stretching of the flexible sheath upon movement of the two magnetic members away from each other establishes a restoration force that acts to return the two magnetic members toward each other for reconnection.

2. The interface assembly of claim 1, wherein the headgear is substantially non-stretch.

3. The interface assembly of claim 1, wherein the break-fit assembly is positioned between the frame and the headgear.

4. The interface assembly of claim 1, wherein the headgear comprises a generally inelastic portion.

5. The interface assembly of claim 4, wherein two break-fit assemblies connect the generally inelastic portion to the frame.

6. The interface assembly of claim 1, wherein the two magnetic members are fixed axially within the flexible sheath.

7. The interface assembly of claim 1, wherein the two magnetic members exert a coupling force of greater than about 4 N.

8. The interface assembly of claim 1, wherein the predetermined force is greater than a maximum force created by pressurized breathing gases within the interface assembly in use.

* * * * *